United States Patent
Bystrom et al.

(10) Patent No.: US 10,921,331 B2
(45) Date of Patent: Feb. 16, 2021

(54) HDL-ASSOCIATED PROTEIN BIOMARKER PANEL DETECTION

(71) Applicant: Cleveland HeartLab, Inc., Cleveland, OH (US)

(72) Inventors: Cory Bystrom, Cleveland, OH (US); Timothy Collier, Cleveland, OH (US)

(73) Assignee: Cleveland Heartlab, Inc., Cleveland, OH (US)

( * ) Notice: Subject to any disclaimer, the term of this patent is extended or adjusted under 35 U.S.C. 154(b) by 208 days.

(21) Appl. No.: 15/656,592

(22) Filed: Jul. 21, 2017

(65) Prior Publication Data
US 2018/0024152 A1    Jan. 25, 2018

Related U.S. Application Data

(60) Provisional application No. 62/365,175, filed on Jul. 21, 2016.

(51) Int. Cl.
*G01N 33/92*    (2006.01)

(52) U.S. Cl.
CPC ....... *G01N 33/92* (2013.01); *G01N 2333/775* (2013.01); *G01N 2560/00* (2013.01); *G01N 2570/00* (2013.01); *G01N 2800/32* (2013.01); *G01N 2800/324* (2013.01); *G01N 2800/50* (2013.01)

(58) Field of Classification Search
CPC .... G01N 33/68; G01N 33/92; G01N 33/6848; G01N 2333/775; G01N 2560/00; G01N 2570/00; G01N 2800/32; G01N 2800/234; G01N 2800/50
See application file for complete search history.

(56) References Cited

U.S. PATENT DOCUMENTS

| | | | |
|---|---|---|---|
| 7,575,876 B2 * | 8/2009 | Zhang | G01N 33/6896 435/7.1 |
| 8,241,861 B1 | 8/2012 | Heinecke et al. | |
| 9,134,326 B2 * | 9/2015 | Jacobs | G01N 33/6893 |
| 2007/0099242 A1 | 5/2007 | Heinecke et al. | |
| 2009/0012716 A1 | 1/2009 | Urdea et al. | |
| 2009/0118133 A1 * | 5/2009 | Melrose | G16B 20/00 506/8 |
| 2009/0155812 A1 * | 6/2009 | Breyer | G01N 33/5091 435/7.1 |
| 2014/0243233 A1 * | 8/2014 | Altmann | G01N 33/92 506/9 |

FOREIGN PATENT DOCUMENTS

WO    WO 2015/175864 A1    11/2015

OTHER PUBLICATIONS

Hoofnagle et al. Multiple Reaction Monitoring-Mass Spetrometric Assays can Accurately Measure Many Protein Concentrations in Complex Mixtures. Clinical Chemistry. 58 (4): 1-7 (Apr. 2012).*
Supplementary Partial European Search Report dated Jan. 31, 2020, in EP 17831958.8.

* cited by examiner

*Primary Examiner* — Gailene Gabel
(74) *Attorney, Agent, or Firm* — Foley & Lardner LLP

(57) ABSTRACT

Provided herein are methods, systems, and compositions for detecting one or more HDL-associated proteins (e.g., ApoC3; ApoC3 and ApoA1; ApoC3 and SAA1/2; or proteins in Biomarker Panels 1-30) in a sample from a subject with, or suspected of having, cardiovascular disease (CVD) or other HDL related disease. In certain embodiments, such methods, systems, and compositions are used to determine the approximate risk of CVD (or other disease) for a subject, and/or the approximate cholesterol efflux capacity (CEC) of a sample.

21 Claims, 10 Drawing Sheets

Specification includes a Sequence Listing.

HDL-ASSOCIATED PROTEIN BIOMARKER PANEL DETECTION

CROSS-REFERENCE TO RELATED APPLICATIONS

The present application claims priority to U.S. provisional application 62/365,175 filed Jul. 21, 2016, which is herein incorporated by reference in its entirety.

FIELD OF THE INVENTION

Provided herein are methods, systems, and compositions for detecting one or more HDL-associated proteins (e.g., ApoC3; ApoC3 and ApoA1; ApoC3 and SAA1/2; or proteins in Biomarker Panels 1-30) in a sample from a subject with, or suspected of having, cardiovascular disease (CVD) or other HDL related disease. In certain embodiments, such methods, systems, and compositions are used to determine the approximate risk of CVD (or other disease) for a subject, and/or the approximate cholesterol efflux capacity (CEC) of a sample. In particular embodiments, the systems and compositions are composed of a sample from a subject with, or suspected of having CVD, and an HDL-associated binding agent or mass spectrometry standard.

BACKGROUND

Despite recent advances in both our understanding of the pathophysiology of cardiovascular disease and the ability to image atherosclerotic plaque, accurate determination of risk in stable cardiac patients remains a challenge. The clinically unidentified high-risk patient who does not undergo aggressive risk factor modification and experiences a major adverse cardiac event is of great concern. Similarly, more accurate identification of low-risk subjects is needed to refocus finite health care resources to those who stand most to benefit. Most current clinical risk assessment tools involve algorithms developed from epidemiology based studies of untreated primary prevention populations and are limited in their application to a higher risk and medicated cardiology outpatient setting. Despite considerable interest, efforts to incorporate more holistic array-based phenotyping technologies (e.g., genomic, proteomic, metabolomic, expression array) for improved cardiac risk stratification remain in its infancy and have yet to be translated into efficient and robust platforms amenable to the high throughput demands of clinical practice.

SUMMARY OF THE INVENTION

Provided herein are methods, systems, and compositions for detecting one or more HDL-associated proteins (e.g., ApoC3; ApoC3 and ApoA1; ApoC3 and SAA1/2; or proteins in Biomarker Panels 1-30) in a sample from a subject with, or suspected of having, cardiovascular disease (CVD) or other HDL related disease. In certain embodiments, such methods, systems, and compositions are used to determine the approximate risk of CVD (or other disease) for a subject, and/or the approximate cholesterol efflux capacity (CEC) of a sample. In particular embodiments, the systems and compositions are composed of a sample from a subject with, or suspected of having CVD, and an HDL-associated binding agent or mass spectrometry standard.

In some embodiments, provided herein are methods comprising: detecting the level of at least one HDL-associated protein in a sample from a subject, wherein the at least one HDL-associated protein comprises ApoC3, and wherein the subject has, or is suspected of having, cardiovascular disease. In certain embodiments, the sample is a purified high-density lipoprotein sample. In other embodiments, the sample is selected from the group consisting of: a serum sample, a plasma sample, and a blood sample. In additional embodiments, the methods further comprise: normalizing the level of the at least one HDL-associated protein to the approximate level of total HDL particles or ApoA1 or HDL-cholesterol to generate at least one normalized HDL protein value.

In particular embodiments, the determining the approximate level of total HDL particles or ApoA1 or HDL-cholesterol in the sample comprises determining the level of an internal standard added to the sample, wherein the internal standard comprises a labeled HDL protein. In some embodiments, the detecting the level of at least one HDL protein comprises adding a reagent to the sample, wherein the reagent digests HDL proteins in the sample (e.g., Lyc-C, pepsin, trypsin, etc.). In other embodiments, HDL-associated proteins are detected without prior digestion (e.g., intact HDL-associated proteins are detected).

In other embodiments, the detecting the level of at least one HDL-associated protein comprises performing an assay on a least a portion of the sample that detects ApoC3 or a fragment of ApoC3. In certain embodiments, the detecting the level of at least one HDL-associated protein further comprises adding a labeled or un-labelled ApoC3 protein or protein fragment standard to the sample, and detecting the ApoC3 standard. In further embodiments, the ApoC3 standard comprises or consists of the amino acid sequence shown in SEQ ID NO:11. In certain embodiments, the assay is a mass spectrometry assay or immunoassay.

In particular embodiments, the at least one HDL-associated protein further comprises serum amyloid A 1 or 2 (SAA1 and/or SAA2, referred to herein as "SAA1/2"). In further embodiments, the detecting the level of at least one HDL protein comprises performing an assay that detects: i) ApoC3, or fragment of ApoC3, and ii) SAA1/2, or a fragment of SAA1/2. In additional embodiments, the detecting the level of at least one HDL-associated protein further comprises adding a labeled or un-labelled SAA1/2 protein or protein fragment standard to the sample, and detecting the SAA1/2 standard. In certain embodiments, the SAA1/2 standard comprises or consists of the amino acid sequence shown in SEQ ID NO:35.

In further embodiments, the at least one HDL-associated protein further comprises Apolipoprotein 1 (ApoA1). In some embodiments, the detecting the level of at least one HDL-associated protein comprises performing an assay that detects: i) ApoC3, or fragment of ApoC3, and ii) ApoA1, or a fragment of ApoA1. In other embodiments, the detecting the level of at least one HDL-associated protein comprises performing an assay that detects: i) ApoC3, or fragment of ApoC3, ii) SAA1/2, or a fragment of SAA1/2, and iii) ApoA1, or a fragment of ApoA1. In certain embodiments, the detecting the level of at least one HDL-associated protein further comprises adding a labeled or un-labelled ApoA1 protein or protein fragment standard to the sample, and detecting the ApoA1 standard. In other embodiments, the ApoA1 standard comprises or consists of the amino acid sequence shown in SEQ ID NOS:1 or 2.

In further embodiments, the at least one HDL-associated protein further comprises Apolipoprotein C1 (ApoC1). In some embodiments, the detecting the level of at least one HDL-associated protein comprises performing an assay that detects: i) ApoC3, or fragment of ApoC3, and ii) ApoC1, or a fragment of ApoC1. In further embodiments, the at least one HDL-associated protein further comprises Apolipoprotein C1 (ApoC2). In some embodiments, the detecting the level of at least one HDL-associated protein comprises performing an assay that detects: i) ApoC3, or fragment of ApoC3, and ii) ApoC1, or a fragment of ApoC2. In further embodiments, the at least one HDL-associated protein further comprises Apolipoprotein C4 (ApoC4). In some embodiments, the detecting the level of at least one HDL-associated protein comprises performing an assay that detects: i) ApoC3, or fragment of ApoC3, and ii) ApoC1, or a fragment of ApoC4. In particular embodiments, the detecting the level of at least one HDL-associated protein comprises performing an assay that detects: i) ApoC3, or fragment of ApoC3, ii) ApoA1, or a fragment of ApoA1, and iii) ApoC1, or a fragment of ApoC1. In certain embodiments, the detecting the level of at least one HDL-associated protein comprises performing an assay that detects: i) ApoC3, or fragment of ApoC3, ii) ApoA1, or a fragment of ApoA1, and iii) ApoC2, or a fragment of ApoC2.

In some embodiments, the at least one HDL-associated protein further comprises Apolipoprotein L1 (ApoL1) and phospholipid transfer protein (PLTP). In other embodiments, the detecting the level of at least one HDL-associated protein comprises performing an assay that detects: i) ApoC3, or fragment of ApoC3, ii) SAA1/2, or a fragment of SAA1/2, iii) ApoL1, or a fragment of ApoL1, and iv) PLTP or a fragment of PLTP. In other embodiments, the detecting the level of at least one HDL-associated protein further comprises adding a labeled or un-labelled ApoL1 protein or protein fragment standard and/or a labeled or un-labelled PLTP protein or protein fragment standard, to the sample, and detecting the ApoL1 standard and/or the PLTP standard. In additional embodiments, the ApoL1 standard comprises or consists of the amino acid sequence shown in SEQ ID NOS:18 or 19, and wherein the PLTP standard comprises or consists of SEQ ID NOS:31 or 32.

In other embodiments, the at least one HDL-associated protein further comprises Apolipoprotein E (ApoE). In some embodiments, the detecting the level of at least one HDL-associated protein comprises performing an assay that detects: i) ApoC3, or fragment of ApoC3, ii) SAA1/2, or a fragment of SAA1/2, iii) ApoL1, or a fragment of ApoL1, iv) PLTP or a fragment of PLTP, and v) ApoE or a fragment of ApoE. In other embodiments, the detecting the level of at least one HDL-associated protein further comprises adding a labeled or un-labelled ApoE protein or protein fragment standard to the sample, and detecting the ApoE standard. In further embodiments, the ApoE standard comprises or consists of the amino acid sequence shown in SEQ ID NOS:15 or 16.

In certain embodiments, the at least one HDL-associated protein further comprises Apolipoprotein A1 (ApoA1) and Apolipoprotein D (ApoD). In further embodiments, the detecting the level of at least one HDL-associated protein comprises performing an assay that detects: i) ApoC3, or fragment of ApoC3, ii) SAA1/2, or a fragment of SAA1/2, iii) ApoL1, or a fragment of ApoL1, iv) PLTP or a fragment of PLTP, v) ApoE or a fragment of ApoE, vi) ApoA1 or a fragment of ApoA1, and vii) ApoD or a fragment of ApoD. In some embodiments, the detecting the level of at least one HDL-associated protein further comprises adding a labeled or un-labelled ApoD protein or protein fragment standard to the sample, and detecting the ApoD standard. In particular embodiments, the ApoD standard comprises or consists of the amino acid sequence shown in SEQ ID NOS:13 or 14. In other embodiments, the detecting the level of at least one HDL-associated protein further comprises adding a labeled or un-labelled ApoA1 protein or protein fragment standard to the sample, and detecting the ApoA1 standard.

In other embodiments, the at least one HDL-associated protein further comprises Apolipoprotein M (ApoM) and phospholipid transfer protein (PLTP). In some embodiments, the detecting the level of at least one HDL-associated protein comprises performing an assay that detects: i) ApoC3, or fragment of ApoC3, ii) SAA1/2, or a fragment of SAA1/2, iii) ApoM, or a fragment of ApoM, and iv) PLTP or a fragment of PLTP. In further embodiments, the detecting the level of at least one HDL-associated protein further comprises adding a labeled or un-labelled ApoM protein or protein fragment standard to the sample, and/or a labeled or un-labelled PLTP protein or protein fragment standard, and detecting the ApoM and/or PLTP standard. In additional embodiments, the ApoM standard comprises or consists of the amino acid sequence shown in SEQ ID NO:20, and wherein the PLTP standard comprises or consists of the amino acid sequence shown SEQ ID NOS:31 or 32.

In additional embodiments, the at least one HDL-associated protein further comprises Apolipoprotein C1 (ApoC1). In further embodiments, the detecting the level of at least one HDL-associated protein comprises performing an assay that detects: i) ApoC3, or fragment of ApoC3, ii) SAA1/2, or a fragment of SAA1/2, and iii) ApoC1, or a fragment of ApoC1. In some embodiments, the detecting the level of at least one HDL-associated protein further comprises adding a labeled or un-labelled ApoC1 protein or protein fragment standard to the sample, and detecting the ApoC1 standard. In certain embodiments, the ApoC1 standard comprises or consists of the amino acid sequence shown in SEQ ID NOS:7 or 8.

In additional embodiments, the at least one HDL-associated protein further comprises Apolipoprotein D (ApoD). In further embodiments, the detecting the level of at least one HDL-associated protein comprises performing an assay that detects: i) ApoC3, or fragment of ApoC3, ii) SAA1/2, or a fragment of SAA1/2, and iii) ApoD, or a fragment of ApoD. In other embodiments, the detecting the level of at least one HDL-associated protein further comprises adding a labeled or un-labelled ApoD protein or protein fragment standard to the sample, and detecting the ApoD standard. In some embodiments, the ApoD standard comprises or consists of the amino acid sequence shown in SEQ ID NOS:13 or 14.

In some embodiments, the at least one HDL-associated protein further comprises, or consists of, at least additional protein selected from the group consisting of: CLU, ApoE, CETP, PON1, ApoC1, ApoA2, ApoC2, ApoM, PLTP, and ApoL1. In other embodiments, the detecting the level of at least one HDL-associated protein comprises performing an assay that detects: i) ApoC3, or fragment of ApoC3, ii) SAA1/2, or a fragment of SAA1/2, and iii) the at least one additional protein or fragment thereof. In particular embodiments, the detecting the level of at least one HDL-associated protein further comprises adding a labeled or un-labelled protein or protein fragment standard corresponding to the at least one additional protein, and detecting the corresponding standard. In further embodiments, the corresponding standard comprises or consists of the amino acid sequence shown in SEQ ID NOS: 23, 24, 15, 16, 21, 22, 33, 34, 7, 8, 3, 4, 9, 10, 20, 31, 32, 18, and 19.

In certain embodiments, the at least one HDL-associated protein further comprises ApoC1 and ApoC2. In other embodiments, the detecting the level of at least one HDL protein comprises performing an assay that detects: i) ApoC3, or fragment of ApoC3, ii) ApoC1, or fragment of ApoC1, and iii) ApoC2, or fragment of ApoC2. In additional embodiments, the detecting the level of at least one HDL-associated protein further comprises adding a labeled or un-labelled ApoC1 protein or protein fragment standard to the sample, and/or a labeled or un-labelled ApoC2 protein or protein fragment standard to the sample; and detecting the ApoC1 and/or ApoC2 standard. In further embodiments, the ApoC1 standard comprises or consists of the amino acid sequence shown in SEQ ID NO:7 or 8, and wherein the ApoC2 standard comprises or consists of the amino acid sequence shown in SEQ ID NO:9 or 10. In further embodiments, the at least one HDL-associated protein further comprises Apolipoprotein C1 (ApoC1) and at least one additional protein selected from the group consisting of: ApoM, ApoA1, ApoC2, ApoC4, CLU, SAA4, ApoL1, HP, C3 and PLTP. In further embodiments, the detecting the level of at least one HDL-associated protein comprises performing an assay that detects: i) ApoC3, or fragment of ApoC3, ii) SAA1/2, or a fragment of SAA1/2, iii) ApoC1, or a fragment of ApoC1, and iv) the at least one additional protein or fragment thereof. In further embodiments, the detecting the level of at least one HDL-associated protein further comprises adding a labeled or un-labelled ApoC1 protein or protein fragment standard, and/or a labeled or un-labelled additional protein or protein fragment standard, and detecting the ApoC1 standard and/or the additional protein standard. In other embodiments, the ApoC1 standard comprises or consists of the amino acid sequence shown in SEQ ID NOS:7 or 8, and wherein the additional protein standard comprises or consists of the amino acid sequence shown in SEQ ID NOS: 23, 24, 9, 10, 20, 31, 32, 18, 19, 1, 2, 12, 36, 37, 27, 28, 25, or 26.

In further embodiments, provided herein are methods comprising: detecting, in a sample from a subject, the level of each of the HDL-associated proteins in at least one of Biomarker Panels 1-30, wherein the Biomarker Panels 1-26 are shown in Table 2, and wherein Biomarker Panels 27-30 are shown in Table 54. In certain embodiments, the subject is a human (e.g., a human male or human female). In certain embodiments, the human has been diagnosed as having cardiovascular disease.

In some embodiments, provided herein are systems and compositions comprising: a) a sample from a subject with, or suspected of having, cardiovascular disease; and b) a first component, wherein the first component comprises: i) an Apolipoprotein C3 (ApoC3) binding agent, and/or ii) a ApoC3 mass spectrometry standard.

In certain embodiments, the systems and compositions further comprise: c) a second component comprising a composition comprising detectably labeled HDL protein that can serve as a calibrator for normalizing signal in the sample to the approximate level of total HDL particles, ApoA1, or HDL-cholesterol present in the sample. In other embodiments, the detectably labeled HDL protein comprises labelled ApoA1 (e.g., isotope-labeled) protein or fragment thereof. In certain embodiments, the sample is selected from the group consisting of: a serum sample, a plasma sample, a blood sample, and a purified high-density lipoprotein (HDL) sample. In particular embodiments, the ApoC3 binding agent comprises an anti-ApoC3 antibody or binding portion thereof, or an anti-ApoC3 nucleic acid or protein aptamer or binding portion thereof. In certain embodiments, the ApoC3 mass spectrometry standard comprises an isotope-labeled or un-labelled ApoC3 protein or protein fragment. In further embodiments, the protein fragment comprises or consists of the amino acid sequence shown in SEQ ID NO:11.

In other embodiments, the systems or compositions further comprise: c) a second component comprising: i) a serum amyloid A 1/2 (SAA1/2) binding agent, and/or ii) a SAA1/2 mass spectrometry standard. In particular embodiments, the SAA1/2 binding agent comprises an anti-SAA1/2 antibody or binding portion thereof, or an anti-SAA1/2 nucleic acid or protein aptamer or binding portion thereof. In some embodiments, the SAA1/2 mass spectrometry standard comprises an labeled (e.g., isotope-labeled) or un-labelled SAA1/2 protein or protein fragment. In further embodiments, the protein fragment comprises or consists of the amino acid sequence shown in SEQ ID NO:35.

In additional embodiments, the systems or compositions further comprise: d) a third component comprising: i) a apolipoprotein A1 (ApoA1) binding agent, and/or ii) an ApoA1 mass spectrometry standard. In further embodiments, the ApoA1 binding agent comprises an anti-ApoA1 antibody or binding portion thereof, or an anti-ApoA1 nucleic acid or protein aptamer or binding portion thereof. In further embodiments, the ApoA1 mass spectrometry standard comprises an isotope-labeled or un-labelled ApoA1 protein or protein fragment. In certain embodiments, the protein fragment comprises or consists of the amino acid sequence shown in SEQ ID NOS:1 or 2.

In additional embodiments, the systems or compositions further comprise: d) a third component comprising: i) a apolipoprotein L1 (ApoL1) binding agent, and/or ii) an ApoL1 mass spectrometry standard; and e) a fourth component comprising: i) a phospholipid transfer protein (PLTP) binding agent, and/or ii) an PLTP mass spectrometry standard. In further embodiments, the ApoL1 binding agent comprises an anti-ApoA1 antibody or binding portion thereof, or an anti-ApoL1 nucleic acid or protein aptamer or binding portion thereof, and the PLTP binding agent comprises an anti-PLTP antibody or binding portion thereof, or an anti-PLTP nucleic acid or protein aptamer or binding portion thereof. In certain embodiments, the ApoL1 mass spectrometry standard comprises an isotope-labeled or un-labelled ApoL1 protein or protein fragment, and/or the PLTP mass spectrometry standard comprises an isotope-labeled or un-labelled PLTP protein or protein fragment. In further embodiments, the ApoL1 protein fragment comprises or consists of the amino acid sequence shown in SEQ ID NOS:18 or 19, and/or the PLTP protein fragment comprises or consists of the amino acid sequence shown in SEQ ID NOS:31 or 32.

In some embodiments, systems or compositions further comprise a fifth component comprising: i) an apolipoprotein E (ApoE) binding agent, and/or ii) an ApoE mass spectrometry standard. In other embodiments, the ApoE binding agent comprises an anti-ApoE antibody or binding portion thereof, or an anti-ApoE nucleic acid or protein aptamer or binding portion thereof. In additional embodiments, the ApoE mass spectrometry standard comprises an isotope-labeled or un-labelled ApoE protein or protein fragment. In other embodiments, the ApoE protein fragment comprises or consists of the amino acid sequence shown in SEQ ID NOS:15 or 16.

In certain embodiments, the systems and compositions further comprise: a sixth component comprising: i) an apolipoprotein A1 (ApoA1) binding agent, and/or ii) an ApoA1 mass spectrometry standard. In other embodiments, the systems further comprise: d) a third component comprising: i) a apolipoprotein M (ApoM) binding agent, and/or ii) an ApoM mass spectrometry standard; and e) a fourth component comprising: i) a phospholipid transfer protein (PLTP) binding agent, and/or ii) an PLTP mass spectrometry standard. In certain embodiments, the ApoM binding agent comprises an anti-ApoM antibody or binding portion thereof, or an anti-ApoM nucleic acid or protein aptamer or binding portion thereof. In particular embodiments, the ApoM mass spectrometry standard comprises an isotope-labeled or un-labelled ApoM protein or protein fragment. In other embodiments, the ApoM protein fragment comprises or consists of the amino acid sequence shown in SEQ ID NO: 20.

In additional embodiments, the systems and compositions further comprise: d) a third component comprising: i) a apolipoprotein C1 (ApoC1) binding agent, and/or ii) an ApoC1 mass spectrometry standard. In additional embodiments, the ApoC1 binding agent comprises an anti-ApoC1 antibody or binding portion thereof, or an anti-ApoC1 nucleic acid or protein aptamer or binding portion thereof. In other embodiments, the ApoC1 mass spectrometry standard comprises a labeled (e.g., isotope-labeled) or un-labelled ApoC1 protein or protein fragment. In certain embodiments, the ApoC1 protein fragment comprises or consists of the amino acid sequence shown in SEQ ID NOS: 7 or 8.

In other embodiments, the systems and compositions further comprise: d) a third component comprising: i) a apolipoprotein D (ApoD) binding agent, and/or ii) an ApoD mass spectrometry standard. In some embodiments, the ApoD binding agent comprises an anti-ApoD antibody or binding portion thereof, or an anti-ApoD nucleic acid or protein aptamer or binding portion thereof. In further embodiments, the ApoD mass spectrometry standard comprises a labeled (e.g., isotope-labeled) or un-labelled ApoD protein or protein fragment. In further embodiments, the ApoD protein fragment comprises or consists of the amino acid sequence shown in SEQ ID NOS: 13 or 14.

In certain embodiments, the systems an compositions further comprise: d) a fourth component comprising: i) an additional protein binding agent, and/or ii) an additional protein mass spectrometry standard, wherein the additional protein is selected from the group consisting of: CLU, ApoE, CETP, PON1, ApoC1, ApoA2, ApoC2, ApoM, PLTP, and ApoL1. In further embodiments, the additional protein binding agent comprises an anti-additional protein antibody or binding portion thereof, or an anti-additional protein nucleic acid or protein aptamer or binding portion thereof. In other embodiments, the additional protein mass spectrometry standard comprises an isotope-labeled or un-labelled additional protein or protein fragment. In other embodiments, the additional protein fragment comprises or consists of the amino acid sequence shown in SEQ ID NOS: 23, 24, 15, 16, 21, 22, 33, 34, 7, 8, 3, 4, 9, 10, 20, 31, 32, 18, and 19.

In some embodiments, the systems and compositions further comprise: c) a second component comprising: i) an ApoC1 binding agent, and/or ii) a ApoC1 mass spectrometry standard, and d) a third component comprising: i) an ApoC2 binding agent, and/or ii) a ApoC2 mass spectrometry standard. In further embodiments, the ApoC1 binding agent comprises an anti-ApoC1 antibody or binding portion thereof, or an anti-ApoC1 nucleic acid or protein aptamer or binding portion thereof; and wherein the ApoC2 binding agent comprises an anti-ApoC2 antibody or binding portion thereof, or an anti-ApoC2 nucleic acid or protein aptamer or binding portion thereof. In other embodiments, the ApoC1 mass spectrometry standard comprises an isotope-labeled or un-labelled ApoC1 protein or protein fragment, and wherein the ApoC2 mass spectrometry standard comprises an isotope-labeled or un-labelled ApoC2 protein or protein fragment.

In particular embodiments, the systems and compositions further comprise: d) a third component comprising: i) a apolipoprotein C1 (ApoC1) binding agent, and/or ii) an ApoC1 mass spectrometry standard, and e) a forth component comprising: i) an additional protein binding agent, and/or ii) an additional protein mass spectrometry standard, wherein the additional protein is selected from the group consisting of: ApoM, ApoA1, ApoC2, ApoC4, CLU, SAA4, ApoL1, HP, C3 and PLTP. In other embodiments, the ApoC1 binding agent comprises an anti-ApoC1 antibody or binding portion thereof, or an anti-ApoC1 nucleic acid or protein aptamer or binding portion thereof, and wherein the additional protein binding agent comprises an anti-additional protein antibody or binding portion thereof, or an anti-additional protein nucleic acid or protein aptamer or binding portion thereof. In some embodiments, the ApoC1 mass spectrometry standard comprises an isotope-labeled or un-labelled ApoC1 protein or protein fragment, and wherein the additional protein mass spectrometry standard comprises an isotope-labeled or un-labelled additional protein or protein fragment. In further embodiments, the ApoC1 protein fragment comprises or consists of the amino acid sequence shown in SEQ ID NOS: 7 or 8, and wherein the additional protein fragment comprises or consists of the amino acid sequence shown in SEQ ID NOS: 23, 24, 9, 10, 20, 31, 32, 18, 19, 1, 2, 12, 36, 37, 27, 28, 25, or 26. In particular embodiments, the subject is a human. In certain embodiments, the human has been diagnosed as having cardiovascular disease.

In some embodiments, provided herein are methods of determining the approximate risk of cardiovascular disease (e.g., CAD, atherosclerotic disease, etc.) and/or approximate reverse cholesterol transport capacity comprising: a) detecting, in a sample from a subject, the level of each of the HDL-associated proteins in at least one of Biomarker Panels 1-30, wherein the Biomarker Panels 1-26 are shown in Table 2, and wherein Biomarker Panels 27-30 are shown in Table 54; and b) determining the approximate risk of cardiovascular disease (CVD) for the subject, and/or the approximate cholesterol efflux capacity (CEC) of the sample.

In some embodiments, the sample is selected from the group consisting of: a serum sample, a plasma sample, a blood sample, and a purified high-density lipoprotein (HDL) sample. In further embodiments, the determining comprises employing a first algorithm to generate a cardiovascular disease (CVD) risk score or cholesterol efflux capacity (CEC) score, wherein the first algorithm performs operations comprising: i) multiplying each HDL-associated protein level by a predetermined coefficient to generate multiplied values, and ii) adding the multiplied values together, plus a panel-specific constant value, thereby generating the CVD risk score or the CEC score. In other embodiments, the methods further comprise: c) generating a report that provides the CVD risk score and/or the CEC score. In certain embodiments, the report further comprises at least one of the HDL-associated protein levels. In other embodiments, the determining further comprises employing a second algorithm to generate CVD probability, wherein the second algorithm applies the CVD risk score to the following formula: CVD probability=$1/(1+\exp(-\text{risk score}))$ or similar formula. In other embodiments, the methods further comprise: c) generating a report that provides the CVD (e.g., CAD) probability. In further embodiments, the report further comprises at least one of the HDL-associated protein levels.

In certain embodiments, the Biomarker Panel is selected from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In some embodiments, the Biomarker Panel is Biomarker Panel number 18, which is composed of HDL-associated proteins ApoA1, ApoC1, ApoC2, ApoC3, and ApoC4. In other embodiments, the Biomarker Panel is Biomarker Panel number 19, which is composed of HDL-associated proteins ApoA2, ApoC1, ApoC2, ApoC3, ApoD, and SAA1/2. In other embodiments, the Biomarker Panel is Biomarker Panel number 5, which is composed of HDL-associated proteins ApoA1, ApoC2, and ApoC3. In additional embodiments, the Biomarker Panel is Biomarker Panel number 4, which is composed of HDL-associated proteins ApoC1, ApoC3, CLU, PLTP, and SAA4. In other embodiments, the Biomarker Panel is Biomarker Panel number 28, which is composed of HDL-associated proteins ApoA1, ApoA2, ApoC1, ApoC2, ApoC3, ApoC4, ApoD, ApoE, ApoL1, ApoM, C3, CLU, HP, SAA1/2, and SAA4. In further embodiments, the Biomarker Panel is Biomarker Panel number 30, which is composed of HDL-associated proteins ApoA1, ApoA2, ApoC3, ApoC4, ApoD, ApoE, ApoL1, ApoM, C3, HP, PLTP, PON1, and SAA1/2. In some embodiments, the CVD is coronary artery disease (CAD). In further embodiments, the CEC is global CEC. In further embodiments, the CEC is ABCA1 CEC.

In some embodiments, the methods further comprise, after step a), but before step b), the step of normalizing the level of each of the HDL-associated proteins in the at least one Biomarker panel, wherein the normalizing is to the approximate level of total HDL particles or ApoA1 or HDL-cholesterol in the sample to generate normalized HDL protein values. In additional embodiments, the methods further comprising: determining the approximate level of total HDL particles or ApoA1 or HDL-cholesterol in the sample. In further embodiments, the determining the approximate level of total HDL particles or ApoA1 or HDL-cholesterol in the sample comprises determining the level of an internal standard added to the sample, wherein the internal standard comprises a labeled HDL protein.

In some embodiments, the detecting the level of each of the HDL-associated proteins in at least one of the Biomarker Panels comprises performing an assay on a least a portion of the sample that detects each of the HDL-associated protein, or fragments thereof, in the Biomarker Panel. In particular embodiments, the assay is a mass spectrometry or immunoassay. In further embodiments, the detecting the level of each of the HDL-associated proteins in at least one of the Biomarker Panels further comprises adding a labeled or un-labelled protein fragment standard to the sample corresponding to at least one of the detected HDL-associated proteins, and detecting the standard. In other embodiments, the subject is a human. In further embodiments, the human has been diagnosed as having cardiovascular disease.

In other embodiments, provided herein are systems and compositions comprising: a) a sample from a subject with, or suspected of having, cardiovascular disease; and b) at least one of the following: i) a binding agent for each of the HDL-associated proteins in at least one of Biomarker Panels 1-30, wherein the Biomarker Panels 1-26 are shown in Table 2, and wherein Biomarker Panels 27-30 are shown in Table 54; and/or ii) a mass spectrometry standard protein for each of the HDL-associated protein in at least one of Biomarker Panels 1-30.

In particular embodiments, the systems further comprise: c) a report that provides the raw or normalized levels of the HDL-associated proteins in the sample for at least one of the Biomarker panels. In further embodiments, the systems further comprise: c) a report that provides the CVD risk score and/or cholesterol efflux capacity (CEC) for the subject based the levels of the HDL-associated proteins in the sample for at least one of the Biomarker panels. In other embodiments, the systems further comprise: c) a report that provides the CVD probability risk for the subject. In particular embodiments, the subject is a human.

In some embodiments, provided herein are methods for reporting a CVD risk score or a cholesterol efflux capacity score for a subject comprising: a) obtaining subject values for each of the HDL-associated proteins in at least one of Biomarker Panels 1-30, wherein Biomarker Panels 1-26 are shown in Table 2, and wherein Biomarker Panels 27-30 are shown in Table 54, b) processing the subject values with a processing system such that a CVD risk score and/or a cholesterol efflux capacity score is determined for the subject, wherein the processing system comprises: i) a computer processor, and ii) non-transitory computer memory comprising one or more computer programs and a database, wherein the one or more computer programs comprise: a Biomarker Panel Model algorithm, and wherein the database comprises: i) a predetermined coefficient for each of the HDL-associated proteins in the at least one Biomarker Panel, and ii) a panel-specific constant value for the at least one Biomarker Panel; wherein the one or more computer programs, in conjunction with the computer processor, is/are configured to apply the Biomarker Panel Model algorithm to: i) multiply the level of each of the HDL-associated proteins in the at least one Biomarker Panel by the corresponding predetermined coefficient to generate multiplied values, and ii) add the multiplied values together, plus the panel-specific constant value, thereby generating a CVD risk score or cholesterol efflux capacity (CEC) score for the subject.

In certain embodiments, the methods further comprise: c) reporting the CVD risk score and/or the CEC score for the subject determined by the processing system. In some embodiments, the CVD risk score is employed to determine a probability of CVD risk for the subject. In further embodiments, methods further comprise: d) performing one or more of the following actions: i) performing coronary catheterization on the subject based on the probability of CVD risk being high, ii) treating the subject with a cardiovascular disease (CVD) therapeutic (e.g., a statin, an ACE inhibitor, an aldosterone inhibitor, an angiotensin II receptor blocker, a beta-blocker, a calcium channel blockers, a cholesterol-lowering drug, Digoxin, a Diuretic, potassium, magnesium, a vasodilator, or Warfarin) based on the probability of CVD risk being high or moderate, iii) prescribing the subject a CVD therapeutic based on the probability of CVD risk being high or moderate, iv) performing at least one additional diagnostic test on the subject based on the probability of CVD risk being moderate or high, v) admitting and/or directing the subject to be admitted to a hospital based on the probability of CVD risk being high, vi) testing a sample from the subject with one or more non-Biomarker Panel CVD risk assays based on the probability of CVD risk being moderate or high, vii) discharging the subject from a treatment facility based on the probability of CVD risk being low, and viii) performing a stress test on the subject based on the probability of CVD risk being moderate or high.

In certain embodiments, the methods further comprise: d) performing one or more of the following actions: i) communicating the probability of CVD risk for the subject to a user, ii) displaying the probability of CVD risk for the subject, iii) generating a report providing the probability of CVD risk for the subject, and iv) preparing and/or transmitting a report providing the probability of CVD risk for the subject. In other embodiments, the obtaining subject values comprises receiving the subject values from a testing lab, from the subject, from an analytical testing system, and/or from a hand-held or point of care testing device. In some embodiments, the processing system further comprises the analytical testing system and/or the hand-held or point of care testing device.

In particular embodiments, the obtaining subject values comprises electronically receiving the subject values. In other embodiments, the obtaining subject values comprises testing a sample from the subject with a detection assay. In further embodiments, the detection assay comprises an immunoassay or a mass spectrometry assay. In additional embodiments, the processing system further comprises a graphical user interface, and the method further comprises inputting the subject values via the graphical user interface. In certain embodiments, the graphical user interface is part of a device selected from: a desktop computer, a notebook computer, a tablet computer, a smart phone, and a point of care analytical device.

In additional embodiments, the processing system further comprises a sample analyzer. In further embodiments, at least part of the computer memory is located inside the sample analyzer. In further embodiments, the processing system further comprises a Laboratory Interface System (LIM). In other embodiments, at least part of the computer memory is part of the LIM.

In some embodiments, the processing system further comprises a processing device selected from the group consisting of: a desktop computer, a notebook computer, a tablet computer, a smart phone, and a point of care analytical device. In additional embodiments, at least part of the computer memory is located inside the processing device.

In other embodiments, the one or more computer programs further comprise a CVD probability algorithm, and wherein the one or more computer programs, in conjunction with the computer processor, is/are further configured to apply the CVD probability algorithm to: iii) apply the CVD risk score to the following formula: CVD probability=$1/(1+\exp(-\text{CVD risk score}))$. In particular embodiments, the CVD is coronary artery disease (CAD). In other embodiments, the CEC is global CEC. In some embodiments, the CEC is ABCA1 CEC.

In additional embodiments, the subject values for each of the HDL-associated proteins are normalized levels (e.g., with respect to the approximate level of total HDL particles or ApoA1 or HDL-cholesterol in the sample, or some other protein in the sample, such as HSA). In further embodiments, the at least one Biomarker Panel is Biomarker Panel number 18, which is composed of HDL-associated proteins ApoA1, ApoC1, ApoC2, ApoC3, and ApoC4. In other embodiments, the at least one Biomarker Panel is Biomarker Panel number 19, which is composed of HDL-associated proteins ApoA2, ApoC1, ApoC2, ApoC3, ApoD, and SAA1/2. In additional embodiments, the at least one Biomarker Panel is Biomarker Panel number 5, which is composed of HDL-associated proteins ApoA1, ApoC2, and ApoC3. In other embodiments, the at least one Biomarker Panel is Biomarker Panel number 4, which is composed of HDL-associated proteins ApoC1, ApoC3, CLU, PLTP, and SAA4. In further embodiments, the at least one Biomarker Panel is Biomarker Panel number 28, which is composed of HDL-associated proteins ApoA1, ApoA2, ApoC1, ApoC2, ApoC3, ApoC4, ApoD, ApoE, ApoL1, ApoM, C3, CLU, HP, SAA1/2, and SAA4. In other embodiments, the at least one Biomarker Panel is Biomarker Panel number 30, which is composed of HDL-associated proteins ApoA1, ApoA2, ApoC3, ApoC4, ApoD, ApoE, ApoL1, ApoM, C3, HP, PLTP, PON1, and SAA1/2. In further embodiments, the subject is a human. In other embodiments, the human has been diagnosed as having cardiovascular disease.

In further embodiments, provided herein are processing systems comprising: a) a computer processor, and b) non-transitory computer memory comprising one or more computer programs and a database, wherein the one or more computer programs comprise: a Biomarker Panel Model algorithm, and wherein the database comprises: i) subject values for each of the HDL-associated proteins in at least one of Biomarker Panels 1-30, wherein Biomarker Panels 1-26 are shown in Table 2, and wherein Biomarker Panels 27-30 are shown in Table 54, ii) a panel-specific predetermined coefficient for each of the HDL-associated proteins in the at least one of Biomarker Panels 1-30, and iii) a panel-specific constant value for the at least one Biomarker Panel; wherein the one or more computer programs, in conjunction with the computer processor, is/are configured to apply the Biomarker Panel Model algorithm to: i) multiply the subject values for each of the HDL-associated proteins by the corresponding panel-specific predetermined coefficient to generate multiplied values, and ii) add the multiplied values together, plus the panel-specific constant value, thereby generating a CVD risk score or cholesterol efflux capacity (CEC) score for the subject.

In certain embodiments, the one or more computer programs further comprise a CVD probability algorithm, and wherein the one or more computer programs, in conjunction with the computer processor, is/are further configured to apply the CVD probability algorithm to: iii) apply the CVD risk score to the following formula: CVD probability=$1/(1+\exp(-\text{CVD risk score}))$. In some embodiments, the CVD is coronary artery disease (CAD). In further embodiments, the CEC is global CEC. In other embodiments, the CEC is ABCA1 CEC.

In certain embodiments, the subject values for each of the HDL-associated proteins are normalized levels with respect to the approximate level of total HDL particles or ApoA1 or HDL-cholesterol in the sample. In other embodiments, systems further comprise: c) an HDL-associated protein analytical testing system and/or a hand-held or point of care HDL-associated protein point of care testing device. In particular embodiments, the HDL-associated protein analytical testing system comprises a mass spectrometer or an optical detector. In other embodiments, the systems further comprise: c) a graphical user interface for inputting the subject values for each of the HDL-associated proteins into the computer memory. In other embodiments, the graphical user interface is part of a device selected from: a desktop computer, a notebook computer, a tablet computer, a smart phone, and a point of care analytical device.

In some embodiments, the systems further comprise a sample analyzer, wherein at least part of the computer memory is located inside the sample analyzer. In particular embodiments, the systems further comprise at least part of a Laboratory Interface System (LIM). In other embodiments, at least part of the computer memory is part of the LIM. In other embodiments, the systems further comprise: c) a processing device selected from the group consisting of: a desktop computer, a notebook computer, a tablet computer, a smart phone, and a point of care analytical device. In other embodiments, at least part of the computer memory is located inside the processing device. In additional embodiments, the systems further comprise a display component configured to display the CVD risk score or the CEC score for the patient. In other embodiments, the display component is selected from a computer monitor, a tablet computer screen, a smart phone screen, and a point of care analytical device screen.

In some embodiments, the at least one Biomarker Panel is Biomarker Panel number 18, which is composed of HDL-associated proteins ApoA1, ApoC1, ApoC2, ApoC3, and ApoC4. In further embodiments, the at least one Biomarker Panel is Biomarker Panel number 19, which is composed of HDL-associated proteins ApoA2, ApoC1, ApoC2, ApoC3, ApoD, and SAA1/2. In other embodiments, the at least one Biomarker Panel is Biomarker Panel number 5, which is composed of HDL-associated proteins ApoA1, ApoC2, and ApoC3. In further embodiments, the at least one Biomarker Panel is Biomarker Panel number 4, which is composed of HDL-associated proteins ApoC1, ApoC3, CLU, PLTP, and SAA4. In some embodiments, the at least one Biomarker Panel is Biomarker Panel number 28, which is composed of HDL-associated proteins ApoA1, ApoA2, ApoC1, ApoC2, ApoC3, ApoC4, ApoD, ApoE, ApoL1, ApoM, C3, CLU, HP, SAA1/2, and SAA4. In particular embodiments, the at least one Biomarker Panel is Biomarker Panel number 30, which is composed of HDL-associated proteins ApoA1, ApoA2, ApoC3, ApoC4, ApoD, ApoE, ApoL1, ApoM, C3, HP, PLTP, PON1, and SAA1/2. In other embodiments, the subject is a human. In additional embodiments, the human has been diagnosed as having cardiovascular disease.

In some embodiments, provided herein is non-transitory computer memory component comprising: one or more computer programs configured to access a database, wherein the one or more computer programs comprise: a Biomarker Panel Model algorithm, and wherein the database comprises: i) subject values for each of the HDL-associated proteins in at least one of Biomarker Panels 1-30, wherein Biomarker Panels 1-26 are shown in Table 2, and wherein Biomarker Panels 27-30 are shown in Table 54, ii) a predetermined coefficient for each of the HDL-associated proteins in the at least one of Biomarker Panels 1-30, and iii) a panel-specific constant value for the at least one Biomarker Panel; wherein the one or more computer programs, in conjunction with the computer processor, is/are configured to apply the Biomarker Panel Model algorithm to: i) multiply the subject values for each of the HDL-associated proteins by the corresponding predetermined coefficient to generate multiplied values, and ii) add the multiplied values together, plus the panel-specific constant value, thereby generating a CVD risk score or cholesterol efflux capacity (CEC) score for the subject.

In further embodiments, the assaying the HDL-associated proteins is performed with a technique selected from the group consisting of: mass spectrometry (MS), chromatography, LC-MS, plasmon resonance, and an assay comprising the use of polyvinyl sulfonic acid (PVS) and polyethyleneglycol-methyl ether (PEGME). In certain embodiments, the detecting is accomplished by injecting the purified HDL sample into a device that performs both chromatography and mass spectrometry. In some embodiments, the device is a liquid chromatography-mass spectrometry (LC/MS) machine.

In certain embodiments, the HDL values are normalized values. In particular embodiments, the normalization is with respect to total HDL cholesterol, or ApoA1 proteins, or HDL particles. Determination of total HDL can be performed by measuring HDL cholesterol, which is commonly performed using "homogenous" assays which use selected reagents added in specific order to "clear" the serum sample of LDL cholesterol particles containing the lipoprotein ApoB. Subsequently, the HDL cholesterol is chemically determined using traditional enzyme coupled assays. Measuring total HDL can also be performed utilizing physical methods of HDL particle isolation, typically ultracentrifugation (e.g., Warnick et al., Clinical Chemistry September 2001 vol. 47 no. 9 1579-1596, herein incorporated by reference). In some embodiments, the amount measured HDL-associated protein may be compared to the total amount of native ApoA1 in the initial sample in order to determine a ratio for normalization. ApoA1 is the primary lipoprotein component of each HDL particle. While determination of HDL cholesterol, rather than ApoA1, has been a mainstay of cardiovascular risk assessment this view is changing as the determination of ApoA1 has utility in identification of subclinical atherosclerosis (Florvall et al., Journal of Gerontology: BIOLOGICAL SCIENCES 2006, Vol. 61A, No. 12, 1262-1266, herein incorporated by reference). Total ApoA1 is typically measured using widely available immunoassay platform assays.

In some embodiments, provided herein are methods comprising: detecting the level of at least three (or at least two) HDL-associated proteins (e.g., selected from those listed in Tables 2 and 54) in a sample from a subject, and wherein the subject has, or is suspected of having, cardiovascular disease. In particular embodiments, the sample is a purified high-density lipoprotein sample.

In certain embodiments, provided herein are methods of determining the approximate risk of cardiovascular disease and/or approximate reverse cholesterol transport capacity comprising: a) detecting, in a sample from a subject, the level of at least three (or at least two) HDL-associated proteins (e.g., selected from those listed in Tables 2 and 54); and b) determining the approximate risk of cardiovascular disease (CVD) for the subject, and/or the approximate cholesterol efflux capacity (CEC) of the sample.

In some embodiments, provided herein are systems comprising: a) a sample from a subject with, or suspected of having, cardiovascular disease; and b) at least one of the following: i) a binding agent for each of at least three (or at least two) HDL-associated proteins (e.g., selected from those listed in Tables 2 and 54); and/or ii) a mass spectrometry standard protein for each of the at least three (or at least two) HDL-associated proteins.

In other embodiments, provided herein are methods for reporting a CVD risk score or a cholesterol efflux capacity score for a subject comprising: a) obtaining subject values for each of at least three (or at least two) HDL-associated proteins (e.g., selected from those listed in Tables 2 and 54), b) processing the subject values with a processing system such that a CVD risk score and/or a cholesterol efflux capacity score is determined for the subject, wherein the processing system comprises: i) a computer processor, and ii) non-transitory computer memory comprising one or more computer programs and a database, wherein the one or more computer programs comprise: a Biomarker algorithm, and wherein the database comprises: i) a predetermined coefficient for each of the at least three (or at least two) HDL-associated proteins, and ii) a panel-specific constant value for the combination of the at least three (or at least two) HDL-associated proteins; wherein the one or more computer programs, in conjunction with the computer processor, is/are configured to apply the Biomarker algorithm to: i) multiply the level of each of the at least three (or at least two) HDL-associated proteins by the corresponding predetermined coefficient to generate multiplied values, and ii) add the multiplied values together, plus the panel-specific constant value, thereby generating a CVD risk score or cholesterol efflux capacity (CEC) score for the subject.

In some embodiments, provided herein are processing systems comprising: a) a computer processor, and b) non-transitory computer memory comprising one or more computer programs and a database, wherein the one or more computer programs comprise: a Biomarker algorithm, and wherein the database comprises: i) subject values for each of at least three (or at least two) HDL-associated proteins (e.g., selected from those listed in Tables 2 and 54), ii) a panel-specific predetermined coefficient for each of the at least three (or at least two) HDL-associated proteins, and iii) a panel-specific constant value for the combination of the at least three HDL-associated proteins; wherein the one or more computer programs, in conjunction with the computer processor, is/are configured to apply the Biomarker algorithm to: i) multiply the subject values for each of the at least three (or at least two) HDL-associated proteins by the corresponding panel-specific predetermined coefficient to generate multiplied values, and ii) add the multiplied values together, plus the panel-specific constant value, thereby generating a CVD risk score or cholesterol efflux capacity (CEC) score for the subject.

In particular embodiments, provided herein are non-transitory computer memory component comprising: one or more computer programs configured to access a database, wherein the one or more computer programs comprise: a Biomarker algorithm, and wherein the database comprises: i) subject values for each of at least three (or at least two) HDL-associated proteins (e.g., selected from those listed in Tables 2 and 54), ii) a predetermined coefficient for each of the HDL-associated proteins, and iii) a panel-specific constant value for the combination of the at least three (at least two) HDL-associated proteins; wherein the one or more computer programs, in conjunction with the computer processor, is/are configured to apply the Biomarker algorithm to: i) multiply the subject values for each of the HDL-associated proteins by the corresponding predetermined coefficient to generate multiplied values, and ii) add the multiplied values together, plus the panel-specific constant value, thereby generating a CVD risk score or cholesterol efflux capacity (CEC) score for the subject.

In certain embodiments, the Biomarker Panels described herein are used to diagnose the risk of an HDL related disease selected from: cardiovascular disease, nonalcoholic steatohepatitis (NASH), lupus erythematosus, irritable bowel syndrome (IBS), chronic kidney disease (CKD), rheumatoid arthritis (RA), and Alzheimer's disease.

DEFINITIONS

Figure 1:
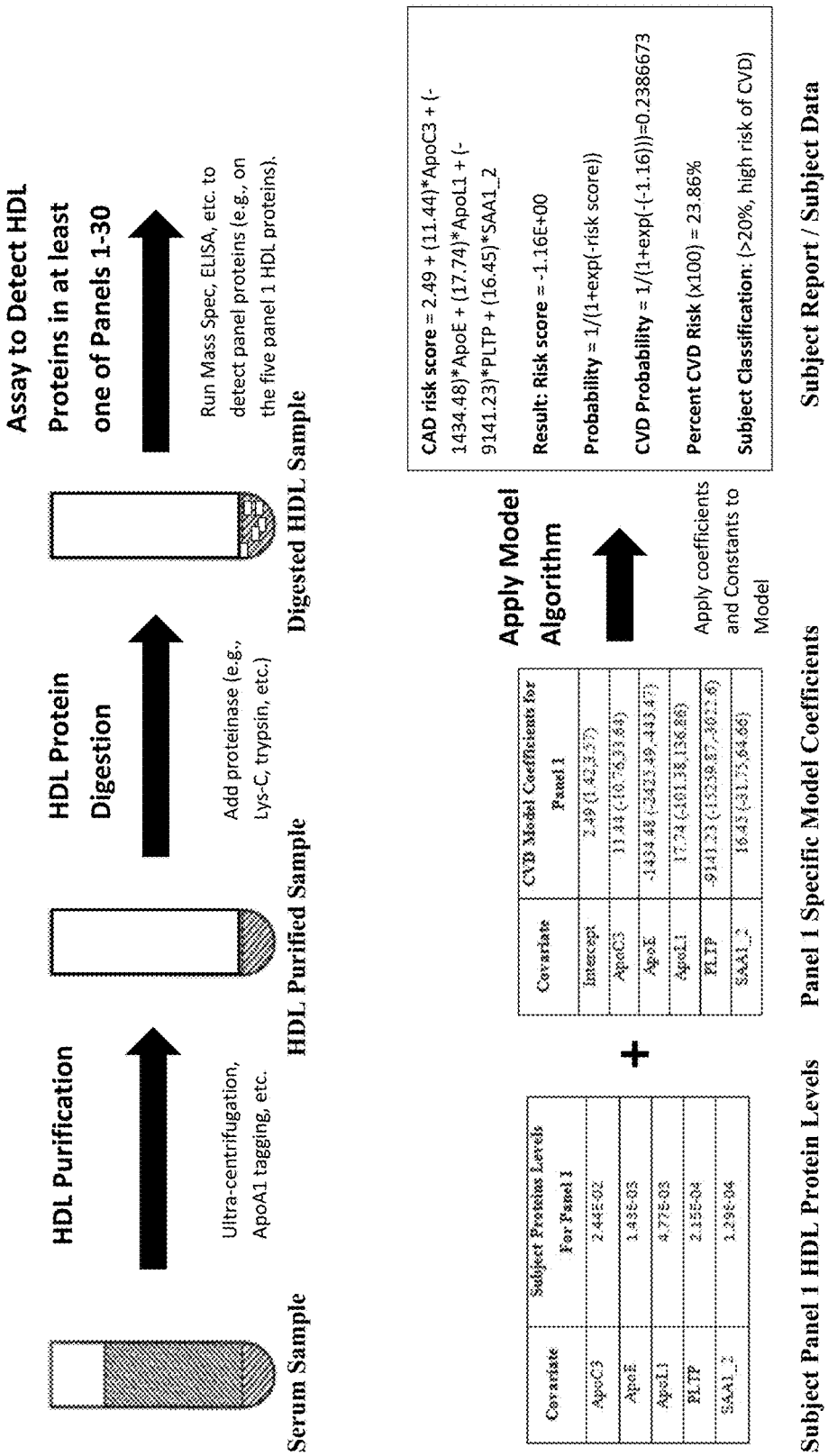
FIG. 1 shows an exemplary work flow, corresponding to the steps described in Example 1 below with respect to Panel 1.

As used herein, "high density lipoprotein" or "HDL" is a circulating, non-covalent assembly of amphipathic proteins that enable lipids like cholesterol and triglycerides to be transported within the water-based bloodstream. HDL is composed of about 50% by mass amphipathic proteins that stabilize lipid emulsions composed of a phospholipid monolayer (about 25%) embedded with free cholesterol (about 4%) and a core of triglycerides (about 3%) and cholesterol esters (about 12%). Subclasses of HDL include HDL2 and HDL3. HDL2 particles are larger and contain a higher content of lipid whereas HDL3 particles are smaller and contain less lipid. Further subclasses include from largest particle to smallest particle, HDL2b, HDL2a, HDL3a, HDL3b, and HDL3c.

As used herein, a "lipoprotein" refers to a type of protein to which one or more lipid molecules is attached or is capable of being attached. In some cases, a lipoprotein may be a "lipid-poor lipoprotein" in which four or fewer molecules of phospholipid are bound. As used herein, a lipoprotein includes a protein to which no lipid is attached but which can be exchanged in an HDL particle (e.g. an apolipoprotein).

As used herein, the phrase "reverse cholesterol transport" refers to the multi-step process resulting in the net movement of cholesterol from peripheral tissues back to the liver via the plasma.

As used herein, the phrase "cholesterol efflux capacity (CEC)" of a sample refers to the ability of HDL in a sample to promote reverse cholesterol transport by accepting cholesterol from lipid-laden macrophages. Methods of measuring CEC include, but are not limited to, those disclosed in de la Llera-Moya et al., Arterioscler Thromb Vasc Biol. 2010 April; 30(4):796-801; Sankaranarayanan et al., J Lipid Res. 2011 December; 52(12):2332-40; and Khera et al., NEJM, 364; 2, 2011, all of which are herein incorporated by reference in their entireties, and including for the assays they disclose. ABCA1 CEC specifically refers to reverse cholesterol transport driven specifically by the ABCA1 transporter, which can be measured, for example, by subtracting the difference in CEC between reagent-treated (e.g., cAMP treated) and reagent-untreated macrophages in which the macrophages have been modified such that ABCA1 expression is directly increased in the presence of the treatment reagent.

As used herein, "blood sample" refers to a whole blood sample or a plasma or serum fraction derived therefrom. In certain embodiment, a blood sample refers to a human blood sample such as whole blood or a plasma or serum fraction derived therefrom. In some embodiments, a blood sample refers to a non-human mammalian ("animal") blood sample such as whole blood or a plasma or serum fraction derived therefrom.

As used herein, the term "whole blood" refers to a blood sample that has not been fractionated and contains both cellular and fluid components.

As used herein, "plasma" refers to the fluid, non-cellular component of the whole blood. Depending on the separation method used, plasma may be completely free of cellular components, or may contain various amounts of platelets and/or a small amount of other cellular components. Because plasma includes various clotting factors such as fibrinogen, the term "plasma" is distinguished from "serum" as set forth below.

As used herein, the term "serum" refers to whole mammalian serum, such as, for example, whole human serum, whole serum derived from a test animal, whole serum derived from a pet, whole serum derived from livestock, etc. Further, as used herein, "serum" refers to blood plasma from which clotting factors (e.g., fibrinogen) have been removed.

As used herein, the phrase "purified high-density lipoprotein sample," refers to a blood sample (e.g., serum, or plasma, or whole blood sample), which has been purified (e.g., by ultra-centrifugation or ApoA1 exchanged methods described below) to generate a purified sample wherein at least 90% of all the proteins in the purified sample are HDL lipoproteins (e.g., at least 90% . . . 94% . . . 98% . . . 99% . . . or at least 99.9%). In some embodiments, less than 10% of all the proteins in the purified sample are non-HDL lipoproteins (e.g., less than 10% . . . 5% . . . 1% . . . 0.2%). In certain embodiments, the non-HDL lipoproteins are primarily or completely serum albumin.

As used herein, the terms "cardiovascular disease" (CVD) or "cardiovascular disorder" are terms used to classify numerous conditions affecting the heart, heart valves, and vasculature (e.g., veins and arteries) of the body and encompasses diseases and conditions including, but not limited to arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease.

As used herein, the phrase "suspected of having CVD" refers to a patient with at least one sign or symptom related to CVD, such as extreme fatigue, constant dizziness or lightheadedness, a fast heart rate (e.g., more than 100 beats per minute at rest), a new irregular heartbeat, chest pain or discomfort during activity that goes away with rest, difficulty breathing during regular activities and rest, a respiratory infection or cough that becomes worse, restlessness or confusion, changes in sleep patterns, and loss of appetite or nausea.

As used herein, the term "atherosclerotic cardiovascular disease" or "disorder" refers to a subset of cardiovascular disease that include atherosclerosis as a component or precursor to the particular type of cardiovascular disease and includes, without limitation, CAD, PAD, cerebrovascular disease. Atherosclerosis is a chronic inflammatory response that occurs in the walls of arterial blood vessels. It involves the formation of atheromatous plaques that can lead to narrowing ("stenosis") of the artery, and can eventually lead to partial or complete closure of the arterial opening and/or plaque ruptures. Thus, atherosclerotic diseases or disorders include the consequences of atheromatous plaque formation and rupture including, without limitation, stenosis or narrowing of arteries, heart failure, aneurysm formation including aortic aneurysm, aortic dissection, and ischemic events such as myocardial infarction and stroke. In certain embodiments, the methods, compositions, and systems disclosed here are used to at least partially diagnose atherosclerotic CVD.

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

DETAILED DESCRIPTION

Provided herein are methods, systems, and compositions for detecting one or more HDL-associated proteins (e.g., ApoC3; ApoC3 and ApoA1; ApoC3 and SAA1/2; or proteins in Biomarker Panels 1-30) in a sample from a subject with, or suspected of having, cardiovascular disease (CVD) or other HDL related disease. In certain embodiments, such methods, systems, and compositions are used to determine the approximate risk of CVD (or other disease) for a subject, and/or the approximate cholesterol efflux capacity (CEC) of a sample. In particular embodiments, the systems and compositions are composed of a sample from a subject with, or suspected of having CVD, and an HDL-associated binding agent or mass spectrometry standard.

Provided herein a methods, compositions, and kits for determining predicting cardiovascular disease and/or cholesterol efflux based on measuring the levels of proteins in one or more of the Panels shown in Tables 2 and 54 below. Work conducted during the development of embodiments of the present disclosure found that either single protein levels (e.g., ApoC3, which is Panel 10) or combination of proteins (e.g., panels 1-9 and 11-30) find use for CVD and cholesterol efflux potential determinations. Described below are exemplary, non-limiting, methods and systems that are employed using the biomarker panels on samples from subjects with, or suspected of having, cardiovascular disease.

In some embodiments, initially, a subject with symptoms of cardiovascular disease (e.g., chest pain) will have their blood drawn at a hospital, clinic or other medical facility. This blood sample is treated to generate a serum sample. The serum sample is then treated with a method to purifying the HDL in the sample, such as by ultra-centrifugation or tagged HDL binding particle purification. This purified serum sample is then treated with an enzyme (e.g., such as Lys-C) that digests the HDL-associated proteins present in the purified sample. This digested sample is then subjected to one or more detection assays (e.g., mass spectrometry, an immunological assay, aptamer binding assay), to detect the HDL-associated protein levels found in one or more of Biomarker Panels 1-30.

In some embodiments, if mass spectrometry is employed, the detection protocol may be as follows. A portion of the digested HDL purified sample is diluted and loaded onto the LC column Peptides are then detected using a triple quadrupole mass spectrometer (e.g., operating in dynamic MRM mode). Peptides are targeted with pre-determined "transitions" constituting of predetermined m/z values for the intact peptide mass (filtered in Q1 of the instrument), a collision energy which the intact peptide is subjected to in q2 of the instrument, and a fragment (m/z) value for a peptide fragment (filtered in Q3). Transitions are selected to be unique to the peptide targeted within the sample. Two transitions (a "quantifier" used for later quantification and a "qualifier" used for quality control) are monitored per peptide, and up to two peptides are targeted per protein. A detailed list of peptide targets and their transitions is shown in Example 1 below in Table 1.

Peptide signal intensities are obtained by integrating the chromatographic peak for each peptide's "quantifier" transition. Proteins intensity is determined by summing the quantifier peak areas of each of the protein's targeted peptides and normalizing to the intensity of one or more HDL-associated proteins.

The levels of the HDL-associated proteins for the selected Biomarker Panel are then processed with a multivariate algorithm to determine cholesterol efflux or CVD risk score. The algorithm includes a constant (i) specific to each panel (and specific to CVD risk score or global or ABCA1 efflux), and protein and panel specific coefficients (c) that are multiplied by the specific protein level detected. The algorithm is as follows:

$$\text{CVD Risk Score/Predicted global cholesterol efflux} = c_1 {}^* p_1 + c_2 {}^* p_2 \ldots c_n {}^* p_n + i$$

where efflux or CVD risk is determined by the additive combination of a coefficient (c) multiplied by the protein level for a given protein (p) (e.g., normalized peak area) plus a constant (i). Example 1 below provides the coefficients and constants for each protein for each panel, for both mass spec determined protein values and moral protein values. Example 1 further provides the 95% confidence range for each of these numbers. One may, for example, use a value anywhere in this range for the value of (c) or (p) when calculating a CVD risk score and/or a cholesterol efflux value.

The determined CVD risk score using the above algorithm and values in Example 1 below may be converted into a probability (percent risk of CVD) using the following formula:

$$\text{Probability} = 1/(1 + \exp(-\text{risk score})).$$

This probability value can then be multiplied by 100 to give a percent risk of CVD. The risk score or probability or percent risk of CVD may be employed by health care personnel as an aid in deciding on treatment of patients suspected of having heart disease or for ruling patients out as in need of treatment or monitoring. For example, in general, a patient that has a percent risk of CAD of less than 10% is usually considered as low risk (e.g., patient may be considered as not in need of treatment or monitoring for heart disease), a patient with a percent risk of CAD of between 10-20% risk is usually considered as intermediate risk (e.g., patient may be monitored for additional signs of heart diseae), a patient with a percent risk of CAD of greater than 20% is usually considered at high risk (e.g., may be treated right away with therapeutics or surgical intervention).

In certain embodiments, the protein or proteins that are detected as part of Panels 1-30 are detected in purified high-density lipoprotein sample. Purified HDL sample can be generated by any suitable method, including ultra-centrifugation or HDL-binding peptide method.

For ultra-centrifugation, for example, one could employ ultracentrifugation of serum (105,000×g) at a density of 1.006 kg/L for 18 hours at 18° C. to remove the very low-density lipoproteins that interfere with the precipitation of low-density lipoproteins with manganese and heparin. Manganese chloride and heparin are added to the bottom fraction in amounts sufficient to obtain final concentrations of 0.0456 mol $Mn^{2+}$ and 183 UPS kU/L of heparin, which will precipitate non-HDL-C lipoproteins. After centrifugation at 1500×g for 30 minutes at 4° C., the resulting supernatant is then adjusted to a density of ≥1.21 kg/L using potassium bromide. The density adjusted solution is then centrifuged for a second time (~105,000×g) for 24 hours. After centrifugation, the uppermost layer can be carefully removed to yield an HDL rich fraction.

In certain embodiments, HDL is purified using HDL binding peptides (e.g., ApoA1) that have been affinity tagged. Such methods of purification are described in U.S. application Ser. No. 14/713,046, filed May 15, 2015, which is herein incorporated by reference in its entirety as if fully set forth herein. Briefly, HDL binding peptides (e.g., ApoA1) that have been affinity tagged are introduced into a sample. HDL particles incorporate some of the binding particles. Such HDL particles are then purified using the affinity tag, thereby generating a purified HDL sample.

The present invention is not limited by the methods used to detect the HDL-associated peptides (e.g., ApoC3, SAA1/2, ApoE, ApoL1, etc.) from a subject sample.

In certain embodiments, the HDL-associated proteins are detected with a detection methods selected from the following: an immunoassay, surface plasmon resonance, an in vitro assay, an activity assay, co-immunoprecipitation assay, mass spectrometry, Fluorescence Energy Transfer (FRET), bioluminescence energy transfer (BRET), interferometry, Bio-layer Interferometry (BLI), Dual Polarization Interferometry ("DPI"), Ellipsometry, and Quartz Crystal Microbalance.

EXAMPLES

Example 1

This example describes testing 26 panels of single and multiple HDL proteins for their ability to predict global cholesterol efflux and cardiovascular disease risk using various global cholesterol efflux and coronary artery disease risk algorithms. The HDL proteins were measured by mass spectrometry.

HDL Purification

The following protocol was used for purifying HDL. 12 µL of human serum is combined with 25 µL of a 0.5 mg/mL solution of $^{15}$N-labeled His-tagged Apolipoprotein A-I in 1× Phosphate Buffered Saline (PBS) pH 7.4. The serum—ApoA-I mixture is incubated at 37° C. for 15 minutes, during which the His-tagged ApoA-I is incorporated into HDL particles in the serum sample. The HDL is then purified from the mixture by immobilized metal affinity chromatography in a pipet tip format that is amenable to high through-put automated liquid handling platforms. Briefly, the serum-ApoA-I mixture is diluted to 200 µL with the addition of 164

µL of binding buffer (5 mM imidazole, 50 mM sodium phosphate, 300 mM sodium chloride, pH 8.0). The affinity column tips are equilibrated with 400 µL of binding buffer. The affinity columns are then used to aspirate and dispense 180 µL of the serum/ApoA-I mixture over the column bed 6 times at a flow rate of 200 µL/minute. The column bed is then washed once by aspirating and dispensing 200 µL of binding buffer, followed by a second wash with 200 µL of a strong wash buffer (10 mM imidazole, 50 mM sodium phosphate, 300 mM sodium chloride, pH 8.0). The bound HDL particles are then eluted by aspirating and dispensing 90 µL of elution buffer (300 mM Imidazole, 50 mM Tris-HCl, 25% Methanol, pH 9.0).

HDL Digestion

5 µL of 100 mM dithiothreitol, and 10 µL of 50 ng/µL Endoproteinase Lys-C are then added to the eluted HDL and incubated at 37° C. for 4 hours. The Lys-C cleaves HDL associated proteins at the C-terminal side of lysine amino acid residues in their sequences, producing predictable target peptides for LC-MS analysis and quantification.

LC-MS Analysis of HDL Proteome Target Peptides

25 µL of Lys-C digested HDL in elution buffer containing 25% methanol is injected and diluted five-fold, in-line, using a mixing tee before being loaded directly onto the LC column. The dilution and loading is accomplished using a sample loading pump with 0.1% formic acid in water operating at 150 µL/minute into a mixing-tee, and a binary pump with 99% mobile phase A (0.1% formic acid in water), 1% mobile phase B (0.1% formic acid in acetonitrile) operating at 600 µL/minute into the tee. After loading, the binary pump is diverted directly in-line with the column and the peptides are eluted across a 5 minute linear gradient from 1% to 65% mobile phase B at 500 µL/min. Peptides are detected using an Agilent 6490 triple quadrupole mass spectrometer operating in dynamic MRM mode. Dynamic MRM allows to the targeted detection and quantification of peptide targets within a scheduled retention time window. Peptides are targeted with pre-determined "transitions" constituting of predetermined m/z values for the intact peptide mass (filtered in Q1 of the instrument), a collision energy which the intact peptide is subjected to in q2 of the instrument, and a fragment (m/z) value for a peptide fragment (filtered in Q3). Transitions are selected to be unique to the peptide targeted within the sample. Two transitions (a "quantifier" used for later quantification and a "qualifier" used for quality control) are monitored per peptide, and up to two peptides are targeted per protein. A detailed list of peptide targets and their transitions is shown in Table 1. It is noted that other portions, besides the recited peptide sequences, could be used to make the mass spectrometry measurements.

TABLE 1

List of target proteins with signature peptides and transitions

| Protein Name | UniProt Accession Number | Peptide Sequence | Precursor Ion m/z (Q1) | Product Ion m/z (Q3) |
| --- | --- | --- | --- | --- |
| Apolipoprotein A-I | P02647 | ATEHLSTLSEK (SEQ ID NO: 1) | 405.88 | 572.80 |
| | | | 405.88 | 522.27 |
| | | LLDNVVDSVTSTFSK (SEQ ID NO: 2) | 538.27 | 569.29 |
| | | | 538.27 | 856.44 |
| Apolipoprotein A-II | P02652 | EQLTPLIK (SEQ ID NO: 3) | 471.29 | 470.33 |
| | | | 471.29 | 571.38 |
| | | SPELQAEAK (SEQ ID NO: 4) | 486.75 | 659.37 |
| | | | 486.75 | 788.41 |
| Apolipoprotein A-IV | P06727 | LVPFATELHERLAK (SEQ ID NO: 5) | 541.98 | 706.39 |
| | | | 541.98 | 1096.61 |
| | | VNSFFSTFK (SEQ ID NO: 6) | 538.77 | 776.40 |
| | | | 538.77 | 863.43 |
| Apolipoprotein C-I | P02654 | ARELISRIK (SEQ ID NO: 7) | 362.56 | 470.29 |
| | | | 362.56 | 503.33 |
| | | QSELSAK (SEQ ID NO: 8) | 381.70 | 305.18 |
| | | | 381.70 | 418.27 |
| Apolipoprotein C-II | P02655 | ESLSSYWESAK (SEQ ID NO: 9) | 643.80 | 957.43 |
| | | | 643.80 | 870.40 |
| | | TYLPAVDEK (SEQ ID NO: 10) | 518.27 | 658.34 |
| | | | 518.27 | 771.42 |
| Apolipoprotein C-III | P02656 | DYWSTVK (SEQ ID NO: 11) | 449.72 | 434.26 |
| | | | 449.72 | 620.34 |
| Apolipoprotein C-IV | P55056 | AWFLESK (SEQ ID NO: 12) | 440.73 | 476.27 |
| | | | 440.73 | 623.34 |
| Apolipoprotein D | P05090 | NILTSNNIDVK (SEQ ID NO: 13) | 615.84 | 890.46 |
| | | | 615.84 | 1003.54 |
| | | YLGRWYEIEK (SEQ ID NO: 14) | 452.90 | 540.78 |
| | | | 452.90 | 597.32 |
| Apolipoprotein E | P02649 | LEEQAQQIRLQAEAFQARLK (SEQ ID NO: 15) | 790.77 | 936.03 |
| | | | 790.77 | 900.52 |
| | | SELEEQLTPVAEETRARLSK (SEQ ID NO: 16) | 762.74 | 849.98 |
| | | | 762.74 | 979.02 |

TABLE 1-continued

List of target proteins with signature peptides and transitions

| Protein Name | UniProt Accession Number | Peptide Sequence | Precursor Ion m/z (Q1) | Product Ion m/z (Q3) |
|---|---|---|---|---|
| Apolipoprotein F | Q13790 | DANISQPETTK (SEQ ID NO: 17) | 602.30 602.30 | 575.30 790.39 |
| Apolipoprotein L1 | O14791 | LNILNNNYK (SEQ ID NO: 18) WWTQAQAHDLVIK (SEQ ID NO: 19) | 553.30 553.30 532.62 532.62 | 765.39 652.30 612.34 724.44 |
| Apolipoprotein M | O95445 | EFPEVHLGQWYFIAGAAPTK (SEQ ID NO: 20) | 754.38 754.38 | 544.31 615.35 |
| Cholestetyl Ester Transfer Protein (CETP) | P11597 | LFLSLLDFQITPK (SEQ ID NO: 21) PALLVLNHETAK (SEQ ID NO: 22) | 767.95 767.95 435.92 435.92 | 848.45 1161.65 812.43 911.49 |
| Clusterin (CLU) | P10909 | EIQNAVNGVK (SEQ ID NO: 23) LFDSDPITVTVPVEVSRK (SEQ ID NO: 24) | 536.29 536.29 668.03 668.03 | 701.39 417.25 712.93 814.48 |
| Complement C3 | P01024 | AFSDRNTLIIYLDK (SEQ ID NO: 25) TGLQEVEVK (SEQ ID NO: 26) | 556.97 556.97 501.78 501.78 | 725.90 764.46 731.39 844.48 |
| Haptoglobin (HP) | P00738 | DIAPTLTLYVGK (SEQ ID NO: 27) VTSIQDWVQK (SEQ ID NO: 28) | 645.87 645.87 602.32 602.32 | 496.29 991.58 1003.52 916.49 |
| Phosphatidylcholine-sterol acyltransferase (LCAT) | P04180 | DRFIDGFISLGAPQGGSIK (SEQ ID NO: 29) TYSVEYLDSSK (SEQ ID NO: 30) | 679.36 679.36 646.31 646.31 | 872.46 744.40 841.39 1027.49 |
| Phospholipid Transfer Protein (PLTP) | P55058 | GLREVIEK (SEQ ID NO: 31) QEGLRFLEQELETITIPDLRGK (SEQ ED NO: 32) | 472.28 472.28 862.47 862.47 | 555.32 668.41 685.40 473.32 |
| Serum Paraoxonase/atylesterase 1 (PON1) | P27169 | SFNPNSPGK (SEQ ID NO: 33) YVYIAELLAHK (SEQ ID NO: 34) | 474.23 474.23 440.58 440.58 | 599.31 713.36 529.31 781.46 |
| Serum Amyloid A (SAA) 1/2 | P0DJI8/P0DJI9 | YFHARGNYDAAK (SEQ ID NO: 35) | 471.56 471.56 | 551.77 483.24 |
| Serum Amyloid A (SAA) 4 | P35542 | AEEWGRSGK (SEQ ID NO: 36) DPDRFRPDGLPK (SEQ ID NO: 37) | 340.50 340.50 471.58 471.58 | 474.73 504.29 585.29 543.31 |

The 26 Panels of HDL Proteins

Shown in Table 2 are the 26 Panels of combinations of proteins that provided good results for measuring HDL global cholesterol efflux.

TABLE 2

| Panel No. | Panel Size | Proteins |
|---|---|---|
| 1 | 5 | ApoC3; ApoE; ApoL1; PLTP; SAA1/2 |
| 2 | 6 | ApoC2; ApoC3; ApoE; ApoL1; CLU; PLTP |
| 3 | 4 | ApoC2; ApoC3; ApoL1; PLTP |
| 4 | 5 | ApoC1; ApoC3; CLU; PLTP; SAA4 |
| 5 | 3 | ApoA1; ApoC1; ApoC3 |
| 6 | 4 | ApoC3; ApoL1; PLTP; SAA1/2 |
| 7 | 3 | ApoC1; ApoC3; ApoM |
| 8 | 2 | ApoC3; SAA1/2 |
| 9 | 2 | ApoC1; ApoC3 |
| 10 | 1 | ApoC3 |
| 11 | 3 | ApoC3; ApoL1; SAA1/2 |
| 12 | 4 | ApoA1; ApoC1; ApoC3; CLU |
| 13 | 5 | ApoC1; ApoC3; ApoL1; HP; PLTP |
| 14 | 3 | ApoC3; ApoD; SAA1/2 |
| 15 | 6 | ApoA2; ApoC2; ApoC3; ApoD; CLU; SAA1/2 |
| 16 | 6 | ApoA2; ApoC2; ApoC3; ApoD; ApoM; SAA1/2 |
| 17 | 3 | ApoC1; ApoC2; ApoC3 |
| 18 | 5 | ApoA1; ApoC1; ApoC2; ApoC3; ApoC4 |

TABLE 2-continued

| Panel No. | Panel Size | Proteins |
|---|---|---|
| 19 | 6 | ApoA2; ApoC1; ApoC2; ApoC3; ApoD; SAA1/2 |
| 20 | 7 | ApoA2; ApoC3; ApoD; ApoE; ApoL1; PLTP; SAA1/2 |
| 21 | 4 | ApoC3; ApoM; PLTP; SAA1/2 |
| 22 | 4 | ApoC3; ApoD; PLTP; SAA1/2 |
| 23 | 7 | ApoA2; ApoC3; ApoD; ApoL1; ApoM; PLTP; SAA1/2 |
| 24 | 3 | ApoC1; ApoC3; SAA1/2 |
| 25 | 4 | ApoC1; ApoC3; C3; PLTP |
| 26 | 12 | ApoA2; ApoC2; ApoC3; ApoD; ApoE; ApoL1; ApoM; CETP; CLU; PLTP; PON1; SAA1/2 |

Peptide and Protein Quantification and Normalization

Peptide signal intensities are obtained by integrating the chromatographic peak for each peptide's "quantifier" transition. Proteins intensity is determined by summing the quantifier peak areas of each of the protein's targeted peptides and normalizing to the intensity of one or more HDL-associated proteins.

Algorithms for Efflux Capacity and CAD Risk

Multivariate algorithms for efflux capacity (on discovery cohort and fresh vs. frozen) and CAD risk (total, with, and without event) were developed based on the normalized intensities from measured proteins, and utilized to produce a value associated with the cholesterol efflux capacity or CAD risk of the originating serum sample. Model 1 is global cholesterol efflux on the discovery sample; Model 2 is global cholesterol efflux on fresh vs. frozen samples; Model 3 is total coronary artery disease (CAD) risk; Model 4 is CAD risk with event; and Model 5 is CAD risk without event. The general form of these models is shown below:

Models 1 and 2–Predicted global cholesterol efflux=$c_1 * p_1 + c_2 * p_2 \ldots c_n * p_n + i$ Models 3-5–CAD (with/without event) risk score=$c_1 * p_1 + c_2 * p_2 \ldots c_n * p_n + i$ where efflux is determined by the additive combination of a coefficient (c) multiplied by the normalized peak area (p) of a number of proteins plus a constant (i).

Statistical Analysis

The statistical analysis of the data for reach panel was performed using R (r-project.org) and Bioconductor (Biocanductor.org). The data was normalized to the total intensity of 15N ApoA1 protein. For proteins with two peptides Determining Absolute Molar Amounts of Proteins To obtain molar values, 5-point external calibration curves encompassing the range of measured signal for each peptide in Table 1 were constructed and monitored by LC-MS using synthetic peptide standards. Calibration curves were fit linearly and weighted 1/X, with X being the peptide concentration. The calculated molar values were then used to calculate the molar amount coefficients.

Panel 1

Models 1 and 2 were developed for predicted global cholesterol efflux for Panel 1. These models are shown below:

Models 1 and 2–Predicted global cholesterol efflux= $(i)+(c1)*ApoC3+(c2)*ApoE+(c3)*ApoL1+(c4)*PLTP+(c5)*SAA1/2$ The values for Models 1-5 are shown in Table 3A below. As an example, Model 1 would have the following values:

Model 1–Predicted Global Cholesterol Efflux= $9.25+(165.75)*ApoC3+(-834.8)*ApoE+(-144.26)*ApoL1+(-11548.33)*PLTP+(-160.58)*SAA1/2.$

TABLE 3A

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 9.25 | 5.27 | 2.49 | 2.42 | 1.08 |
| | (7.33, 11.17) | (2.12, 8.42) | (1.42, 3.57) | (1.16, 3.67) | (−0.12, 2.28) |
| ApoC3 | 165.75 | 230.53 | 11.44 | 7.8 | 13.1 |
| | (130.18, 201.31) | (128.91, 332.15) | (−10.76, 33.64) | (−20.13, 35.73) | (−12.41, 38.61) |
| ApoE | −834.8 | 4786.52 | −1434.48 | −1597.95 | −1221.33 |
| | (−1806.54, 136.93) | (1890.37, 7682.67) | (−2425.49, −443.47) | (−2853.08, −342.83) | (−2362.84, −79.81) |
| ApoL1 | −144.26 | 41.71 | 17.74 | −28 | 73.58 |
| | (−314.59, 26.07) | (−581.27, 664.7) | (−101.38, 136.86) | (−166.42, 110.41) | (−62.21, 209.38) |
| PLTP | −11548.33 | 14368.89 | −9141.23 | −9584.47 | −8509.05 |
| | (−21546.96, −1549.69) | (−5814.31, 34552.08) | (−15259.87, −3022.6) | (−16575.23, −2593.71) | (−15606.75, −1411.35) |
| SAA1/2 | −160.58 | −93.37 | 16.45 | 12.03 | 24.59 |
| | (−397.42, 76.26) | (−333.66, 146.92) | (−31.75, 64.66) | (−38.88, 62.94) | (−32.57, 81.75) |

Next, the model was tested in 35 replication samples. The correlation of the predicted cholesterol efflux with the cholesterol efflux measured in the laboratory was 0.78. Then, robust linear regression was applied to the proteins in this panel in another cohort of samples comprised of 76 fresh and frozen samples (40 fresh samples and 36 frozen samples). The model (Model 2) is shown above (Table 2) and the correlation of the predicted cholesterol efflux with the cholesterol efflux measured in the laboratory was 0.52. As an example, Model 2 would have the following values:

Model 2–Predicted Global Cholesterol Efflux=$5.27+(230.53)*ApoC3+(4786.52)*ApoE+(41.71)*ApoL1+(14368.89)*PLTP+(-93.37)*SAA1/2.$ Then, logistic regression was applied to the proteins in this panel in another cohort of samples comprised of 74 healthy controls and 157 CAD patients (83 with event and 74 without event). The models fitted to the healthy control versus CAD patients (model 3) had an area under the ROC curve (AUC) equals to 0.62 based on 5-fold cross-validation. The models fitted to the healthy controls versus CAD patients with event (model 4) had an area under the ROC curve (AUC) equals to 0.64 based on 5-fold cross-validation. The models fitted to the healthy controls versus CAD patients without event (model 5) had an area under the ROC curve (AUC) equals to 0.66 based on 5-fold cross-validation. The values for the three models are shown in Table 3A above, and the equations are shown below.

CAD (with/without event) risk score=$(i)+(c1)$*ApoC3+$(c2)$*ApoE+$(c3)$*ApoL1+$(c4)$*PLTP+$(c5)$*SAA1/2

Model 3-Total CAD risk score=2.49+(11.44)*ApoC3+(−1434.48)*ApoE+(17.74)*ApoL1+(−9141.23)*PLTP+(16.45)*SAA1/2.

Model 4-CAD with event risk score=2.42+(7.8)*ApoC3+(−1597.95)*ApoE+(−28)*ApoL1+(−9584.47)*PLTP+(12.03)*SAA1/2.

Model 5-CAD without event risk score=1.08+(13.1)*ApoC3+(−1221.33)*ApoE+(73.58)*ApoL1+(−8509.05)*PLTP+(24.59)*SAA1/2.

It is noted that the values in Table 3A also include a range for 95% confidence numbers. This range of numbers, for each value in the equations, could be substituted into the equations.

Next, these equations and values were used to calculate final values for three patients (P1, P2, and P3). The results are shown in Table 3B below.

reported below for the other panels in this example and Example 2 further below.

The risk score may be employed by health care personnel as an aid in deciding on treatment of patients suspected of having heart disease or for ruling patients out as in need of treatment or monitoring. For example, in general, a patient that has a percent risk of CAD of less than 10% is usually considered as low risk (e.g., patient may be considered as not in need of treatment or monitoring for heart disease), a patient with a percent risk of CAD of between 10-20% risk is usually considered as intermediate risk (e.g., patient may be monitored for additional signs of heart diseae), a patient with a percent risk of CAD of greater than 20% is usually considered at high risk (e.g., may be treated right away with therapeutics or surgical intervention).

As described above, the absolute molar amounts of each protein was determined using the absolute amount of the internal standard. These molar amounts were then used to determine the coefficients in Table 3C for Models 1, 3, 4, and 5. These coefficients, as they are in molar amounts, may be used in the Models, where the proteins values are determined by any type of detection assay (e.g., ELISA, mass spec., etc.).

TABLE 3B

Example of three samples on the five models - equation results

| Sample ID | Group | ApoC3 | ApoE | ApoL1 | PLTP | SAA1/2 | Model 1 Result | Model 2 Result | Model 3 Result | Model 4 Result | Model 5 Result |
|---|---|---|---|---|---|---|---|---|---|---|---|
| P1 | Control | 2.44E−02 | 1.43E−03 | 4.77E−03 | 2.15E−04 | 1.29E−04 | 8.92E+00 | 2.10E+01 | −1.16E+00 | −1.87E+00 | −1.82E+00 |
| P2 | CAD without event | 3.68E−02 | 9.11E−04 | 5.14E−03 | 1.42E−04 | 4.45E−04 | 1.21E+01 | 2.03E+01 | 4.13E−01 | −2.46E−01 | −3.65E−01 |
| P3 | CAD with event | 3.78E−02 | 3.61E−04 | 7.38E−03 | 1.00E−04 | 1.14E−01 | −5.36E+00 | 6.79E+00 | 3.50E+00 | 2.34E+00 | 3.64E+00 |

The risk score results in Table 3B may be used to generate a probability of CAD based on the formula that: Probability=$1/(1+\exp(-\text{risk score}))$. This value can then be multiplied by 100 to give a percent risk.

For example, for patient P1, the risk score result of Model 3 in Table 3A is −1.16. Plugging this into the formula gives

TABLE 3C

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.87 (6.06, 9.67) | 2.95 (1.67, 4.22) | 3.06 (1.54, 4.59) | 1.54 (0.08, 3) |
| ApoC3 | 150.35 (109.91, 190.8) | −7.7 (−33.51, 18.12) | −9.77 (−39.92, 20.38) | −4.82 (−33.73, 24.09) |
| ApoE | 19.06 (−1.5, 39.61) | 4.78 (−1.77, 11.33) | 5.06 (−2.78, 12.89) | 4.77 (−2.64, 12.17) |
| ApoL1 | −225.03 (−1949.57, 1499.51) | −404.37 (−1778.73, 969.99) | −1186.5 (−2856.46, 483.46) | 486.2 (−1081.6, 2053.99) |
| PLTP | −926.75 (−1911.87, 58.38) | −1697.85 (−2618.02, −777.67) | −2019.87 (−3134.92, −904.82) | −1559.79 (−2675.89, −443.69) |
| SAA1/2 | −46.32 (−93.15, 0.51) | 6.47 (−7.69, 20.63) | 7.02 (−6.34, 20.38) | 6.85 (−9.99, 23.68) | the following: $1/(1+\exp(-(-1.16)))=0.2386673$. Multiplying the result by 100 give a probability of 23.8% risk of CAD for patient P1. This same equation can be used for all of the models and patients in Table 3B, as well as the results It is noted that the values in Table 3C also include a range for 95% confidence numbers. This range of numbers, for each value in the equations (Models), could be substituted into the equations. For example, the ApoC3 value, rather than being exactly 150.35, could be any value between 109.91 and 190.8 and used in the Models.

Panel 2

Models 1-5 were developed for predicted global cholesterol efflux and CAD risk for Panel 2. Models 1-5 are shown below for Panel 2:

Models 1-5 for Panel 2=$(i)+(c1)*ApoC2+(c2)*ApoC3+(c3)*ApoE+(c4)*ApoL1+(c5)*CLU+(c6)*PLTP$ The values for Models 1-5 are shown in Table 4 below.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.61 based on 5-fold cross-validation. The models fitted to the healthy controls versus CAD patients with event had an area under the ROC curve (AUC) equals to 0.7 based on 5-fold cross-validation. The models fitted to the healthy controls versus CAD patients without event had

TABLE 4

| | Coefficients (95% CI) of the five models | | | | |
|---|---|---|---|---|---|
| Covariate | Model 1 on discovery samples | Model 2 on fresh/frozen samples | Model 3 on control vs. CAD samples | Model 4 on control vs. CAD with event samples | Model 5 on control vs. CAD without event samples |
| Intercept | 10.24 | 2.35 | 2.37 | 2.25 | 0.94 |
|  | (7.77, 12.71) | (−1.13, 5.82) | (0.93, 3.81) | (0.53, 3.96) | (−0.66, 2.54) |
| ApoC2 | 8.22 | 19.07 | −1.03 | −9.7 | 6.21 |
|  | (−7.84, 24.27) | (−23.3, 61.44) | (−10.28, 8.22) | (−21.29, 1.9) | (−4.49, 16.91) |
| ApoC3 | 139.78 | 116.81 | 12.61 | 26.37 | −0.3 |
|  | (66.16, 213.39) | (−7.87, 241.5) | (−15.85, 41.08) | (−9.56, 62.29) | (−31.87, 31.27) |
| ApoE | −847.46 | 3063.72 | −1411.1 | −1243.3 | −1486.37 |
|  | (−1829.43, 134.51) | (246.37, 5881.07) | (−2483.2, −339) | (−2541.27, 54.67) | (−2765.17, −207.57) |
| ApoL1 | −173.56 | 2.89 | 15.04 | −49.59 | 90.1 |
|  | (−342.89, −4.23) | (−589.53, 595.32) | (−108.01, 138.09) | (−196.46, 97.29) | (−51.48, 231.68) |
| CLU | −20.07 | 74.27 | 4.39 | 8.49 | 2.17 |
|  | (−51.39, 11.25) | (32.96, 115.58) | (−20.46, 29.24) | (−20.06, 37.05) | (−26.98, 31.32) |
| PLTP | −10560.75 | 5982.27 | −9474.65 | −9944.94 | −9272.59 |
|  | (−20606.52, −514.97) | (−13920.36, 25884.91) | (−15851.15, −3098.14) | (−17241.29, −2648.59) | (−16896.94, −1648.24) |

Next, the model was tested in 35 replication samples. The correlation of the predicted cholesterol efflux with the cholesterol efflux measured in the laboratory was 0.77. Then, robust linear regression was applied to the proteins in this panel in another cohort of samples comprised of 76 fresh and frozen samples (40 fresh samples and 36 frozen samples). The values for model (Model 2) are shown in Table 4 above, and the correlation of the predicted cholesterol efflux with the cholesterol efflux measured in the laboratory was 0.6.

an area under the ROC curve (AUC) equals to 0.59 based on 5-fold cross-validation. The values for the three models are shown in Table 4. It is noted that the values in Table 4 also include a range for 95% confidence numbers. This range of numbers, for each value in the equations, could be substituted into the equations.

The predicted cholesterol efflux and CAD risk, calculated based on the five models and three patients, are shown below in Table 5A.

TABLE 5A

| Example of three samples on the five models | | | | | | | |
|---|---|---|---|---|---|---|---|
| Sample ID | Group | ApoC2 | ApoC3 | ApoE | ApoL1 | CLU | PLTP |
| P1 | Control | 1.05E−01 | 2.44E−02 | 1.43E−03 | 4.77E−03 | 7.31E−02 | 2.15E−04 |
| P2 | CAD without event | 1.64E−01 | 3.68E−02 | 9.11E−04 | 5.14E−03 | 7.72E−02 | 1.42E−04 |
| P3 | CAD with event | 7.43E−02 | 3.78E−02 | 3.61E−04 | 7.38E−03 | 5.18E−02 | 1.00E−04 |

| Sample ID | Model 1 result | Model 2 result | Model3 result | Model 4 Result | Model 5 result |
|---|---|---|---|---|---|
| P1 | 8.74E+00 | 1.83E+01 | −1.09E+00 | −1.66E+00 | −1.95E+00 |
| P2 | 1.20E+01 | 1.91E+01 | 4.57E−01 | −5.11E−01 | −9.01E−02 |
| P3 | 1.24E+01 | 1.38E+01 | 1.65E+00 | 1.15E+00 | 7.00E−01 |

The results in Table 5A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 5b for Models 1, 3, 4, and 5. These coefficients, as they are in molar amounts, may be used in the Models, where the proteins values are determined by any type of detection assay (e.g., ELISA, mass spec., etc.).

robust linear regression was applied to the proteins in this panel in another cohort of samples comprised of 76 fresh and frozen samples (40 fresh samples and 36 frozen samples). The model (Model 2) is shown in Table 6, and the correlation of the predicted cholesterol efflux with the cholesterol efflux measured in the laboratory was 0.5.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve

TABLE 5B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 8.16 (6.27, 10.05) | 2.43 (1.09, 3.77) | 2.71 (1.08, 4.34) | 0.95 (−0.59, 2.48) |
| ApoC2 | 30.36 (−7.78, 68.49) | 5.89 (−18.26, 30.04) | −21.08 (−51.96, 9.81) | 28.08 (−1.41, 57.58) |
| ApoC3 | 108.4 (38.08, 178.72) | −14.16 (−47.37, 19.05) | 4.34 (−32.52, 41.19) | −31.15 (−75.65, 13.34) |
| ApoE | 13.53 (−7.41, 34.46) | 3.46 (−3.29, 10.22) | 3.41 (−4.82, 11.65) | 2.75 (−5.59, 11.09) |
| ApoL1 | −912.09 (−2738.85, 914.66) | −516.19 (−1916.4, 884.01) | −1422.46 (−3160.8, 315.87) | 533.35 (−1087.09, 2153.79) |
| CLU | −0.79 (−5.78, 4.2) | 3.38 (0.05, 6.71) | 3.95 (0.13, 7.77) | 3.61 (−0.44, 7.67) |
| PLTP | −802.57 (−2023.96, 418.81) | −2200.51 (−3268.98, −1132.04) | −2453.3 (−3732.07, −1174.54) | −2375.82 (−3733.56, −1018.08) |

It is noted that the values in Table 5B also include a range for 95% confidence numbers. This range of numbers, for each value in the equations (Models), could be substituted into the equations.

Panel 3

Models 1-5 were developed for predicted global cholesterol efflux and CAD risk for Panel 3. Models 1-5 are shown below for Panel 3:

Models 1-5 for Panel 3=($i$)+($c1$)*ApoC2+($c2$)*ApoC3+($c3$)*ApoL1+($c4$)*PLTP

The values for Models 1-5, are shown in Table 6 below.

(AUC) equals to 0.61 based on 5-fold cross-validation. The models fitted to the healthy controls versus CAD patients with event had an area under the ROC curve (AUC) equals to 0.68 based on 5-fold cross-validation. The models fitted to the healthy controls versus CAD patients without event had an area under the ROC curve (AUC) equals to 0.61 based on 5-fold cross-validation. The three CAD models are shown in Table 6. It is noted that the values in Table 6 also include a range for 95% confidence numbers. This range of numbers, for each value in the equations, could be substituted into the equations.

TABLE 6

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 9.01 | 6.77 | 2.25 | 2.33 | 0.79 |
|  | (7.03, 11) | (3.42, 10.13) | (1.22, 3.28) | (1.09, 3.57) | (−0.38, 1.95) |
| ApoC2 | 5.95 | 38.54 | −5.39 | −12.71 | 1.53 |
|  | (−9.85, 21.74) | (−9.98, 87.06) | (−13.62, 2.84) | (−23.09, −2.33) | (−7.95, 11.01) |
| ApoC3 | 131.17 | 181.11 | 17.02 | 28.49 | 3.74 |
|  | (55.44, 206.89) | (40.05, 322.17) | (−10.75, 44.79) | (−5.94, 62.91) | (−27.31, 34.79) |
| ApoL1 | −185.32 | 103.28 | 13.72 | −48.98 | 78.96 |
|  | (−358.1, −12.54) | (−589.45, 796) | (−104.25, 131.69) | (−189.04, 91.07) | (−57.76, 215.68) |
| PLTP | −11884.14 | 12215.85 | −10830.24 | −10826.34 | −10866.63 |
|  | (−21998.48, −1769.81) | (−10329.61, 34761.3) | (−16789.51, −4870.97) | (−17711.15, −3941.53) | (−17795.27, −3937.99) |

Next, the model was tested in 35 replication samples. The correlation of the predicted cholesterol efflux with the cholesterol efflux measured in the laboratory was 0.73. Then, The predicted cholesterol efflux and CAD risk, calculated based on the five models and three patients, are shown below in Table 7A.

TABLE 7A

Example of three samples on the five models

| Sample ID | Group | ApoC2 | ApoC3 | ApoL1 | PLTP | Model 1 result | Model 2 result | Model 3 result | Model 4 result | Model 5 result |
|---|---|---|---|---|---|---|---|---|---|---|
| P1 | Control | 1.05E−01 | 2.44E−02 | 4.77E−03 | 2.15E−04 | 9.40E+00 | 1.84E+01 | −1.72E−01 | −8.77E−01 | −9.27E−01 |
| P2 | CAD without event | 1.64E−01 | 3.68E−02 | 5.14E−03 | 1.42E−04 | 1.22E+01 | 2.20E+01 | 5.25E−01 | −4.92E−01 | 4.03E−02 |
| P3 | CAD with event | 7.43E−02 | 3.78E−02 | 7.38E−03 | 1.00E−04 | 1.19E+01 | 1.85E+01 | 1.50E+00 | 1.01E+00 | 5.33E−01 |

The results in Table 7A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 7b for Models 1, 3, 4, and 5. These coefficients, as they are in molar amounts, may be used in the Models, where the proteins values are determined by any type of detection assay (e.g., ELISA, mass spec., etc.).

Panel 4

Models 1-5 were developed for predicted global cholesterol efflux and CAD risk for Panel 4. Models 1-5 are shown below for Panel 4:

Models 1-5 for Panel 4=$(i)+(c1)*$ApoC1$+(c2)*$ApoC3$+(c3)*$CLU$+(c4)*$PLTP$+(c5)*$SAA4

The values for Models 1-5 are shown in Table 8 below:

TABLE 7B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 8.36 (6.59, 10.13) | 2.82 (1.56, 4.07) | 3.16 (1.61, 4.72) | 1.31 (−0.12, 2.74) |
| ApoC2 | 34.81 (−2.66, 72.27) | 9.05 (−14.36, 32.45) | −17.54 (−46.97, 11.9) | 31.55 (3.08, 60.02) |
| ApoC3 | 104.13 (34.16, 174.1) | −14.05 (−46.47, 18.38) | 5.95 (−29.96, 41.87) | −32.15 (−74.41, 10.11) |
| ApoL1 | −1076.35 (−2845.53, 692.83) | −259.77 (−1618.94, 1099.41) | −1075.42 (−2712.24, 561.4) | 772.99 (−810.95, 2356.93) |
| PLTP | −963.31 (−1951.03, 24.41) | −1615.81 (−2529.01, −702.61) | −1817.35 (−2914.18, −720.52) | −1718.2 (−2849.42, −586.98) |

It is noted that the values in Table 7B also include a range for 95% confidence numbers. This range of numbers, for each value in the equations (Models), could be substituted into the equations.

TABLE 8

Coefficients (95% CI) of the five models

| Covariate | Model 1 on discovery samples | Model 2 on fresh/frozen samples | Model 3 on control vs. CAD samples |
|---|---|---|---|
| Intercept | 8.88 (6.54, 11.22) | 2.68 (−0.26, 5.63) | 2.68 (1.02, 4.33) |
| ApoC1 | −4.51 (−19.33, 10.3) | 34.67 (−2.26, 71.61) | −29.14 (−41.18, −17.11) |
| ApoC3 | 170.01 (122.98, 217.05) | 170.68 (63.37, 278) | 34.38 (9.39, 59.37) |
| CLU | −11.11 (−45.05, 22.83) | 86.89 (44.74, 129.03) | 23.86 (−3.62, 51.34) |
| PLTP | −9421.93 (−20417.42, 1573.56) | 2022.53 (−16417.19, 20462.24) | −10225.32 (−16852.56, −3598.08) |
| SAA4 | −136.85 (−356.05, 82.34) | −641.3 (−1066.76, −215.84) | 148.65 (−35.43, 332.73) |

| Covariate | Model 4 on control vs. CAD with event samples | Model 5 on control vs. CAD without event samples |
|---|---|---|
| Intercept | 3.8 (1.57, 6.03) | 1.22 (−0.58, 3.01) |
| ApoC1 | −45.23 (−62.87, −27.59) | −22.03 (−35.47, −8.59) |
| ApoC3 | 38.53 (7.69, 69.36) | 31.21 (3.51, 58.92) |
| CLU | 30.36 (−2.52, 63.25) | 21.97 (−9.11, 53.05) |
| PLTP | −12481.55 (−20315.53, −4647.56) | −9328.19 (−16927.57, −1728.81) |
| SAA4 | 141.69 (−85.46, 368.85) | 137.92 (−53.14, 328.99) |

Next, the model was tested in 35 replication samples. The correlation of the predicted cholesterol efflux with the cholesterol efflux measured in the laboratory was 0.78. Then, robust linear regression was applied to the proteins in this panel in another cohort of samples comprised of 76 fresh and frozen samples (40 fresh samples and 36 frozen samples). The values for the model are shown in Table 8 above, and the correlation of the predicted cholesterol efflux with the cholesterol efflux measured in the laboratory was 0.68.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.72 based on 5-fold cross-validation. The models fitted to the healthy controls versus CAD patients with event had an area under the ROC curve (AUC) equals to 0.8 based on 5-fold cross-validation. The models fitted to the healthy controls versus CAD patients without event had an area under the ROC curve (AUC) equals to 0.66 based on 5-fold cross-validation. The value for the three models is shown in Table 8 above. It is noted that the values in Table 4 also include a range for 95% confidence numbers. This range of number, for each value, could be substituted into the equations.

The predicted cholesterol efflux and CAD risk, calculated based on the five models and three patients, are shown in Table 9A.

TABLE 9A

Example of three samples on the five models

| Sample ID | Group | ApoC3 | PLTP | ApoC1 | SAA4 | CLU | Model 1 result | Model 2 result | Model 3 result | Model 4 result | Model 5 result |
|---|---|---|---|---|---|---|---|---|---|---|---|
| P1 | Control | 2.44E−02 | 2.15E−04 | 1.54E−01 | 5.62E−03 | 7.31E−02 | 8.73E+00 | 1.54E+01 | −5.93E−01 | −1.89E+00 | −1.04E+00 |
| P2 | CAD NE | 1.78E−01 | 3.68E−02 | 7.72E−02 | 1.42E−04 | 4.92E−03 | 1.15E+01 | 1.90E+01 | −1.21E−01 | −1.56E+00 | −5.04E−01 |
| P3 | CAD WE | 9.49E−02 | 3.78E−02 | 5.18E−02 | 1.00E−04 | 6.19E−03 | 1.25E+01 | 1.32E+01 | 2.34E+00 | 2.17E+00 | 1.36E+00 |

The results in Table 9A may be used to generate a probability of CAD based on the formula that: Probability=$1/(1+\exp(-\text{risk score}))$.

As described above, the absolute molar amounts of each protein was determined using the absolute amount of the internal standard. These molar amounts were then used to determine the coefficients in Table 9b for Models 1, 3, 4, and 5. These coefficients, as they are in molar amounts, may be used in the Models, where the proteins values are determined by any type of detection assay (e.g., ELISA, mass spec., etc.).

TABLE 9B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 8.33 (6.59, 10.06) | 2.48 (1.08, 3.88) | 3.64 (1.65, 5.63) | 1.14 (−0.41, 2.69) |
| ApoC1 | 3.43 (−28.62, 35.48) | −55.75 (−85.47, −26.03) | −99.5 (−141.36, −57.63) | −37.93 (−72.16, −3.69) |
| ApoC3 | 164.34 (109, 219.69) | 21.95 (−9.77, 53.66) | 37.21 (−0.05, 74.47) | 17.18 (−18.43, 52.79) |
| CLU | −1.64 (−6.84, 3.55) | 5.53 (1.82, 9.24) | 6.67 (2.22, 11.11) | 5.82 (1.42, 10.23) |
| PLTP | −932.52 (−2259.32, 394.28) | −1639.91 (−2762.87, −516.96) | −2041.03 (−3436.66, −645.4) | −1895.18 (−3278.43, −511.92) |
| SAA4 | −18.73 (−76.88, 39.43) | 32.17 (−19.31, 83.65) | 30.26 (−36.9, 97.42) | 36.82 (−16.8, 90.43) |

It is noted that the values in Table 9B also include a range for 95% confidence numbers. This range of numbers, for each value in the equations (Models), could be substituted into the equations.

Panel 5

Models 1-5 were developed for predicted global cholesterol efflux and CAD risk for Panel 5. Models 1-5 as shown below for Panel 5:

Models 1-5 for Panel 5=$(i)+(c1)*\text{ApoA1}+(c2)*\text{ApoC1}+(c3)*\text{ApoC3}$ The value for Models 1-5 are shown in Table 10 below.

TABLE 10

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 6.79 (5.16, 8.42) | 5.65 (3.43, 7.87) | 4.5 (3.09, 5.91) | 5.81 (3.75, 7.87) | 2.92 (1.39, 4.45) |
| ApoA1 | 0.3 (−6.32, 6.91) | 4.97 (−3.35, 13.28) | −7.92 (−12.49, −3.34) | −10.33 (−16.23, −4.43) | −6.62 (−11.82, −1.43) |
| ApoC1 | −8.61 (−22.93, 5.7) | 53.21 (12.07, 94.35) | −18.43 (−30.25, −6.61) | −30.32 (−46.43, −14.21) | −13.75 (−27.09, −0.41) |
| ApoC3 | 154.71 (100.7, 208.71) | 136.97 (14.65, 259.29) | 30.37 (5.64, 55.1) | 35.51 (3.77, 67.25) | 27.67 (0.8, 54.53) |

Next, the model was tested in 35 replication samples. The correlation of the predicted cholesterol efflux with the cholesterol efflux measured in the laboratory was 0.85. Then, robust linear regression was applied to the proteins in this panel in another cohort of samples comprised of 76 fresh and frozen samples (40 fresh samples and 36 frozen samples). The model (Model 2) is shown in Table 10 above, and the correlation of the predicted cholesterol efflux with the cholesterol efflux measured in the laboratory was 0.53.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.75 based on 5-fold cross-validation. The models fitted to the healthy controls versus CAD patients with event had an area under the ROC curve (AUC) equals to 0.81 based on 5-fold cross-validation. The models fitted to the healthy controls versus CAD patients without event had an area under the ROC curve (AUC) equals to 0.68 based on 5-fold cross-validation. The values for the three CAD models are shown in Table 10. It is noted that values in Table 10 also include a range for 95% confidence numbers. This range of numbers, for each value, could be substituted into the equations.

The predicted cholesterol efflux and CAD risk, calculated based on the five models and three patients, are shown in Table 11A below.

TABLE 11A

Example of three samples on the five models

| Sample ID | Group | ApoA1 | ApoC1 | ApoC3 | Model 1 results | Model 2 results | Model 3 results | Model 4 results | Model 5 results |
|---|---|---|---|---|---|---|---|---|---|
| P1 | Control | 3.50E−01 | 1.54E−01 | 2.44E−02 | 9.35E+00 | 1.89E+01 | −3.64E−01 | −1.60E+00 | −8.39E−01 |
| P2 | CAD without event | 5.04E−01 | 1.78E−01 | 3.68E−02 | 1.11E+01 | 2.27E+01 | −1.65E+00 | −3.49E+00 | −1.85E+00 |
| P3 | CAD with event | 3.50E−01 | 9.49E−02 | 3.78E−02 | 1.19E+01 | 1.76E+01 | 1.13E+00 | 6.61E−01 | 3.42E−01 |

The results in Table 11A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 11b for Models 1, 3, 4, and 5. These coefficients, as they are in molar amounts, may be used in the Models, where the proteins values are determined by any type of detection assay (e.g., ELISA, mass spec., etc.).

TABLE 11B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.04 (5.31, 8.77) | 4.1 (2.81, 5.39) | 5.5 (3.56, 7.45) | 2.56 (1.16, 3.97) |
| ApoA1 | −0.71 (−6.91, 5.48) | −7.2 (−10.76, −3.64) | −9.39 (−14.15, −4.63) | −6.33 (−10.39, −2.26) |
| ApoC1 | −4.88 (−37.45, 27.69) | −25.95 (−52.42, 0.52) | −63.76 (−101.73, −25.79) | −10.65 (−40.16, 18.87) |
| ApoC3 | 153.37 (86.69, 220.06) | 27.71 (−5.15, 60.57) | 50.4 (11.47, 89.34) | 17.73 (−17.1, 52.56) |

It is noted that the values in Table 11B also include a range for 95% confidence numbers. This range of numbers, for each value in the equations (Models), could be substituted into the equations.

Panel 6

Models 1-5 were developed for predicted global cholesterol efflux and CAD risk for Panel 6. Models 1-5 are shown below for Panel 6.

Models 1-5 for Panel 6=$(i)+(c1)*$ApoC3+$(c2)*$ApoL1+$(c3)*$PLTP+$(c4)*$SAA1/2

The values for Models 1-5 are shown in Table 12 below:

TABLE 12

Coefficients (95% CI) of the five models

| Covariate | Model 1 on discovery samples | Model 2 on fresh/frozen samples | Model 3 on control vs. CAD samples |
|---|---|---|---|
| Intercept | 9.07 (7.11, 11.03) | 6.81 (3.32, 10.3) | 2.07 (1.07, 3.06) |
| ApoC3 | 155.67 (120.57, 190.77) | 264.96 (158.78, 371.15) | 6.44 (−14.88, 27.77) |
| ApoL1 | −162.25 (−333.07, 8.56) | 112.3 (−599.16, 823.75) | 15.6 (−101.36, 132.56) |
| PLTP | −12008.83 (−22103.47, −1914.19) | 13845.35 (−9188.77, 36879.47) | −11352.03 (−17238.65, −5465.41) |
| SAA1/2 | −152.41 (−394.01, 89.2) | −49.53 (−324.34, 225.29) | 18.33 (−32.47, 69.13) |

| Covariate | Model 4 on control vs. CAD with event samples | Model 5 on control vs. CAD without event samples |
|---|---|---|
| Intercept | 1.9 (0.76, 3.05) | 0.78 (−0.36, 1.92) |
| ApoC3 | 3.22 (−24, 30.44) | 8.88 (−16.05, 33.81) |
| ApoL1 | −35.85 (−172.72, 101.02) | 70.03 (−65.76, 205.81) |
| PLTP | −11703.94 (−18458.49, −4949.38) | −10772.9 (−17584.57, −3961.24) |
| SAA1/2 | 12.84 (−33.58, 59.25) | 27.01 (−34.3, 88.32) |

Next, the model was tested in 35 replication samples. The correlation of the predicted cholesterol efflux with the cholesterol efflux measured in the laboratory was 0.74. Then, robust linear regression was applied to the proteins in this panel in another cohort of samples comprised of 76 fresh and frozen samples (40 fresh samples and 36 frozen samples). The model (Model 2) is shown in Table 12, and the correlation of the predicted cholesterol efflux with the cholesterol efflux measured in the laboratory was 0.49.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.6 based on 5-fold cross-validation. The models fitted to the healthy controls versus CAD patients with event had an area under the ROC curve (AUC) equals to 0.63 based on 5-fold cross-validation. The models fitted to the healthy controls versus CAD patients without event had an area under the ROC curve (AUC) equals to 0.64 based on 5-fold cross-validation. The values for the three models for CAD risk (Models 3-5) are shown in Table 12. It is noted that the values in Table 12 also include a range for the 95% confidence numbers. This range of number, for each value, may be substituted into the equations.

The predicted cholesterol efflux and CAD risk, based on five models and three patients, are shown in Table 13A below.

TABLE 13A

Example of three samples on the five models

| Sample ID | Group | ApoC3 | ApoL1 | PLTP | SAA1/2 | Model 1 results | Model 2 results | Model 3 results | Model 4 results | Model 5 results |
|---|---|---|---|---|---|---|---|---|---|---|
| P1 | Control | 2.44E−02 | 4.77E−03 | 2.15E−04 | 1.29E−04 | 9.50E+00 | 1.68E+01 | −1.43E−01 | −7.07E−01 | −9.86E−01 |
| P2 | CAD without event | 3.68E−02 | 5.14E−03 | 1.42E−04 | 4.45E−04 | 1.22E+01 | 1.91E+01 | 7.86E−01 | 1.87E−01 | −4.76E−02 |
| P3 | CAD with event | 3.78E−02 | 7.38E−03 | 1.00E−04 | 1.14E−01 | −4.86E+00 | 1.34E+01 | 3.38E+00 | 2.05E+00 | 3.64E+00 |

The results in Table 13A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 13b for Models 1, 3, 4, and 5. These coefficients, as they are in molar amounts, may be used in the Models, where the proteins values are determined by any type of detection assay (e.g., ELISA, mass spec., etc.).

TABLE 13B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 8.42 (6.62, 10.23) | 2.88 (1.62, 4.14) | 3.06 (1.55, 4.58) | 1.42 (−0.01, 2.86) |
| ApoC3 | 160.2 (119.06, 201.34) | −6.2 (−31.74, 19.34) | −8.07 (−37.46, 21.31) | −3.24 (−31.82, 25.34) |
| ApoL1 | −512.14 (−2286.04, 1261.76) | −366.95 (−1728.96, 995.07) | −1158.46 (−2805.05, 488.13) | 530.45 (−1023.39, 2084.3) |
| PLTP | −1113.35 (−2125.81, −100.9) | −1556.46 (−2453.2, −659.71) | −1926.97 (−3025.69, −828.26) | −1390.87 (−2462.86, −318.88) |
| SAA1/2 | −39.15 (−87.06, 8.77) | 6.12 (−7.81, 20.05) | 6.91 (−6.48, 20.3) | 6.13 (−10.09, 22.35) |

It is noted that the values in Table 13B also include a range for 95% confidence numbers. This range of numbers, for each value in the equations (Models), could be substituted into the equations.

Panel 7

Models 1-5 were developed for predicted global cholesterol efflux and CAD risk for Panel 7. Models 1-5 are shown below for Panel 7.

Models 1-5 for Panel $7 = (i) + (c1)*ApoC1 + (c2)*ApoC3 + (c3)*ApoM$

The value for Models 1-5 are shown in Table 14 below.

TABLE 14

Coefficients (95% CI) of the five models

| Covariate | Model 1 on discovery samples | Model 2 on fresh/frozen samples | Model 3 on control vs. CAD samples |
|---|---|---|---|
| Intercept | 7.21 (5.63, 8.78) | 5.9 (3.81, 7.99) | 4.18 (2.83, 5.53) |
| ApoC1 | −7.84 (−21.67, 5.98) | 59.59 (20.86, 98.33) | −24.43 (−35.34, −13.53) |
| ApoC3 | 158.2 (109.84, 206.55) | 148.44 (27.7, 269.18) | 39.87 (13.95, 65.79) |
| ApoM | −1163.5 (−4676, 2349.01) | 2203.59 (−3047.33, 7454.5) | −1920.92 (−3105.94, −735.91) |

| Covariate | Model 4 on control vs. CAD with event samples | Model 5 on control vs. CAD without event samples |
|---|---|---|
| Intercept | 5.56 (3.57, 7.56) | 2.77 (1.27, 4.28) |
| ApoC1 | −36.62 (−52.22, −21.01) | −19.62 (−31.68, −7.57) |
| ApoC3 | 46.45 (13.49, 79.4) | 36 (7.71, 64.29) |
| ApoM | −2864.65 (−4496.36, −1232.93) | −1630.67 (−2947.06, −314.29) |

Next, the model was tested in 35 replication samples. The correlation of the predicted cholesterol efflux with the cholesterol efflux measured in the laboratory was 0.84. Then, robust linear regression was applied to the proteins in this panel in another cohort of samples comprised of 76 fresh and frozen samples (40 fresh samples and 36 frozen samples). The model (Model 2) is shown in Table 14, and the correlation of the predicted cholesterol efflux with the cholesterol efflux measured in the laboratory was 0.54.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.75 based on 5-fold cross-validation. The models fitted to the healthy controls versus CAD patients with event had an area under the ROC curve (AUC) equals to 0.82 based on 5-fold cross-validation. The models fitted to the healthy controls versus CAD patients without event had an area under the ROC curve (AUC) equals to 0.73 based on 5-fold cross-validation. The values for the three models are shown in Table 14 above. It is noted that the values in Table 14 also include a range for 95% confidence numbers. This range of numbers, for each value in the equations, could be substituted into the equations.

The predicted cholesterol efflux and CAD risk, calculated based on the five models and theree specific patients, are shown below in Table 15A.

TABLE 15A

Example of three samples on the five models

| Sample ID | Group | ApoC1 | ApoC3 | ApoM | Model 1 results | Model 2 results | Model 3 results | Model 4 results | Model 5 results |
|---|---|---|---|---|---|---|---|---|---|
| P1 | Control | 1.54E−01 | 2.44E−02 | 1.10E−03 | 8.58E+00 | 2.11E+01 | −7.27E−01 | −2.10E+00 | −1.17E+00 |
| P2 | CAD without event | 1.78E−01 | 3.68E−02 | 5.98E−04 | 1.09E+01 | 2.33E+01 | 1.49E−01 | −9.60E−01 | −3.72E−01 |
| P3 | CAD with event | 9.49E−02 | 3.78E−02 | 3.12E−04 | 1.21E+01 | 1.79E+01 | 2.77E+00 | 2.95E+00 | 1.76E+00 |

The results in Table 15A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 15b for Models 1, 3, 4, and 5. These coefficients, as they are in molar amounts, may be used in the Models, where the proteins values are determined by any type of detection assay (e.g., ELISA, mass spec., etc.).

TABLE 15B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.84 (6.12, 9.56) | 2.78 (1.75, 3.81) | 3.57 (2.12, 5.02) | 1.37 (0.23, 2.5) |
| ApoC1 | −4.8 (−35.04, 25.43) | −48.08 (−73.37, −22.8) | −82.74 (−119.2, −46.29) | −31.67 (−59.78, −3.56) |
| ApoC3 | 164.74 (106.79, 222.69) | 17.11 (−13.5, 47.71) | 31.46 (−3.58, 66.49) | 9.24 (−24.39, 42.87) |
| ApoM | −1432.91 (−3279.11, 413.29) | −13.88 (−287.54, 259.78) | −86.79 (−448.84, 275.26) | 22.92 (−287.49, 333.33) |

It is noted that the values in Table 15B also include a range for 95% confidence numbers. This range of numbers, for each value in the equations (Models), could be substituted into the equations.

Panel 8

Models 1-5 were developed for predicted global cholesterol efflux and CAD risk for Panel 8. Models 1-5 are shown below for Panel 8.

Models 1-5 for Panel 8=$(i)+(c1)*$ApoC3+$(c2)*$SAA1/2

The values for Models 1-5 are shown in Table 16 below.

TABLE 16

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 6.77 (5.79, 7.76) | 9 (7.26, 10.74) | 1 (0.34, 1.65) | 0.61 (−0.19, 1.41) | 0.05 (−0.72, 0.81) |
| ApoC3 | 133.56 (100.73, 166.38) | 248.87 (150.45, 347.3) | −8.18 (−25.76, 9.39) | −15.79 (−38.22, 6.64) | −2.5 (−22.81, 17.81) |
| SAA1/2 | −238.38 (−485.34, 8.57) | −11.19 (−285.55, 263.17) | 16.17 (−25.84, 58.17) | 13.31 (−27.29, 53.92) | 20.68 (−28.96, 70.31) |

Next, the model was tested in 35 replication samples. The correlation of the predicted cholesterol efflux with the cholesterol efflux measured in the laboratory was 0.8. Then, linear regression was applied to the proteins in this panel in another cohort of samples comprised of 76 fresh and frozen samples (40 fresh samples and 36 frozen samples). The model (Model 2) is shown in Table 16, and the correlation of the predicted cholesterol efflux with the cholesterol efflux measured in the laboratory was 0.48.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.58 based on 5-fold cross-validation. The models fitted to the healthy controls versus CAD patients with event had an area under the ROC curve (AUC) equals to 0.54 based on 5-fold cross-validation. The models fitted to the healthy controls versus CAD patients without event had an area under the ROC curve (AUC) equals to 0.53 based on 5-fold cross-validation. The values for the three models are shown in Table 16 above. It is noted that the values in Table 16 also include a range for 95% confidence numbers. This range of numbers, for each value in the equations, could be substituted into the equations.

The predicted cholesterol efflux and CAD risk, calculated based on the five models and there three specific patients, are shown below in Table 17A.

TABLE 17A

Example of three samples on the five models

| Sample ID | Group | ApoC3 | SAA1/2 | Model 1 Results | Model 2 results | Model 3 results | Model 4 results | Model 5 results |
|---|---|---|---|---|---|---|---|---|
| P1 | Control | 2.44E−02 | 1.29E−04 | 1.00E+01 | 1.51E+01 | 7.99E−01 | 2.26E−01 | −1.17E−02 |
| P2 | CAD without event | 3.68E−02 | 4.45E−04 | 1.16E+01 | 1.81E+01 | 7.03E−01 | 3.56E−02 | −3.59E−02 |
| P3 | CAD with event | 3.78E−02 | 1.14E−01 | −1.54E+01 | 1.71E+01 | 2.54E+00 | 1.54E+00 | 2.32E+00 |

The results in Table 17A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 17b for Models 1, 3, 4, and 5. These coefficients, as they are in molar amounts, may be used in the Models, where the proteins values are determined by any type of detection assay (e.g., ELISA, mass spec., etc.).

TABLE 17B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.06 (6.08, 8.04) | 1.2 (0.56, 1.84) | 0.72 (−0.05, 1.49) | 0.29 (−0.46, 1.04) |
| ApoC3 | 144.25 (105.86, 182.63) | −20.78 (−45.39, 3.83) | −27.66 (−59.08, 3.76) | −14.16 (−42.61, 14.28) |
| SAA1/2 | −52.01 (−98.97, −5.05) | 4.99 (−7.54, 17.51) | 4.66 (−6.62, 15.94) | 5.84 (−9.46, 21.14) |

It is noted that the values in Table 17B also include a range for 95% confidence numbers. This range of numbers, for each value in the equations (Models), could be substituted into the equations.

Panel 9

Models 1-5 were developed for predicted global cholesterol efflux and CAD risk for Panel 9. Models 1-5 are shown below for Panel 9.

Models 1-5 for Panel 9=(i)+(c1)*ApoC1+(c2)*ApoC3

The values for Models 1-5 are shown in Table 18 below.

Next, the model was tested in 35 replication samples. The correlation of the predicted cholesterol efflux with the cholesterol efflux measured in the laboratory was 0.85. Then, linear regression was applied to the proteins in this panel in another cohort of samples comprised of 76 fresh and frozen samples (40 fresh samples and 36 frozen samples). The model (Model 2) is shown in Table 18, and the correlation of the predicted cholesterol efflux with the cholesterol efflux measured in the laboratory was 0.54.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.7 based on 5-fold cross-validation. The models fitted to the healthy controls versus CAD patients with event had an area under the ROC curve (AUC) equals to 0.77 based on 5-fold cross-validation. The models fitted to the healthy controls versus CAD patients without event had an area under the ROC curve (AUC) equals to 0.68. The values for the three models are shown in Table 18 above. It is noted that the values in Table 18 also include a range for 95% confidence numbers. This range of numbers, for each value in the equations, could be substituted into the equations.

TABLE 18

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 7.04 (5.83, 8.25) | 7.09 (5, 9.19) | 3.39 (2.21, 4.57) | 4.25 (2.59, 5.92) | 2.01 (0.71, 3.31) |
| ApoC1 | −9.91 (−23.49, 3.67) | 59.51 (18.57, 100.44) | −27.83 (−38.44, −17.22) | −39.81 (−54.8, −24.81) | −21.91 (−33.77, −10.05) |
| ApoC3 | 160.27 (113.33, 207.2) | 124.47 (−1.15, 250.1) | 27.54 (3.77, 51.32) | 25.47 (−3.02, 53.97) | 25.36 (−0.74, 51.46) |

The predicted cholesterol efflux and CAD risk, calculated based on the five models and theree specific patients, are shown below in Table 19A.

TABLE 19A

Example of three samples on the five models

| Sample ID | Group | ApoC1 | ApoC3 | Model 1 Results | Model 2 results | Model 3 results | Model 4 results | Model 5 results |
|---|---|---|---|---|---|---|---|---|
| P1 | Control | 1.54E−01 | 2.44E−02 | 9.43E+00 | 1.93E+01 | −2.22E−01 | −1.25E+00 | −7.45E−01 |
| P2 | CAD without event | 1.78E−01 | 3.68E−02 | 1.12E+01 | 2.23E+01 | −5.50E−01 | −1.89E+00 | −9.58E−01 |
| P3 | CAD with event | 9.49E−02 | 3.78E−02 | 1.22E+01 | 1.74E+01 | 1.79E+00 | 1.44E+00 | 8.88E−01 |

The results in Table 19A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 19b for Models 1, 3, 4, and 5. These coefficients, as they are in molar amounts, may be used in the Models, where the proteins values are determined by any type of detection assay (e.g., ELISA, mass spec., etc.).

TABLE 19B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.1 (5.86, 8.35) | 2.77 (1.74, 3.8) | 3.54 (2.1, 4.97) | 1.38 (0.25, 2.5) |
| ApoC1 | −12.38 (−42.67, 17.92) | −48.51 (−72.37, −24.65) | −85.17 (−120.3, −50.04) | −30.97 (−57.39, −4.56) |
| ApoC3 | 161.9 (106.87, 216.92) | 17.05 (−13.51, 47.61) | 31 (−3.98, 65.97) | 9.2 (−24.41, 42.81) |

It is noted that the values in Table 19B also include a range for 95% confidence numbers. This range of numbers, for each value in the equations (Models), could be substituted into the equations.

Panel 10

Models 1-5 were developed for predicted global cholesterol efflux and CAD risk for Panel 10. Models 1-5 are shown below for Panel 10.

Models 1-5 for Panel 10=(i)+(c1)*ApoC3

The values for Models 1-5 are shown in Table 20 below.

Next, the model was tested in 35 replication samples. The correlation of the predicted cholesterol efflux with the cholesterol efflux measured in the laboratory was 0.8. Then, linear regression was applied to the proteins in this panel in another cohort of samples comprised of 76 fresh and frozen samples (40 fresh samples and 36 frozen samples). The model (Model 2) is shown in Table 20, and the correlation of the predicted cholesterol efflux with the cholesterol efflux measured in the laboratory was 0.48.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.56 based on 5-fold cross-validation. The models fitted to the healthy controls versus CAD patients with event had an area under the ROC curve (AUC) equals to 0.58 based on 5-fold cross-validation. The models fitted to the healthy controls versus CAD patients without event had an area under the ROC curve (AUC) equals to 0.49 based on 5-fold cross-validation. The values for the three models are shown in Table 20 above. It is noted that the values in Table 20 also include a range for 95% confidence numbers. This range of numbers, for each value in the equations, could be substituted into the equations.

TABLE 20

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 6.5 (5.54, 7.46) | 8.99 (7.28, 10.7) | 1.04 (0.39, 1.69) | 0.62 (−0.17, 1.42) | 0.13 (−0.62, 0.88) |
| ApoC3 | 135.98 (102.64, 169.33) | 248.28 (151.59, 344.96) | −8.71 (−26.24, 8.82) | −15.63 (−38.04, 6.78) | −3.87 (−24.05, 16.31) |

The predicted cholesterol efflux and CAD risk, calculated based on the five models and theree specific patients, are shown below in Table 21A.

TABLE 21A

Example of three samples on the five models

| Sample ID | Group | ApoC3 | Model 1 results | Model 2 results | Model 3 results | Model 4 results | Model 5 results |
|---|---|---|---|---|---|---|---|
| P1 | Control | 2.44E−02 | 9.82E+00 | 1.51E+01 | 8.28E−01 | 2.42E−01 | 3.60E−02 |
| P2 | CAD without event | 3.68E−02 | 1.15E+01 | 1.81E+01 | 7.21E−01 | 4.99E−02 | −1.17E−02 |
| P3 | CAD with event | 3.78E−02 | 1.16E+01 | 1.84E+01 | 7.12E−01 | 3.39E−02 | −1.57E−02 |

The results in Table 21A may be used to generate a probability of CAD based on the formula that: Probability=1/(1+exp(−risk score)). This can be multiplied by 100 to give a percent risk of CAD.

As described above, the absolute molar amounts of each protein was determined using the absolute amount of the internal standard. These molar amounts were then used to determine the coefficients in Table 21b for Models 1, 3, 4, and 5. These coefficients, as they are in molar amounts, may be used in the Models, where the proteins values are determined by any type of detection assay (e.g., ELISA, mass spec., etc.).

TABLE 21B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 6.79 (5.81, 7.76) | 1.23 (0.6, 1.87) | 0.71 (−0.06, 1.47) | 0.38 (−0.36, 1.12) |
| ApoC3 | 146.24 (106.86, 185.62) | −20.86 (−45.3, 3.59) | −25.95 (−56.69, 4.8) | −16.19 (−44.79, 12.41) |

It is noted that the values in Table 21B also include a range for 95% confidence numbers. This range of numbers, for each value in the equations (Models), could be substituted into the equations.

Panel 11

Models 1-5 were developed for predicted global cholesterol efflux and CAD risk for Panel 11. Models 1-5 are shown below for Panel 11.

Models 1-5 for Panel 11=($i$)+($c1$)*ApoC3+($c2$)*ApoL1+($c3$)*SAAJ/2

The values for Models 1-5 are shwon in Table 22 below.

Next, the model was tested in 35 replication samples. The correlation of the predicted cholesterol efflux with the cholesterol efflux measured in the laboratory was 0.8. Then, robust linear regression was applied to the proteins in this panel in another cohort of samples comprised of 76 fresh and frozen samples (40 fresh samples and 36 frozen samples). The model (Model 2) is shown in Table 22, and the correlation of the predicted cholesterol efflux with the cholesterol efflux measured in the laboratory was 0.48.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.54 based on 5-fold cross-validation. The models fitted to the healthy controls versus CAD patients with event had an area under the ROC curve (AUC) equals to 0.53 based on 5-fold cross-validation. The models fitted to the healthy controls versus CAD patients without event had an area under the ROC curve (AUC) equals to 0.48 based on 5-fold cross-validation. The values for the three models are shown in Table 22 above. It is noted that the values in Table 22 also include a range for 95% confidence numbers. This range of numbers, for each value in the equations, could be substituted into the equations.

TABLE 22

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 7.49 (6.04, 8.93) | 8.45 (6.19, 10.72) | 1.05 (0.26, 1.84) | 0.83 (−0.09, 1.75) | −0.15 (−1.1, 0.79) |
| ApoC3 | 136.23 (103.62, 168.85) | 279.13 (176.33, 381.92) | −7.24 (−26.67, 12.19) | −10.15 (−35.28, 14.99) | −5.82 (−28.14, 16.49) |
| ApoL1 | −141.29 (−316.98, 34.41) | 14.47 (−679.51, 708.46) | −12.73 (−124.39, 98.94) | −65.93 (−197.8, 65.94) | 47.1 (−81.86, 176.05) |
| SAA1/2 | −173.54 (−422.45, 75.37) | −66.74 (−339.55, 206.07) | 16.43 (−26.1, 58.96) | 14.75 (−26.94, 56.45) | 19.29 (−27.22, 65.8) |

The predicted cholesterol efflux and CAD risk, calculated based on the five models and theree specific patients, are shown below in Table 23A.

TABLE 23A

Example of three samples on the five models

| Sample ID | Group | ApoC3 | ApoL1 | SAA1/2 | Model 1 results | Model 2 results | Model 3 results | Model 4 results | Model 5 results |
|---|---|---|---|---|---|---|---|---|---|
| P1 | Control | 2.44E−02 | 4.77E−03 | 1.29E−04 | 1.01E+01 | 1.53E+01 | 8.12E−01 | 2.74E−01 | −6.92E−02 |
| P2 | CAD without event | 3.68E−02 | 5.14E−03 | 4.45E−04 | 1.17E+01 | 1.88E+01 | 7.23E−01 | 1.29E−01 | −1.17E−01 |
| P3 | CAD with event | 3.78E−02 | 7.38E−03 | 1.14E−01 | −8.24E+00 | 1.15E+01 | 2.56E+00 | 1.65E+00 | 2.18E+00 |

The results in Table 23A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 23b for Models 1, 3, 4, and 5. These coefficients, as they are in molar amounts, may be used in the Models, where the proteins values are determined by any type of detection assay (e.g., ELISA, mass spec., etc.).

Next, the model was tested in 35 replication samples. The correlation of the predicted cholesterol efflux with the cholesterol efflux measured in the laboratory was 0.86. Then, robust linear regression was applied to the proteins in this panel in another cohort of samples comprised of 76 fresh and frozen samples (40 fresh samples and 36 frozen samples). The model (Model 2) is shown in Table 24, and the correlation of the predicted cholesterol efflux with the cholesterol efflux measured in the laboratory was 0.61.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.75 based on 5-fold cross-validation. The models fitted to the healthy controls versus CAD patients

TABLE 23B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.19 (5.73, 8.65) | 1.39 (0.52, 2.27) | 1.21 (0.2, 2.22) | 0.12 (−0.9, 1.13) |
| ApoC3 | 139.93 (101.09, 178.76) | −19.93 (−44.56, 4.7) | −24.22 (−55.55, 7.12) | −15.05 (−43.94, 13.84) |
| ApoL1 | −293.77 (−2105.44, 1517.9) | −433.64 (−1763.38, 896.1) | −1199.54 (−2778.01, 378.93) | 385.2 (−1118.26, 1888.65) |
| SAA1/2 | −45.11 (−93.82, 3.6) | 5.34 (−7.79, 18.46) | 5.53 (−6.63, 17.7) | 5.44 (−9.13, 20.01) |

It is noted that the values in Table 23B also include a range for 95% confidence numbers. This range of numbers, for each value in the equations (Models), could be substituted into the equations.

Panel 12

Models 1-5 were developed for predicted global cholesterol efflux and CAD risk for Panel 12. Models 1-5 are shown below for Panel 12.

Models 1-5 for Panel 12=$(i)+(c1)*ApoA1+(c2)*ApoC1+(c3)*ApoC3+(c4)*CLU$

The values for Models 1-5 are shown in Table 24 below.

with event had an area under the ROC curve (AUC) equals to 0.82 based on 5-fold cross-validation. The models fitted to the healthy controls versus CAD patients without event had an area under the ROC curve (AUC) equals to 0.63 based on 5-fold cross-validation. The values for the three models are shown in Table 24 above. It is noted that the values in Table 24 also include a range for 95% confidence numbers. This range of numbers, for each value in the equations, could be substituted into the equations.

The predicted cholesterol efflux and CAD risk, calculated based on the five models and theree specific patients, are shown below in Table 25A.

TABLE 24

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 7.42 (5.17, 9.68) | 2.72 (−0.2, 5.64) | 3.72 (2.11, 5.32) | 4.88 (2.64, 7.13) | 2.37 (0.57, 4.17) |
| ApoA1 | 0.56 (−6.17, 7.29) | 3.21 (−4.77, 11.19) | −8.86 (−13.66, −4.07) | −11.5 (−17.76, −5.24) | −7.07 (−12.4, −1.75) |
| ApoC1 | −6.94 (−21.89, 8.02) | 31.24 (−9.84, 72.33) | −22.17 (−34.92, −9.42) | −35.76 (−53.61, −17.91) | −16.24 (−30.51, −1.96) |
| ApoC3 | 155.9 (101.65, 210.16) | 118.2 (2.02, 234.39) | 30.93 (6.07, 55.8) | 37.17 (4.94, 69.41) | 27.19 (0.28, 54.1) |
| CLU | −14.01 (−49.23, 21.2) | 67.59 (23.37, 111.81) | 25.11 (−2.44, 52.65) | 31.33 (−2.64, 65.3) | 16.86 (−14.02, 47.75) |

TABLE 25A

Example of three samples on the five models

| Sample ID | Group | ApoA1 | ApoC1 | ApoC3 | CLU | Model 1 results | Model 2 results | Model 3 results | Model 4 results | Model 5 results |
|---|---|---|---|---|---|---|---|---|---|---|
| P1 | Control | 3.50E−01 | 1.54E−01 | 2.44E−02 | 7.31E−02 | 9.33E+00 | 1.65E+01 | −2.02E−01 | −1.44E+00 | −7.06E−01 |
| P2 | CAD without event | 5.04E−01 | 1.78E−01 | 3.68E−02 | 7.72E−02 | 1.11E+01 | 1.95E+01 | −1.62E+00 | −3.49E+00 | −1.78E+00 |
| P3 | CAD with event | 3.50E−01 | 9.49E−02 | 3.78E−02 | 5.18E−02 | 1.21E+01 | 1.48E+01 | 9.84E−01 | 4.96E−01 | 2.55E−01 |

The results in Table 25A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 25b for Models 1, 3, 4, and 5. These coefficients, as they are in molar amounts, may be used in the Models, where the proteins values are determined by any type of detection assay (e.g., ELISA, mass spec., etc.).

Panel 13

Models 1-5 were developed for predicted global cholesterol efflux and CAD risk for Panel 13. Models 1-5 are shown below for Panel 13.

Models 1-5 for Panel 13 = $(i)+(c1)*ApoC1+(c2)*ApoC3+(c3)*ApoL1+(c4)*HP+(c5)*PLTP$ The values for Models 1-5 are shown in Table 26 below.

TABLE 25B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.74 (5.8, 9.68) | 3.38 (2, 4.75) | 4.74 (2.73, 6.74) | 1.88 (0.34, 3.42) |
| ApoA1 | 0.59 (−5.68, 6.87) | −8.09 (−11.84, −4.35) | −11.15 (−16.43, −5.87) | −6.54 (−10.67, −2.4) |
| ApoC1 | −0.62 (−33.63, 32.39) | −44.61 (−75.43, −13.79) | −88.72 (−132.24, −45.19) | −26.12 (−60.9, 8.65) |
| ApoC3 | 158.05 (91.75, 224.35) | 33.87 (0.98, 66.76) | 59.26 (17.78, 100.73) | 24.22 (−11.9, 60.33) |
| CLU | −3.98 (−8.51, 0.56) | 5.23 (1.7, 8.75) | 6.88 (2.61, 11.15) | 3.93 (−0.05, 7.91) |

It is noted that the values in Table 25B also include a range for 95% confidence numbers. This range of numbers, for each value in the equations (Models), could be substituted into the equations.

TABLE 26

Coefficients (95% CI) of the five models

| Covariate | Model 1 on discovery samples | Model 2 on fresh/frozen samples | Model 3 on control vs. CAD samples |
|---|---|---|---|
| Intercept | 9.14 (7, 11.28) | 5.31 (1.88, 8.73) | 3.78 (2.35, 5.21) |
| ApoC1 | −4.6 (−18.44, 9.23) | 58.66 (18.42, 98.9) | −26.68 (−37.95, −15.41) |
| ApoC3 | 168.03 (121.73, 214.33) | 151.18 (23.19, 279.18) | 35.12 (8.74, 61.51) |
| ApoL1 | −181.6 (−352.74, −10.45) | 121.78 (−533.53, 777.09) | −2.7 (−128.36, 122.97) |
| HP | 0.67 (−12.34, 13.67) | −0.54 (−21.61, 20.52) | 5.17 (−1.23, 11.56) |
| PLTP | −11470.77 (−22306.61, −634.93) | 8534.18 (−12947.37, 30015.73) | −8440.31 (−14727.13, −2153.48) |

| Covariate | Model 4 on control vs. CAD with event samples | Model 5 on control vs. CAD without event samples |
|---|---|---|
| Intercept | 5.04 (3.03, 7.06) | 2.11 (0.58, 3.64) |
| ApoC1 | −40.77 (−56.48, −25.07) | −19.34 (−32.02, −6.66) |
| ApoC3 | 43.01 (9.46, 76.56) | 27.83 (−0.92, 56.59) |
| ApoL1 | −63.15 (−215.22, 88.91) | 56.52 (−82.15, 195.2) |
| HP | 7.09 (−0.47, 14.64) | 2.65 (−4.17, 9.47) |
| PLTP | −10333.1 (−17902.02, −2764.18) | −7645.44 (−14756.5, −534.38) |

Next, the model was tested in 35 replication samples. The correlation of the predicted cholesterol efflux with the cholesterol efflux measured in the laboratory was 0.74. Then, robust linear regression was applied to the proteins in this panel in another cohort of samples comprised of 76 fresh and frozen samples (40 fresh samples and 36 frozen samples). The model (Model 2) is shown in Table 26, and the correlation of the predicted cholesterol efflux with the cholesterol efflux measured in the laboratory was 0.54.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.7 based on 5-fold cross-validation. The models fitted to the healthy controls versus CAD patients with event had an area under the ROC curve (AUC) equals to 0.79 based on 5-fold cross-validation. The models fitted to the healthy controls versus CAD patients without event had an area under the ROC curve (AUC) equals to 0.68 based on 5-fold cross-validation. The values for the three models are shown in Table 14 above. It is noted that the values in Table 26 also include a range for 95% confidence numbers. This range of numbers, for each value in the equations, could be substituted into the equations.

The predicted cholesterol efflux and CAD risk, calculated based on the five models and theree specific patients, are shown below in Table 27A.

TABLE 27A

Example of three samples on the five models

| SampleID | Group | Apo C1 | Apo C3 | Apo L1 | HP | PLTP | Model 1 results | Model 2 results | Model 3 results | Model 4 results | Model 5 results |
|---|---|---|---|---|---|---|---|---|---|---|---|
| P1 | Control | 1.54E−01 | 2.44E−02 | 4.77E−03 | 9.88E−02 | 2.15E−04 | 9.27E+00 | 2.04E+01 | −7.94E−01 | −2.01E+00 | −1.30E+00 |
| P2 | CAD without event | 1.78E−01 | 3.68E−02 | 5.14E−03 | 7.74E−02 | 1.42E−04 | 1.20E+01 | 2.31E+01 | −4.89E−01 | −1.87E+00 | −8.95E−01 |
| P3 | CAD with event | 9.49E−02 | 3.78E−02 | 7.38E−03 | 1.18E−01 | 1.00E−04 | 1.26E+01 | 1.83E+01 | 2.31E+00 | 2.13E+00 | 1.29E+00 |

The results in Table 27A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 27b for Models 1, 3, 4, and 5. These coefficients, as they are in molar amounts, may be used in the Models, where the proteins values are determined by any type of detection assay (e.g., ELISA, mass spec., etc.).

TABLE 27B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 8.52 (6.6, 10.45) | 3.38 (1.97, 4.8) | 4.68 (2.65, 6.71) | 1.75 (0.21, 3.29) |
| ApoC1 | 4.59 (−27.61, 36.79) | −39.77 (−66.06, −13.48) | −78.23 (−115.09, −41.37) | −20.24 (−50.12, 9.65) |
| ApoC3 | 160.39 (105.74, 215.05) | 16.4 (−16.52, 49.31) | 32.55 (−5, 70.11) | 5.14 (−29.46, 39.75) |
| ApoL1 | −972.17 (−2804.68, 860.34) | −404.75 (−1796.14, 986.65) | −1177.21 (−2945.06, 590.64) | 516.49 (−1039.22, 2072.2) |
| HP | 1.83 (−152.83, 156.49) | 40.19 (−31.75, 112.12) | 49.26 (−42.83, 141.35) | 27.05 (−50.12, 104.21) |
| PLTP | −1276.87 (−2418.35, −135.38) | −950.63 (−1953.57, 52.3) | −1120.56 (−2332.11, 90.99) | −1075.22 (−2268.94, 118.5) |

It is noted that the values in Table 27B also include a range for 95% confidence numbers. This range of numbers, for each value in the equations (Models), could be substituted into the equations.

Panel 14

Models 1-5 were developed for predicted global cholesterol efflux and CAD risk for Panel 14. Models 1-5 are shown below for Panel 14.

Models 1-5 for Panel 14=($i$)+($c1$)*ApoC3+($c2$)*ApoD+($c3$)*SAA1/2

The values for Models 1-5 are shown in Table 28 below.

TABLE 28

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 6.34 (5.1, 7.58) | 8.94 (6.17, 11.7) | 3.08 (1.88, 4.28) | 3.39 (1.86, 4.92) | 1.73 (0.37, 3.09) |
| ApoC3 | 131.35 (98.36, 164.33) | 247.77 (141.89, 353.65) | −4.72 (−23.39, 13.96) | −11.14 (−35.34, 13.06) | −0.44 (−21.37, 20.49) |
| ApoD | 4.1 (−3.05, 11.25) | 0.86 (−28.08, 29.8) | −16.67 (−24.25, −9.1) | −22.66 (−32.66, −12.66) | −13.03 (−21.65, −4.42) |
| SAA1/2 | −215.22 (−464.98, 34.55) | −9.87 (−289.72, 269.99) | 11.64 (−30.06, 53.34) | 4.58 (−42.94, 52.1) | 19.25 (−30.99, 69.49) |

Next, the model was tested in 35 replication samples. The correlation of the predicted cholesterol efflux with the cholesterol efflux measured in the laboratory was 0.8. Then, linear regression was applied to the proteins in this panel in another cohort of samples comprised of 76 fresh and frozen samples (40 fresh samples and 36 frozen samples). The model (Model 2) is shown in Table 28, and the correlation of the predicted cholesterol efflux with the cholesterol efflux measured in the laboratory was 0.48.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.68 based on 5-fold cross-validation. The models fitted to the healthy controls versus CAD patients with event had an area under the ROC curve (AUC) equals to 0.71 based on 5-fold cross-validation. The models fitted to the healthy controls versus CAD patients without event had an area under the ROC curve (AUC) equals to 0.65 based on 5-fold cross-validation. The values for the three models are shown in Table 28 above. It is noted that the values in Table 28 also include a range for 95% confidence numbers. This range of numbers, for each value in the equations, could be substituted into the equations.

The predicted cholesterol efflux and CAD risk, calculated based on the five models and three specific patients, are shown below in Table 29A.

TABLE 29A

Example of three samples on the five models

| Sample ID | Group | ApoC3 | ApoD | SAA1/2 | Model 1 results | Model 2 results | Model 3 results | Model 4 results | Model 5 results |
|---|---|---|---|---|---|---|---|---|---|
| P1 | Control | 2.44E−02 | 2.18E−01 | 1.29E−04 | 1.04E+01 | 1.52E+01 | −6.69E−01 | −1.82E+00 | −1.12E+00 |
| P2 | CAD without event | 3.68E−02 | 2.40E−01 | 4.45E−04 | 1.21E+01 | 1.82E+01 | −1.09E+00 | −2.46E+00 | −1.41E+00 |
| P3 | CAD with event | 3.78E−02 | 5.99E−02 | 1.14E−01 | −1.30E+01 | 1.72E+01 | 3.23E+00 | 2.14E+00 | 3.13E+00 |

The results in Table 29A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 29b for Models 1, 3, 4, and 5. These coefficients, as they are in molar amounts, may be used in the Models, where the proteins values are determined by any type of detection assay (e.g., ELISA, mass spec., etc.).

TABLE 29B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 6.79 (5.63, 7.94) | 2.79 (1.69, 3.89) | 2.64 (1.32, 3.97) | 1.7 (0.4, 2.99) |
| ApoC3 | 142.12 (103.39, 180.86) | −17.63 (−42.6, 7.34) | −22.33 (−53.87, 9.21) | −11.38 (−39.68, 16.91) |
| ApoD | 4.6 (−5.57, 14.78) | −28.06 (−42.98, −13.14) | −35.11 (−54.02, −16.19) | −24.44 (−42.64, −6.24) |
| SAA1/2 | −49.79 (−97.08, −2.5) | 3.61 (−7.84, 15.05) | 1.78 (−9.68, 13.24) | 5.38 (−9.11, 19.87) |

It is noted that the values in Table 29B also include a range for 95% confidence numbers. This range of numbers, for each value in the equations (Models), could be substituted into the equations.

Panel 15

Models 1-5 were developed for predicted global cholesterol efflux and CAD risk for Panel 15. Models 1-5 are shown below for Panel 15.

Models 1-5 for Panel 15=$(i)+(c1)*$ApoA2+$(c2)$
*ApoC2+$(c3)*$ApoC3+$(c4)*$ApoD+$(c5)*$CLU+
$(c6)*$SAA1/2

The values for Models 1-5 are shown in Table 30 below.

to 0.7 based on 5-fold cross-validation. The models fitted to the healthy controls versus CAD patients without event had an area under the ROC curve (AUC) equals to 0.6 based on 5-fold cross-validation. The values for the three models are shown in Table 30 above. It is noted that the values in Table 30 also include a range for 95% confidence numbers. This range of numbers, for each value in the equations, could be substituted into the equations.

The predicted cholesterol efflux and CAD risk, calculated based on the five models and theree specific patients, are shown below in Table 31A.

TABLE 30

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| ApoA2 | 0.46 (0.05, 0.87) | 2.16 (1.63, 2.69) | −0.41 (−0.77, −0.05) | −0.44 (−0.86, −0.01) | −0.39 (−0.83, 0.05) |
| ApoC2 | 10.57 (10.16, 10.98) | 33.19 (32.66, 33.72) | −1.51 (−10.3, 7.28) | −8.2 (−19.52, 3.13) | 1.67 (−8.04, 11.38) |
| ApoC3 | 56.71 (56.29, 57.12) | 99.26 (98.73, 99.79) | 10.1 (−17.26, 37.46) | 14.13 (−18.7, 46.97) | 7.84 (−22.18, 37.86) |
| ApoD | 3.64 (3.23, 4.05) | 9.41 (8.88, 9.94) | −15.51 (−23.47, −7.55) | −20.14 (−30.66, −9.61) | −12.43 (−21.29, −3.58) |
| CLU | 12.33 (11.92, 12.74) | 48.06 (47.53, 48.59) | 0.06 (−24.83, 24.94) | 3.89 (−25.57, 33.35) | −1.71 (−30.28, 26.86) |
| SAA1/2 | −131.48 (−131.89, −131.07) | 36.57 (36.04, 37.1) | 12.29 (−34.53, 59.1) | 4.67 (−64.01, 73.34) | 20.11 (−33.7, 73.92) |

Next, the model was tested in 35 replication samples. The correlation of the predicted cholesterol efflux with the cholesterol efflux measured in the laboratory was 0.73. Then, partial linear regression was applied to the proteins in this panel in another cohort of samples comprised of 76 fresh and frozen samples (40 fresh samples and 36 frozen samples). The model (Model 2) is shown in Table 20, and the correlation of the predicted cholesterol efflux with the cholesterol efflux measured in the laboratory was 0.57.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.61 based on 5-fold cross-validation. The models fitted to the healthy controls versus CAD patients with event had an area under the ROC curve (AUC) equals

TABLE 31A

Example of three samples on the five models

| Sample ID | Group | ApoA 2 | Apo C2 | ApoC3 | Apo D | CLU | SAA1/2 |
|---|---|---|---|---|---|---|---|
| P1 | Control | 5.65E+00 | 1.05E−01 | 2.44E−02 | 2.18E−01 | 7.31E−02 | 1.29E−04 |
| P2 | CAD without event | 3.70E+00 | 1.64E−01 | 3.68E−02 | 2.40E−01 | 7.72E−02 | 4.45E−04 |
| P3 | CAD with event | 2.65E+00 | 7.43E−02 | 3.78E−02 | 5.99E−02 | 5.18E−02 | 1.14E−01 |

| Sample ID | Model 1 results | Model 2 results | Model3 results | Model 4 results | Model 5 results |
|---|---|---|---|---|---|
| P1 | 1.07E+01 | 2.05E+02 | −1.08E+00 | −2.23E+00 | −1.52E+00 |
| P2 | 1.12E+01 | 1.47E+02 | −5.83E−01 | −2.11E+00 | −8.40E−01 |
| P3 | −6.12E+00 | 1.03E+02 | 4.19E+00 | 3.16E+00 | 4.00E+00 |

The results in Table 31A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 31b for Models 1, 3, 4, and 5. These coefficients, as they are in molar amounts, may be used in the Models, where the proteins values are determined by any type of detection assay (e.g., ELISA, mass spec., etc.).

TABLE 31B

| | | | Model 4 on control | Model 5 on control |
| | Model 1 on | Model 3 on control | vs. CAD with | vs. CAD without |
| Covariate | discovery samples | vs. CAD samples | event samples | event samples |
| --- | --- | --- | --- | --- |
| ApoA2 | 4.14 (3.71, 4.56) | 0.16 (−0.9, 1.21) | 0.33 (−0.68, 1.34) | −1.7 (−7.6, 4.19) |
| ApoC2 | 32.53 (32.11, 32.96) | 14.64 (−9.95, 39.23) | −9.79 (−41.5, 21.91) | 28.06 (−2.07, 58.2) |
| ApoC3 | 68.37 (67.95, 68.79) | −34.92 (−71.98, 2.14) | −20.27 (−61.28, 20.75) | −39.59 (−91.11, 11.94) |
| ApoD | 4.87 (4.45, 5.3) | −30.91 (−46.42, −15.41) | −34.7 (−54.03, −15.36) | −28.59 (−47.61, −9.57) |
| CLU | 1.04 (0.61, 1.46) | 0.91 (−1.88, 3.7) | 1.18 (−2.04, 4.4) | 1.64 (−2.36, 5.64) |
| SAA1/2 | −28.19 (−28.61, −27.76) | 3.39 (−7.71, 14.5) | 1.48 (−10.3, 13.27) | 5.06 (−8.76, 18.88) |

It is noted that the values in Table 31B also include a range for 95% confidence numbers. This range of numbers, for each value in the equations (Models), could be substituted into the equations.

Panel 16

Models 1-5 were developed for predicted global cholesterol efflux and CAD risk for Panel 16. Models 1-5 are shown below for Panel 16.

Models 1-5 for Panel 16=$(i)+(c1)*ApoA2+(c2)*ApoC2+(c3)*ApoC3+(c4)*ApoD+(c5)*ApoM+(c6)*SAA1/2$ The values for Models 1-5 are shown in Table 32 below.

lation of the predicted cholesterol efflux with the cholesterol efflux measured in the laboratory was 0.51.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.65 based on 5-fold cross-validation. The models fitted to the healthy controls versus CAD patients with event had an area under the ROC curve (AUC) equals to 0.74 based on 5-fold cross-validation. The models fitted to the healthy controls versus CAD patients without event had an area under the ROC curve (AUC) equals 0.65 based on 5-fold cross-validation. The values for the three

TABLE 32

Coefficients (95% CI) of the five models

| Covariate | Model 1 on discovery samples | Model 2 on fresh/frozen samples | Model 3 on control vs. CAD samples |
| --- | --- | --- | --- |
| ApoA2 | 0.46 (0.05, 0.87) | 2.16 (1.59, 2.74) | −0.24 (−0.6, 0.13) |
| ApoC2 | 10.61 (10.2, 11.02) | 33.2 (32.63, 33.77) | −1.99 (−10.85, 6.87) |
| ApoC3 | 56.94 (56.53, 57.35) | 99.29 (98.72, 99.86) | 17.61 (−11.05, 46.28) |
| ApoD | 3.66 (3.25, 4.07) | 9.41 (8.84, 9.99) | −12.49 (−20.93, −4.04) |
| ApoM | 1540.86 (1540.45, 1541.27) | 2544.91 (2544.33, 2545.48) | −1374.81 (−2584.92, −164.7) |
| SAA1/2 | −132.02 (−132.43, −131.61) | 36.58 (36.01, 37.15) | 10.26 (−32.89, 53.41) |

| Covariate | Model 4 on control vs. CAD with event samples | Model 5 on control vs. CAD without event samples |
| --- | --- | --- |
| ApoA2 | −0.22 (−0.65, 0.21) | −0.24 (−0.69, 0.21) |
| ApoC2 | −8.14 (−19.36, 3.08) | 0.69 (−9.1, 10.49) |
| ApoC3 | 25.65 (−10.1, 61.41) | 13.6 (−17.71, 44.91) |
| ApoD | −15.97 (−27.29, −4.65) | −10.26 (−19.59, −0.93) |
| ApoM | −1943.77 (−3607.26, −280.29) | −1066.76 (−2448.86, 315.34) |
| SAA1/2 | 2.83 (−70.86, 76.52) | 17.62 (−31.9, 67.13) |

Next, the model was tested in 35 replication samples. The correlation of the predicted cholesterol efflux with the cholesterol efflux measured in the laboratory was 0.65. Then, partial linear regression was applied to the proteins in this panel in another cohort of samples comprised of 76 fresh and frozen samples (40 fresh samples and 36 frozen samples). The model (Model 2) is shown in Table 32, and the corre- CAD models are shown in Table 32 above. It is noted that the values in Table 32 also include a range for 95% confidence numbers. This range of numbers, for each value in the equations, could be substituted into the equations.

The predicted cholesterol efflux and CAD risk, calculated based on the five models and theree specific patients, are shown below in Table 33A.

TABLE 33A

Example of three samples on the five models

| Sample ID | Group | ApoA 2 | ApoC 2 | Apo C3 | Apo D | ApoM | SAA1/2 |
|---|---|---|---|---|---|---|---|
| P1 | Control | 5.65E+00 | 1.05E−01 | 2.44E−02 | 2.18E−01 | 1.10E−03 | 1.29E−04 |
| P2 | CAD without event | 3.70E+00 | 1.64E−01 | 3.68E−02 | 2.40E−01 | 5.98E−04 | 4.45E−04 |
| P3 | CAD with event | 2.65E+00 | 7.43E−02 | 3.78E−02 | 5.99E−02 | 3.12E−04 | 1.14E−01 |

| Sample ID | Model 1 results | Model 2 results | Model 3 results | Model 4 results | Model 5 results |
|---|---|---|---|---|---|
| P1 | 1.17E+01 | 2.60E+01 | −1.07E+00 | −2.31E+00 | −1.48E+00 |
| P2 | 1.14E+01 | 2.59E+01 | −8.30E−02 | −1.41E+00 | −4.90E−01 |
| P3 | −6.15E+00 | 3.09E+02 | 4.18E+00 | 3.33E+00 | 3.87E+00 |

The results in Table 33A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 33b for Models 1, 3, 4, and 5. These coefficients, as they are in molar amounts, may be used in the Models, where the proteins values are determined by any type of detection assay (e.g., ELISA, mass spec., etc.).

TABLE 33B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| ApoA2 | 4.01 (3.59, 4.44) | 0.26 (−0.99, 1.5) | 0.37 (−0.74, 1.48) | 0.07 (−3.65, 3.79) |
| ApoC2 | 31.59 (31.16, 32.01) | 19.64 (−5.42, 44.71) | −4.1 (−35.55, 27.35) | 32.98 (2.09, 63.86) |
| ApoC3 | 66.38 (65.96, 66.81) | −32.74 (−68.92, 3.44) | −14.59 (−53.79, 24.61) | −41.41 (−92.27, 9.46) |
| ApoD | 4.73 (4.31, 5.16) | −30.61 (−46.19, −15.04) | −33.71 (−53.08, −14.34) | −28.22 (−47.16, −9.28) |
| ApoM | 768.63 (768.2, 769.05) | −196.56 (−458.93, 65.81) | −299.75 (−633.76, 34.27) | −130.75 (−456.12, 194.62) |
| SAA1/2 | −27.37 (−27.79, −26.94) | 3.15 (−7.63, 13.92) | 1.67 (−10.1, 13.43) | 4.53 (−8.36, 17.42) |

It is noted that the values in Table 33B also include a range for 95% confidence numbers. This range of numbers, for each value in the equations (Models), could be substituted into the equations.

Panel 17

Models 1-5 were developed for predicted global cholesterol efflux and CAD risk for Panel 17. Models 1-5 are shown below for Panel 17.

Models 1-5 for Panel 17=$(i)+(c1)*ApoC1+(c2)*ApoC2+(c3)*ApoC3$

The values for Models 1-5 are shown in Table 34 below.

TABLE 34

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 6.85 (5.54, 8.17) | 7.18 (4.83, 9.52) | 4.18 (2.8, 5.56) | 5.16 (3.2, 7.11) | 2.89 (1.37, 4.42) |
| ApoC1 | −0.33 (−7.09, 6.42) | 57.21 (12.79, 101.63) | −44.22 (−60.58, −27.86) | −56.07 (−78.04, −34.09) | −42.17 (−60.79, −23.56) |
| ApoC2 | 1.6 (−7.42, 10.62) | 2.9 (−51.48, 57.28) | 18.61 (5.53, 31.7) | 18.05 (1.64, 34.45) | 22.88 (8.08, 37.68) |
| ApoC3 | 117.14 (55.21, 179.08) | 121.67 (−9.06, 252.41) | 8.53 (−18.51, 35.57) | 5.36 (−28.85, 39.57) | 4.04 (−26.02, 34.1) |

Next, the model was tested in 35 replication samples. The correlation of the predicted cholesterol efflux with the cholesterol efflux measured in the laboratory was 0.81. Then, elastic net model was applied to the proteins in this panel in another cohort of samples comprised of 76 fresh and frozen samples (40 fresh samples and 36 frozen samples). The model (Model 2) is shown in Table 34 above, and the correlation of the predicted cholesterol efflux with the cholesterol efflux measured in the laboratory was 0.53.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.74 based on 5-fold cross-validation. The models fitted to the healthy controls versus CAD patients with event had an area under the ROC curve (AUC) equals to 0.78 based on 5-fold cross-validation. The models fitted to the healthy controls versus CAD patients without event had an area under the ROC curve (AUC) equals to 0.72 based on 5-fold cross-validation. The values for the three models are shown in Table 34 above. It is noted that the values in Table 34 also include a range for 95% confidence numbers. This range of numbers, for each value in the equations, could be substituted into the equations.

The predicted cholesterol efflux and CAD risk, calculated based on the five models and thereee specific patients, are shown below in Table 35A.

TABLE 35A

Example of three samples on the five models

| Sample ID | Group | ApoC1 | ApoC2 | ApoC3 | Model 1 results | Model 2 results | Model 3 results | Model 4 results | Model 5 results |
|---|---|---|---|---|---|---|---|---|---|
| P1 | Control | 1.54E−01 | 1.05E−01 | 2.44E−02 | 9.83E+00 | 2.18E+01 | −4.62E−01 | −1.45E+00 | −1.09E+00 |
| P2 | CAD without event | 1.78E−01 | 1.64E−01 | 3.68E−02 | 1.14E+01 | 2.97E+01 | −3.24E−01 | −1.67E+00 | −7.12E−01 |
| P3 | CAD with event | 9.49E−02 | 7.43E−02 | 3.78E−02 | 1.14E+01 | 1.86E+01 | 1.69E+00 | 1.38E+00 | 7.44E−01 |

The results in Table 35A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 35B for Models 1, 3, 4, and 5. These coefficients, as they are in molar amounts, may be used in the Models, where the proteins values are determined by any type of detection assay (e.g., ELISA, mass spec., etc.).

TABLE 35B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.16 (5.99, 8.34) | 3.06 (1.99, 4.14) | 3.62 (2.17, 5.07) | 1.69 (0.5, 2.88) |
| ApoC1 | −16.21 (−45.24, 12.82) | −74.17 (−104.44, −43.91) | −99.35 (−139.9, −58.79) | −63.64 (−97.9, −29.38) |
| ApoC2 | 19.17 (−30.56, 68.89) | 45.46 (14.48, 76.45) | 28.17 (−9.23, 65.57) | 58.36 (22.67, 94.06) |
| ApoC3 | 137.06 (40.87, 233.26) | −4.71 (−39.19, 29.78) | 18.89 (−20.52, 58.3) | −19.17 (−63.72, 25.39) |

It is noted that the values in Table 35B also include a range for 95% confidence numbers. This range of numbers, for each value in the equations (Models), could be substituted into the equations.

Panel 18

Models 1-5 were developed for predicted global cholesterol efflux and CAD risk for Panel 18. Models 1-5 are shown below for Panel 18.

Models 1-5 for Panel 18=$(i)+(c1)*$ApoA1+$(c2)*$ApoC1+$(c3)*$ApoC2+$(c4)*$ApoC3+$(c5)*$ApoC4

The values for Models 1-5 are shown in Table 36 below.

TABLE 36

Coefficients (95% CI) of the five models

| Covariate | Model 1 on discovery samples | Model 2 on fresh/frozen samples | Model 3 on control vs. CAD samples |
|---|---|---|---|
| Intercept | 7.4 (5.69, 9.11) | 6.53 (4.06, 9) | 4.97 (3.42, 6.51) |
| ApoA1 | −1.45 (−8.13, 5.23) | 5.48 (−3.87, 14.83) | −6.81 (−11.51, −2.1) |
| ApoC1 | −8.73 (−23.79, 6.33) | 49.64 (−5.16, 104.44) | −34.89 (−52.8, −16.98) |
| ApoC2 | 4.27 (−14.9, 23.43) | 15.65 (−59.86, 91.16) | 11.41 (−3.71, 26.52) |
| ApoC3 | 157.14 (74.2, 240.08) | 105.42 (−39.19, 250.02) | 10.97 (−18.12, 40.05) |
| ApoC4 | −305.14 (−1255.56, 645.28) | −1363.6 (−6021.96, 3294.75) | 778.4 (− 247.73, 1804.54) |

| | Covariate | Model 4 on control vs. CAD with event samples | Model 5 on control vs. CAD without event samples |
|---|---|---|---|
| | Intercept | 6.4 (4.16, 8.64) | 3.36 (1.64, 5.08) |
| | ApoA1 | −9.65 (−15.66, −3.64) | −4.57 (−10.09, 0.95) |
| | ApoC1 | −43.61 (−66.86, −20.35) | −36.94 (−58.1, −15.78) |
| | ApoC2 | 13.61 (−4.39, 31.62) | 12.6 (−4.68, 29.87) |
| | ApoC3 | 18.8 (−19.7, 57.3) | 5.27 (−27.05, 37.6) |
| | ApoC4 | 65.45 (−1099.3, 1230.2) | 1310.25 (115.72, 2504.78) |

Next, the model was tested in 35 replication samples. The correlation of the predicted cholesterol efflux with the cholesterol efflux measured in the laboratory was 0.86. Then, linear regression was applied to the proteins in this panel in another cohort of samples comprised of 76 fresh and frozen samples (40 fresh samples and 36 frozen samples). The model (Model 2) is shown in Table 36, and the correlation of the predicted cholesterol efflux with the cholesterol efflux measured in the laboratory was 0.55.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.77 based on 5-fold cross-validation. The models fitted to the healthy controls versus CAD patients with event had an area under the ROC curve (AUC) equals to 0.81 based on 5-fold cross-validation. The models fitted to the healthy controls versus CAD patients without event had an area under the ROC curve (AUC) equals to 0.72 based on 5-fold cross-validation. The values for the three CAD models are shown in Table 36 above. It is noted that the values in Table 36 also include a range for 95% confidence numbers. This range of numbers, for each value in the equations, could be substituted into the equations.

The predicted cholesterol efflux and CAD risk, calculated based on the five models and theree specific patients, are shown below in Table 37A.

TABLE 37A

Example of three samples on the five models

| SampleID | Group | Apo A1 | Apo C1 | Apo C2 | Apo C3 | Apo C4 | Model 1 results | Model 2 results | Model 3 results | Model 4 results | Model 5 results |
|---|---|---|---|---|---|---|---|---|---|---|---|
| P1 | Control | 3.50E−01 | 1.54E−01 | 1.05E−01 | 2.44E−02 | 7.76E−04 | 9.60E+00 | 1.93E+01 | −7.15E−01 | −1.75E+00 | −1.46E+00 |
| P2 | CAD without event | 5.04E−01 | 1.78E−01 | 1.64E−01 | 3.68E−02 | 1.10E−03 | 1.13E+01 | 2.31E+01 | −1.55E+00 | −3.23E+00 | −1.82E+00 |
| P3 | CAD with event | 3.50E−01 | 9.49E−02 | 7.43E−02 | 3.78E−02 | 6.25E−04 | 1.21E+01 | 1.74E+01 | 1.02E+00 | 6.48E−01 | 2.07E−01 |

The results in Table 37A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 37B for Models 1, 3, 4, and 5. These coefficients, as they are in molar amounts, may be used in the Models, where the proteins values are determined by any type of detection assay (e.g., ELISA, mass spec., etc.).

TABLE 37B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.57 (5.84, 9.29) | 4.37 (3.01, 5.73) | 5.62 (3.65, 7.59) | 2.69 (1.17, 4.2) |
| ApoA1 | −1.74 (−7.91, 4.42) | −7.09 (−10.89, −3.29) | −9.48 (−14.37, −4.59) | −5.75 (−10.32, −1.18) |
| ApoC1 | −9.76 (−44.58, 25.07) | −65.24 (−101.52, −28.96) | −82.61 (−129.37, −35.85) | −62 (−104.86, −19.14) |
| ApoC2 | 27.36 (−16.89, 71.61) | 21.78 (−11.05, 54.6) | 10.72 (−29.52, 50.96) | 31.97 (−7.82, 71.77) |
| ApoC3 | 146.76 (61.94, 231.57) | 8.37 (−29.78, 46.52) | 43.15 (0.44, 85.87) | −10.63 (−64.47, 43.21) |
| ApoC4 | −377.07 (−1160.53, 406.39) | 1285.3 (427.49, 2143.11) | 671.43 (−337.69, 1680.55) | 1586.75 (657.19, 2516.3) |

It is noted that the values in Table 37B also include a range for 95% confidence numbers. This range of numbers, for each value in the equations (Models), could be substituted into the equations.

Panel 19

Models 1-5 were developed for predicted global cholesterol efflux and CAD risk for Panel 19. Models 1-5 are shown below for Panel 19.

Models 1-5 for Panel 19=$(i)+(c1)*ApoA2+(c2)*ApoC1+(c3)*ApoC2+(c4)*ApoC3+(c5)*ApoD+(c6)*SAA1/2$ The values for Models 1-5 are shown in Table 38 below.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.74 based on 5-fold cross-validation. The models fitted to the healthy controls versus CAD patients with event had an area under the ROC curve (AUC) equals to 0.79 based on 5-fold cross-validation. The models fitted to the healthy controls versus CAD patients without event had an area under the ROC curve (AUC) equals to 0.73

TABLE 38

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| ApoA2 | 0.39 (−0.03, 0.81) | 1.82 (1.27, 2.38) | −0.32 (−0.67, 0.04) | −0.36 (−0.79, 0.08) | −0.32 (−0.76, 0.11) |
| ApoC1 | 8.19 (7.78, 8.61) | 29.35 (28.8, 29.91) | −39.56 (−56.59, −22.52) | −53.2 (−76.56, −29.85) | −38.33 (−57.68, −18.98) |
| ApoC2 | 9.04 (8.62, 9.45) | 28.01 (27.45, 28.57) | 20.54 (7.09, 33.99) | 22.17 (4.73, 39.6) | 23.78 (8.39, 39.17) |
| ApoC3 | 48.49 (48.07, 48.91) | 83.77 (83.21, 84.32) | 9.76 (−18.51, 38.02) | 6.4 (−29.36, 42.17) | 8.34 (−23.17, 39.85) |
| ApoD | 3.11 (2.7, 3.53) | 7.94 (7.38, 8.5) | −12.95 (−21.43, −4.48) | −17.96 (−29.2, −6.72) | −10.05 (−19.46, −0.65) |
| SAA1/2 | −112.43 (−112.85, −112.01) | 30.86 (30.3, 31.42) | 4.81 (−37.8, 47.43) | −0.34 (−67.5, 66.82) | 9.53 (−35.04, 54.1) |

Next, the model was tested in 35 replication samples. The correlation of the predicted cholesterol efflux with the cholesterol efflux measured in the laboratory was 0.71. Then, partial linear regression was applied to the proteins in this panel in another cohort of samples comprised of 76 fresh and frozen samples (40 fresh samples and 36 frozen samples). The values for model (Model 2) is shown in Table 38, and the correlation of the predicted cholesterol efflux with the cholesterol efflux measured in the laboratory was 0.51.

based on 5-fold cross-validation. The values for the three CAD models are shown in Table 38 above. It is noted that the values in Table 38 also include a range for 95% confidence numbers. This range of numbers, for each value in the equations, could be substituted into the equations.

The predicted cholesterol efflux and CAD risk, calculated based on the five models and there specific patients, are shown below in Table 39A.

TABLE 39A

Example of three samples on the five models

| Sample ID | Group | ApoA2 | ApoC1 | ApoC2 | ApoC3 | ApoD | SAA1/2 |
|---|---|---|---|---|---|---|---|
| P1 | Control | 5.65E+00 | 1.54E−01 | 1.05E−01 | 2.44E−02 | 2.18E−01 | 1.29E−04 |
| P2 | CAD without event | 3.70E+00 | 1.78E−01 | 1.64E−01 | 3.68E−02 | 2.40E−01 | 4.45E−04 |

TABLE 39A-continued

| | | Example of three samples on the five models | | | | | |
|---|---|---|---|---|---|---|---|
| P3 | CAD with event | 2.65E+00 | 9.49E−02 | 7.43E−02 | 3.78E−02 | 5.99E−02 | 1.14E−01 |

| Sample ID | Model1 | Model2 | Model3 | Model4 | Model5 |
|---|---|---|---|---|---|
| P1 | 1.08E+01 | 3.12E+01 | −1.77E+00 | −3.26E+00 | −2.19E+00 |
| P2 | 1.14E+01 | 3.38E+01 | −1.05E+00 | −2.86E+00 | −1.20E+00 |
| P3 | −3.80E+00 | 2.41E+01 | 3.62E+00 | 3.15E+00 | 3.10E+00 |

The results in Table 39A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 39B for Models 1, 3, 4, and 5. These coefficients, as they are in molar amounts, may be used in the Models, where the proteins values are determined by any type of detection assay (e.g., ELISA, mass spec., etc.).

Panel 20

Models 1-5 were developed for predicted global cholesterol efflux and CAD risk for Panel 20. Models 1-5 are shown below for Panel 20.

Models 1-5 for Panel $20=(i)+(c1)*\text{ApoA2}+(c2)*\text{ApoC3}+(c3)*\text{ApoD}+(c4)*\text{ApoE}+(c5)*\text{ApoL1}+(c6)*\text{PLTP}+(c7)*\text{SAA1/2}$ The values for Models 1-5 for Panel 20 are shown in Table 40 below.

TABLE 39B

| | Coefficients (95% CI) of the four models (based on molar values) | | | |
|---|---|---|---|---|
| Covariate | Model 1 on discovery samples | Model 3 on control vs. CAD samples | Model 4 on control vs. CAD with event samples | Model 5 on control vs. CAD without event samples |
| ApoA2 | 3.38 (2.95, 3.81) | 0.5 (−1.31, 2.31) | 0.64 (−1.12, 2.4) | 0.81 (−2.16, 3.78) |
| ApoC1 | 19.01 (18.58, 19.44) | −68.63 (−100.03, −37.23) | −97.53 (−140.37, −54.69) | −58.35 (−94.14, −22.56) |
| ApoC2 | 26.61 (26.18, 27.04) | 54.23 (21.36, 87.1) | 39.38 (−1.16, 79.91) | 65.05 (26.13, 103.97) |
| ApoC3 | 55.92 (55.49, 56.35) | −19.32 (−58.82, 20.18) | 1.47 (−44.46, 47.4) | −31.69 (−83.67, 20.29) |
| ApoD | 3.99 (3.56, 4.42) | −27.4 (−44.21, −10.59) | −29.8 (−50.41, −9.19) | −24.87 (−44.86, −4.88) |
| SAA1/2 | −23.05 (−23.48, −22.62) | 2.54 (−8.06, 13.13) | 1.82 (−9.76, 13.4) | 3.5 (−8.32, 15.32) |

It is noted that the values in Table 39B also include a range for 95% confidence numbers. This range of numbers, for each value in the equations (Models), could be substituted into the equations.

TABLE 40

| | Coefficients (95% CI) of the five models | | | | |
|---|---|---|---|---|---|
| Covariate | Model 1 on discovery samples | Model 2 on fresh/frozen samples | Model 3 on control vs. CAD samples | Model 4 on control vs. CAD with event samples | Model 5 on control vs. CAD without event samples |
| Intercept | 7.87 (4.9, 10.84) | 5.53 (1.58, 9.48) | 4.1 (2.19, 6.01) | 4.81 (2.45, 7.17) | 2.25 (0, 4.51) |
| ApoA2 | 0.05 (−0.35, 0.45) | 1.83 (−0.44, 4.1) | −0.13 (−0.62, 0.37) | −0.15 (−0.75, 0.45) | −0.08 (−0.66, 0.49) |
| ApoC3 | 132.35 (68.38, 196.33) | 134.26 (57.91, 210.62) | 12.48 (−10.8, 35.75) | 9.47 (−20.35, 39.28) | 12.94 (−13.6, 39.47) |
| ApoD | 2.46 (−4.11, 9.02) | −3.72 (−28.63, 21.2) | −12.82 (−20.92, −4.72) | −19.35 (−29.94, −8.76) | −8.83 (−18.06, 0.4) |
| ApoE | −434.37 (−1086.86, 218.12) | 2889.57 (483.26, 5295.88) | −1130.09 (−2120.32, −139.86) | −1298.28 (−2572.23, −24.33) | −1060.17 (−2202.84, 82.49) |
| ApoL1 | −82.96 (−217.27, 51.36) | 96.54 (−359.1, 552.17) | 4.2 (−120.12, 128.53) | −39.99 (−193.33, 113.36) | 61.21 (−78.56, 200.99) |
| PLTP | −4986.12 (−13380.42, 3408.17) | 12085.82 (−4740.01, 28911.65) | −5465.4 (−14442.87, 3512.08) | −5155.59 (−15865.07, 5553.89) | −5845.97 (−16137.78, 4445.84) |
| SAA1/2 | −107.12 (−256.25, 42.01) | 36.71 (−542.29, 615.71) | 13.79 (−34.79, 62.38) | 5.24 (−58.51, 68.99) | 22.75 (−33.6, 79.1) |

Next, the model was tested in 35 replication samples. The correlation of the predicted cholesterol efflux with the cholesterol efflux measured in the laboratory was 0.8. Then, elastic net model was applied to the proteins in this panel in another cohort of samples comprised of 76 fresh and frozen samples (40 fresh samples and 36 frozen samples). The model (Model 2) is shown in Table 40 above, and the correlation of the predicted cholesterol efflux with the cholesterol efflux measured in the laboratory was 0.52.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.64 based on 5-fold cross-validation. The models fitted to the healthy controls versus CAD patients with event had an area under the ROC curve (AUC) equals to 0.68 based on 5-fold cross-validation. The models fitted to the healthy controls versus CAD patients without event had an area under the ROC curve (AUC) equals to 0.66 based on 5-fold cross-validation. The values for the three CAD models are shown in Table 40 above. It is noted that the values in Table 40 also include a range for 95% confidence numbers. This range of numbers, for each value in the equations, could be substituted into the equations.

The predicted cholesterol efflux and CAD risk, calculated based on the five models and three specific patients, are shown below in Table 41.

TABLE 41

Example of three samples on the five models

| Sample ID | Group | Apo A2 | Apo C3 | Apo D | Apo E | Apo L1 | PLT P |
|---|---|---|---|---|---|---|---|
| P1 | Control | 5.65E+00 | 2.44E−02 | 2.18E−01 | 1.43E−03 | 4.77E−03 | 2.15E−04 |
| P2 | CAD without event | 3.70E+00 | 3.68E−02 | 2.40E−01 | 9.11E−04 | 5.14E−03 | 1.42E−04 |
| P3 | CAD with event | 2.65E+00 | 3.78E−02 | 5.99E−02 | 3.61E−04 | 7.38E−03 | 1.00E−04 |

| Sample ID | SAA 1/2 | Model 1 results | Model 2 results | Model 3 results | Model 4 results | Model 5 results |
|---|---|---|---|---|---|---|
| P1 | 1.29E−04 | 9.82E+00 | 1.90E+04 | −1.88E+00 | −3.19E+00 | −2.30E+00 |
| P2 | 4.45E−04 | 1.19E+01 | 1.36E+04 | −7.67E−01 | −2.16E+00 | −1.17E+00 |
| P3 | 1.14E−01 | −3.58E−01 | 8.39E+03 | 4.12E+00 | 2.93E+00 | 4.08E+00 |

The results in Table 41A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 41B for Models 1, 3, 4, and 5. These coefficients, as they are in molar amounts, may be used in the Models, where the proteins values are determined by any type of detection assay (e.g., ELISA, mass spec., etc.).

TABLE 41B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.8 (5.67, 9.94) | 3.83 (2.32, 5.33) | 3.9 (2.15, 5.65) | 2.35 (0.58, 4.12) |
| ApoA2 | 0 (−5.48, 5.48) | 0.15 (−0.82, 1.12) | 0.36 (−0.73, 1.45) | −0.86 (−3.69, 1.97) |
| ApoC3 | 142.43 (97.75, 187.11) | −11.38 (−38.82, 16.06) | −15.71 (−48.09, 16.67) | 0.49 (−36.72, 37.71) |
| ApoD | 3.11 (−6.64, 12.87) | −22.31 (−39.07, −5.55) | −25.69 (−46.76, −4.61) | −18.25 (−39.42, 2.93) |
| ApoE | 13.26 (−4.03, 30.55) | 4.44 (−1.96, 10.83) | 3.78 (−4.37, 11.92) | 4.93 (−2.25, 12.11) |
| ApoL1 | −186.24 (−1416.44, 1043.97) | −726.21 (−2150.56, 698.14) | −1331.26 (−3040.53, 378) | 55.96 (−1596.8, 1708.72) |
| PLTP | −777.72 (−1785.7, 230.25) | −1144.44 (−2156.88, −132.01) | −1336.09 (−2581.63, −90.55) | −1057.96 (−2314.7, 198.77) |
| SAA1/2 | −37.78 (−68.51, −7.06) | 5.3 (−9.04, 19.65) | 4.84 (−8.75, 18.43) | 6.73 (−9.76, 23.22) |

It is noted that the values in Table 41B also include a range for 95% confidence numbers. This range of numbers, for each value in the equations (Models), could be substituted into the equations.

Panel 21

Models 1-5 were developed for predicted global cholesterol efflux and CAD risk for Panel 21. Models 1-5 are shown below for Panel 21.

Models 1-5 for Panel 21=$(i)+(c1)*$ApoC3+$(c2)*$ApoM+$(c3)*$PLTP+$(c4)*$SAA1/2

The values for Models 1-5 for Panel 21 are shown in Table 42 below.

to 0.71 based on 5-fold cross-validation. The models fitted to the healthy controls versus CAD patients without event had an area under the ROC curve (AUC) equals to 0.68 based on 5-fold cross-validation. The values for the three CAD models are shown in Table 42 above. It is noted that the values in Table 42 also include a range for 95% confidence numbers. This range of numbers, for each value in the equations, could be substituted into the equations.

The predicted cholesterol efflux and CAD risk, calculated based on the five models and three specific patients, are shown below in Table 43A.

TABLE 42

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 8.9 | 6.91 | 2.95 | 3.07 | 1.69 |
|  | (6.86, 10.94) | (4, 9.83) | (1.87, 4.04) | (1.71, 4.43) | (0.49, 2.88) |
| ApoC3 | 159.3 | 256.74 | 21 | 21.68 | 22.24 |
|  | (120.77, 197.83) | (148.1, 365.39) | (−1.25, 43.25) | (−7.15, 50.51) | (−2.84, 47.33) |
| ApoM | −2372.51 | 1937.16 | −1965.34 | −2882.06 | −1450.22 |
|  | (−5724.51, 979.5) | (−4207.42, 8081.74) | (−3113.1, −817.58) | (−4430.18, −1333.95) | (−2729.42, −171.03) |
| PLTP | −11775.35 | 11437.74 | −8579.9 | −8907.23 | −8221.48 |
|  | (−22050.84, −1499.86) | (−11380.77, 34256.24) | (−14673.88, −2485.93) | (−15983.2, −1831.26) | (−15280.73, −1162.24) |
| SAA1/2 | −210.75 | −27.45 | 12.02 | 3.88 | 23.12 |
|  | (−451.24, 29.74) | (−309.43, 254.53) | (−33.15, 57.18) | (−50.99, 58.75) | (−34.78, 81.01) |

Next, the model was tested in 35 replication samples. The correlation of the predicted cholesterol efflux with the cholesterol efflux measured in the laboratory was 0.76. Then, robust linear regression was applied to the proteins in this panel in another cohort of samples comprised of 76 fresh and

TABLE 43A

Example of three samples on the five models

| Sample ID | Group | ApoC3 | ApoM | PLTP | SAA1/2 | Model 1 results | Model 2 results | Model 3 results | Model 4 results | Model 5 results |
|---|---|---|---|---|---|---|---|---|---|---|
| P1 | Control | 2.44E−02 | 1.10E−03 | 2.15E−04 | 1.29E−04 | 7.61E+00 | 1.78E+01 | −5.45E−01 | −1.49E+00 | −1.14E+00 |
| P2 | CAD without event | 3.68E−02 | 5.98E−04 | 1.42E−04 | 4.45E−04 | 1.16E+01 | 1.91E+01 | 1.34E+00 | 8.87E−01 | 4.83E−01 |
| P3 | CAD with event | 3.78E−02 | 3.12E−04 | 1.00E−04 | 1.14E−01 | −1.11E+01 | 1.52E+01 | 3.65E+00 | 2.54E+00 | 3.89E+00 | frozen samples (40 fresh samples and 36 frozen samples). The model (Model 2) is shown above in Table 42, and the correlation of the predicted cholesterol efflux with the cholesterol efflux measured in the laboratory was 0.5.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.65 based on 5-fold cross-validation. The models fitted to the healthy controls versus CAD patients with event had an area under the ROC curve (AUC) equals The results in Table 43A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 43B for Models 1, 3, 4, and 5. These coefficients, as they are in molar amounts, may be used in the Models, where the proteins values are determined by any type of detection assay (e.g., ELISA, mass spec., etc.).

TABLE 43B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
| --- | --- | --- | --- | --- |
| Intercept | 8.89 (7.14, 10.63) | 2.74 (1.62, 3.87) | 2.65 (1.31, 4) | 1.62 (0.32, 2.92) |
| ApoC3 | 171.62 (127.64, 215.6) | −5.84 (−31.73, 20.06) | −7.41 (−36.96, 22.15) | −2.89 (−31.53, 25.75) |
| ApoM | −1310.78 (−3062.6, 441.03) | −55.04 (−317.6, 207.52) | −176.58 (−512.43, 159.27) | 48.81 (−258.23, 355.86) |
| PLTP | −970.7 (−1971.99, 30.6) | −1509.22 (−2445.77, −572.67) | −1773.61 (−2914.32, −632.9) | −1419.51 (−2544.94, −294.08) |
| SAA1/2 | −44.52 (−90.11, 1.06) | 5.57 (−7.73, 18.87) | 5.57 (−6.6, 17.73) | 7.11 (−9.93, 24.15) |

It is noted that the values in Table 43B also include a range for 95% confidence numbers. This range of numbers, for each value in the equations (Models), could be substituted into the equations.

Panel 22

Models 1-5 were developed for predicted global cholesterol efflux and CAD risk for Panel 22. Models 1-5 are shown below for Panel 22.

Models 1-5 for Panel 22=$(i)+(c1)*ApoC3+(c2)*ApoD+(c3)*PLTP+(c4)*SAA1/2$

The values for Models 1-5 are shown in Table 44 below.

TABLE 44

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
| --- | --- | --- | --- | --- | --- |
| Intercept | 7.54 (5.75, 9.33) | 6.59 (3.35, 9.82) | 3.63 (2.33, 4.92) | 3.98 (2.32, 5.65) | 2.16 (0.72, 3.61) |
| ApoC3 | 149.56 (113.47, 185.65) | 269.48 (164.91, 374.05) | 7.09 (−13.67, 27.84) | 0.16 (−25.96, 26.27) | 11.63 (−12, 35.26) |
| ApoD | 4.28 (−2.81, 11.36) | 9.11 (−20.52, 38.73) | −14.26 (−22.08, −6.44) | −20.3 (−30.63, −9.96) | −10.23 (−19.15, −1.31) |
| PLTP | −11139.66 (−21514.27, −765.05) | 10475.88 (−12872.35, 33824.1) | −8626.73 (−14650.77, −2602.7) | −8836.22 (−15958.19, −1714.24) | −8318.95 (−15379.88, −1258.03) |
| SAA1/2 | −173.97 (−421.48, 73.54) | −53.55 (−329.31, 222.22) | 14.91 (−35.78, 65.59) | 5.41 (−48.63, 59.46) | 27.4 (−34.87, 89.67) |

Next, the model was tested in 35 replication samples. The correlation of the predicted cholesterol efflux with the cholesterol efflux measured in the laboratory was 0.79. Then, robust linear regression was applied to the proteins in this panel in another cohort of samples comprised of 76 fresh and frozen samples (40 fresh samples and 36 frozen samples). The model (Model 2) is shown in Table 44 above, and the correlation of the predicted cholesterol efflux with the cholesterol efflux measured in the laboratory was 0.5.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.65 based on 5-fold cross-validation. The models fitted to the healthy controls versus CAD patients with event had an area under the ROC curve (AUC) equals to 0.71 based on 5-fold cross-validation. The models fitted to the healthy controls versus CAD patients without event had an area under the ROC curve (AUC) equals to 0.66 based on 5-fold cross-validation. The values for the three CAD models are shown in Table 44 above. It is noted that the values in Table 44 also include a range for 95% confidence numbers. This range of numbers, for each value in the equations, could be substituted into the equations.

The predicted cholesterol efflux and CAD risk, calculated based on the five models and three specific patients, are shown below in Table 45A.

TABLE 45A

Example of three samples on the five models

| Sample ID | Group | ApoC3 | ApoD | PLTP | SAA1/2 | Model 1 results | Model 2 results | Model 3 results | Model 4 results | Model 5 results |
| --- | --- | --- | --- | --- | --- | --- | --- | --- | --- | --- |
| P1 | Control | 2.44E−02 | 2.18E−01 | 2.15E−04 | 1.29E−04 | 9.71E+00 | 1.74E+01 | −1.17E+00 | −2.34E+00 | −1.57E+00 |
| P2 | CAD without event | 3.68E−02 | 2.40E−01 | 1.42E−04 | 4.45E−04 | 1.24E+01 | 2.01E+01 | −7.54E−01 | −2.14E+00 | −1.03E+00 |
| P1 | CAD with event | 3.78E−02 | 5.99E−02 | 1.00E−04 | 1.14E−01 | −7.55E+00 | 1.22E+01 | 3.88E+00 | 2.51E+00 | 4.29E+00 |

The results in Table 45A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 45B for Models 1, 3, 4, and 5. These coefficients, as they are in molar amounts, may be used in the Models, where the proteins values are determined by any type of detection assay (e.g., ELISA, mass spec., etc.).

elastic net model was applied to the proteins in this panel in another cohort of samples comprised of 76 fresh and frozen samples (40 fresh samples and 36 frozen samples). The model (Model 2) is shwon in Table 46 above, and the correlation of the predicted cholesterol efflux with the cholesterol efflux measured in the laboratory was 0.5.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve

TABLE 45B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.8 (6.25, 9.34) | 3.44 (2.14, 4.74) | 3.4 (1.85, 4.95) | 2.22 (0.72, 3.72) |
| ApoC3 | 156.74 (115.72, 197.76) | −9.45 (−35.19, 16.28) | −13.19 (−43.59, 17.2) | −4.67 (−33.44, 24.1) |
| ApoD | 5.05 (−4.92, 15.02) | −21.46 (−37.75, −5.17) | −26.13 (−46.67, −5.59) | −18.07 (−38.2, 2.05) |
| PLTP | −1092.76 (−2100.91, −84.61) | −1044.54 (−2027.5, −61.57) | −1277.05 (−2492.9, −61.2) | −894.67 (−2073.84, 284.5) |
| SAA1/2 | −40.3 (−86.85, 6.25) | 4.27 (−8.51, 17.06) | 3.4 (−8.74, 15.54) | 6.08 (−9.86, 22.01) |

It is noted that the values in Table 45B also include a range for 95% confidence numbers. This range of numbers, for each value in the equations (Models), could be substituted into the equations.

Panel 23

Models 1-5 were developed for predicted global cholesterol efflux and CAD risk for Panel 23. Models 1-5 are shown below for Panel 23.

Models 1-5 for Panel 23=$(i)+(c1)*$ApoA2+$(c2)$
$*$ApoC3+$(c3)*$ApoD+$(c4)*$ApoL1+$(c5)*$ApoM+
$(c6)*$PLTP+$(c7)*$SAA1/2

The values for Models 1-5 are shown in Table 46 below.

(AUC) equals to 0.65 based on 5-fold cross-validation. The models fitted to the healthy controls versus CAD patients with event had an area under the ROC curve (AUC) equals to 0.7 based on 5-fold cross-validation. The models fitted to the healthy controls versus CAD patients without event had an area under the ROC curve (AUC) equals to 0.67 based on 5-fold cross-validation. The values for the three CAD models are shown in Table 46 above. It is noted that the values in Table 46 also include a range for 95% confidence numbers. This range of numbers, for each value in the equations, could be substituted into the equations.

TABLE 46

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 7.8 (4.78, 10.83) | 6.02 (1.89, 10.14) | 3.59 (1.68, 5.51) | 4.24 (1.89, 6.6) | 1.72 (−0.57, 4) |
| ApoA2 | 0.09 (−0.3, 0.48) | 1.8 (−0.7, 4.31) | 0.12 (−0.41, 0.66) | 0.14 (−0.5, 0.78) | 0.18 (−0.46, 0.81) |
| ApoC3 | 129.5 (66.77, 192.24) | 165.77 (80.42, 251.13) | 15.8 (−7.97, 39.56) | 16.77 (−15.33, 48.86) | 14.04 (−12.9, 40.97) |
| ApoD | 2.78 (−4.07, 9.64) | −0.72 (−27.04, 25.6) | −10.8 (−19.25, −2.34) | −16.01 (−27.26, −4.76) | −7.14 (−16.73, 2.46) |
| ApoL1 | −105.53 (−250.84, 39.77) | 136.67 (−350.87, 624.22) | 12.99 (−113.57, 139.54) | −26.68 (−184.18, 130.82) | 67.1 (−75.29, 209.49) |
| ApoM | −60.55 (−2293.35, 2172.26) | 697.31 (−3710.76, 5105.39) | −1564.08 (−2800.87, −327.28) | −2141.95 (−3843.94, −439.96) | −1332.6 (−2741.53, 76.32) |
| PLTP | −6467.7 (−15383.7, 2448.29) | 10450.7 (−8039.24, 28940.64) | −8823.4 (−17920.23, 273.43) | −9159.88 (−20241.26, 1921.5) | −9432.79 (−19925.98, 1060.39) |
| SAA1/2 | −107.69 (−264.07, 48.69) | 53.63 (−589.84, 697.1) | 11.11 (−34.85, 57.07) | 3.05 (−59.28, 65.39) | 19.62 (−34.23, 73.48) |

Next, the model was tested in 35 replication samples. The correlation of the predicted cholesterol efflux with the cholesterol efflux measured in the laboratory was 0.79. Then, The predicted cholesterol efflux and CAD risk, calculated based on the five models and three specific patients, are shown below in Table 47A.

TABLE 47A

Example of three samples on the five models

| Sample ID | Group | Apo A2 | Apo C3 | Apo D | Apo L1 | ApoM | PLTP |
|---|---|---|---|---|---|---|---|
| P1 | Control | 5.65E+00 | 2.44E-02 | 2.18E-01 | 4.77E-03 | 1.10E-03 | 2.15E-04 |
| P2 | CAD without event | 3.70E+00 | 3.68E-02 | 2.40E-01 | 5.14E-03 | 5.98E-04 | 1.42E-04 |
| P3 | CAD with event | 2.65E+00 | 3.78E-02 | 5.99E-02 | 7.38E-03 | 3.12E-04 | 1.00E-04 |

| Sample ID | SAA1/2 | Model 1 Res. | Model 2 Res. | Model 3 Res. | Model 4 Res. | Model 5 Res. |
|---|---|---|---|---|---|---|
| P1 | 1.29E-04 | 1.01E+01 | 2.30E+03 | -1.26E+00 | -2.53E+00 | -1.68E+00 |
| P2 | 4.45E-04 | 1.20E+01 | 2.53E+03 | -8.88E-02 | -1.19E+00 | -6.09E-01 |
| P3 | 1.14E-01 | -6.49E-01 | 7.23E+02 | 3.85E+00 | 2.85E+00 | 3.66E+00 |

The results in Table 47A may be used to generate a probability of CAD based on the formula that: Probability=1/(1+exp(-risk score)).

As described above, the absolute molar amounts of each protein was determined using the absolute amount of the internal standard. These molar amounts were then used to determine the coefficients in Table 47B for Models 1, 3, 4, and 5. These coefficients, as they are in molar amounts, may be used in the Models, where the proteins values are determined by any type of detection assay (e.g., ELISA, mass spec., etc.).

Panel 24

Models 1-5 were developed for predicted global cholesterol efflux and CAD risk for Panel 24. Models 1-5 are shown below for Panel 24.

Models 1-5 for Panel 24=$(i)+(c1)*\text{ApoC1}+(c2)*\text{ApoC3}+(c3)*\text{SAA1/2}$ The values for Models 1-5 are shown in Table 48 below.

TABLE 47B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 8.58 (6.28, 10.87) | 3.8 (2.31, 5.3) | 4.01 (2.26, 5.76) | 2.18 (0.44, 3.93) |
| ApoA2 | 0 (-5.93, 5.93) | 0.16 (-0.84, 1.15) | 0.36 (-0.75, 1.46) | -0.86 (-3.65, 1.92) |
| ApoC3 | 155.56 (110.67, 200.45) | -8.57 (-36.14, 19) | -11.27 (-43.51, 20.97) | 1.91 (-35.02, 38.84) |
| ApoD | 2.73 (-7.63, 13.08) | -23.11 (-39.79, -6.43) | -28.39 (-49.38, -7.39) | -17.5 (-38.52, 3.52) |
| ApoL1 | -379.85 (-1727.88, 968.19) | -706.54 (-2115.61, 702.53) | -1253.66 (-2949.83, 442.51) | 125.73 (-1513.4, 1764.85) |
| ApoM | -639.21 (-2072.68, 794.26) | -76.28 (-344.63, 192.06) | -199.42 (-545.72, 146.87) | 44.43 (-270.73, 359.58) |
| PLTP | -838.3 (-1842.66, 166.05) | -905.77 (-1942.54, 131) | -986.87 (-2276.44, 302.7) | -954.37 (-2248.03, 339.29) |
| SAA1/2 | -34.47 (-68.64, -0.31) | 4.64 (-9.14, 18.42) | 4.03 (-9.55, 17.61) | 6.23 (-9.86, 22.32) |

It is noted that the values in Table 47B also include a range for 95% confidence numbers. This range of numbers, for each value in the equations (Models), could be substituted into the equations.

TABLE 48

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 7.38 (6.15, 8.61) | 7.11 (4.99, 9.22) | 3.34 (2.16, 4.53) | 4.24 (2.57, 5.9) | 1.92 (0.61, 3.23) |
| ApoC1 | -10.85 (-24.16, 2.47) | 59.54 (18.32, 100.76) | -27.75 (-38.39, -17.11) | -39.78 (-54.8, -24.76) | -21.85 (-33.74, -9.96) |
| ApoC3 | 160 (114.1, 205.89) | 125.26 (-1.86, 252.39) | 27.91 (4.07, 51.74) | 25.36 (-3.15, 53.86) | 26.53 (0.26, 52.8) |
| SAA1/2 | -252 (-496.72, -7.29) | -16.22 (-278.3, 245.86) | 16.99 (-36.25, 70.23) | 16.48 (-51.79, 84.76) | 23.91 (-36.6, 84.41) |

Next, the model was tested in 35 replication samples. The correlation of the predicted cholesterol efflux with the cholesterol efflux measured in the laboratory was 0.85. Then, linear regression was applied to the proteins in this panel in another cohort of samples comprised of 76 fresh and frozen samples (40 fresh samples and 36 frozen samples). The model (Model 2) is shown in Table 48 above, and the correlation of the predicted cholesterol efflux with the cholesterol efflux measured in the laboratory was 0.53.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.7 based on 5-fold cross-validation. The models fitted to the healthy controls versus CAD patients with event had an area under the ROC curve (AUC) equals to 0.75 based on 5-fold cross-validation. The models fitted to the healthy controls versus CAD patients without event had an area under the ROC curve (AUC) equals to 0.67 based on 5-fold cross-validation. The values for the three CAD models are shown in Table 48 above. It is noted that the values in Table 48 also include a range for 95% confidence numbers. This range of numbers, for each value in the equations, could be substituted into the equations.

The predicted cholesterol efflux and CAD risk, calculated based on the five models and three specific patients, are shown below in Table 49A.

TABLE 49A

Example of three samples on the five models

| Sample ID | Group | ApoC1 | ApoC3 | SAA1/2 | Model 1 results | Model 2 results | Model 3 results | Model 4 results | Model 5 resulst |
|---|---|---|---|---|---|---|---|---|---|
| P1 | Control | 1.54E−01 | 2.44E−02 | 1.29E−04 | 9.59E+00 | 1.93E+01 | −2.46E−01 | −1.27E+00 | −7.91E−01 |
| P2 | CAD without event | 1.78E−01 | 3.68E−02 | 4.45E−04 | 1.12E+01 | 2.23E+01 | −5.62E−01 | −1.90E+00 | −9.80E−01 |
| P3 | CAD with event | 9.49E−02 | 3.78E−02 | 1.14E−01 | −1.64E+01 | 1.56E+01 | 3.71E+00 | 3.30E+00 | 3.58E+00 |

The results in Table 49A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 49B for Models 1, 3, 4, and 5. These coefficients, as they are in molar amounts, may be used in the Models, where the proteins values are determined by any type of detection assay (e.g., ELISA, mass spec., etc.).

TABLE 49B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.39 (6.15, 8.63) | 2.72 (1.69, 3.76) | 3.53 (2.09, 4.97) | 1.27 (0.13, 2.41) |
| ApoC1 | −12.68 (−42.17, 16.82) | −47.8 (−71.65, −23.95) | −85.05 (−120.22, −49.88) | −29.86 (−56.28, −3.45) |
| ApoC3 | 160.28 (106.7, 213.85) | 16.56 (−14.01, 47.14) | 29.83 (−5.37, 65.03) | 9.86 (−23.71, 43.44) |
| SAA1/2 | −52.2 (−99.26, −5.13) | 4.2 (−8.22, 16.63) | 4.3 (−7.71, 16.31) | 5.23 (−9.94, 20.39) |

It is noted that the values in Table 49B also include a range for 95% confidence numbers. This range of numbers, for each value in the equations (Models), could be substituted into the equations.

Panel 25

Models 1-5 were developed for predicted global cholesterol efflux and CAD risk for Panel 25. Models 1-5 are shown below for Panel 25.

Models 1-5 for Panel 25=$(i)+(c1)*ApoC1+(c2)*ApoC3+(c3)*C3+(c4)*PLTP$

The values for Models 1-5 are shown in Table 50 below.

TABLE 50

Coefficients (95% CI) of the five models

| Covariate | Model 1 on discovery samples | Model 2 on fresh/frozen samples | Model 3 on control vs. CAD samples | Model 4 on control vs. CAD with event samples | Model 5 on control vs. CAD without event samples |
|---|---|---|---|---|---|
| Intercept | 7.99 (5.69, 10.3) | 4.84 (1.14, 8.55) | 3.64 (2.27, 5.01) | 4.81 (2.83, 6.79) | 2.23 (0.78, 3.68) |
| ApoC1 | −5.19 (−19.86, 9.48) | 57.45 (17.34, 97.56) | −29.93 (−42.06, −17.81) | 45.46 (−62.5, −28.43) | −23.33 (−37.05, −9.6) |
| ApoC3 | 164.8 (115.65, 213.95) | 142.21 (15.89, 268.53) | 47.2 (19.66, 74.74) | 53.36 (19.38, 87.33) | 42.25 (12.07, 72.43) |
| C3 | −1.48 (−22.53, 19.58) | 13.35 (−28.68, 55.38) | 13.03 (1.7, 24.37) | 18.04 (3.48, 32.59) | 11.46 (−1.12, 24.03) |
| PLTP | −9945.86 (−21229.79, 1338.07) | 8814.59 (−12205.2, 29834.38) | −9058.99 (−15370.55, −2747.43) | −11783.35 (−19456.32, −4110.38) | −8151.62 (−15335.03, −968.21) |

Next, the model was tested in 35 replication samples. The correlation of the predicted cholesterol efflux with the cholesterol efflux measured in the laboratory was 0.79. Then, robust linear regression was applied to the proteins in this panel in another cohort of samples comprised of 76 fresh and frozen samples (40 fresh samples and 36 frozen samples). The model (Model 2) is shown in Table 50, and the correlation of the predicted cholesterol efflux with the cholesterol efflux measured in the laboratory was 0.56.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.74 based on 5-fold cross-validation. The models fitted to the healthy controls versus CAD patients with event had an area under the ROC curve (AUC) equals to 0.8 based on 5-fold cross-validation. The models fitted to the healthy controls versus CAD patients without event had an area under the ROC curve (AUC) equals to 0.7 based on 5-fold cross-validation. The values for the three CAD models are shown in Table 50 above. It is noted that the values in Table 50 also include a range for 95% confidence numbers. This range of numbers, for each value in the equations, could be substituted into the equations.

The predicted cholesterol efflux and CAD risk, calculated based on the five models and three specific patients, are shown below in Table 51A.

TABLE 51A

Example of three samples on the five models

| Sample ID | Group | ApoC1 | ApoC3 | C3 | PLTP | Model 1 | Model 2 results | Model 3 results | Model 4 results | Model 5 results |
|---|---|---|---|---|---|---|---|---|---|---|
| P1 | Control | 1.54E−01 | 2.44E−02 | 6.57E−02 | 2.15E−04 | 8.98E+00 | 1.99E+01 | −9.11E−01 | −2.24E+00 | −1.33E+00 |
| P2 | CAD without event | 1.78E−01 | 3.68E−02 | 3.51E−02 | 1.42E−04 | 1.17E+01 | 2.20E+01 | −7.78E−01 | −2.36E+00 | −1.12E+00 |
| P3 | CAD with event | 9.49E−02 | 3.78E−02 | 3.61E−02 | 1.00E−04 | 1.27E+01 | 1.70E+01 | 2.15E+00 | 1.98E+00 | 1.21E+00 |

The results in Table 51A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 51B for Models 1, 3, 4, and 5. These coefficients, as they are in molar amounts, may be used in the Models, where the proteins values are determined by any type of detection assay (e.g., ELISA, mass spec., etc.).

TABLE 51B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 7.51 (5.82, 9.2) | 3.24 (1.79, 4.69) | 3.99 (2.02, 5.96) | 2.21 (0.61, 3.82) |
| ApoC1 | 4.42 (−27.02, 35.87) | −39.44 (−65.8, −13.08) | −78.58 (−115.31, −41.84) | −18.19 (−48.4, 12.02) |
| ApoC3 | 157.61 (103.64, 211.59) | 19.45 (−13.28, 52.17) | 37.82 (1.12, 74.52) | 6.1 (−29.17, 41.38) |

TABLE 51B-continued

| | Coefficients (95% CI) of the four models (based on molar values) | | | |
|---|---|---|---|---|
| Covariate | Model 1 on discovery samples | Model 3 on control vs. CAD samples | Model 4 on control vs. CAD with event samples | Model 5 on control vs. CAD without event samples |
| C3 | 77.14 (−109.45, 263.74) | 22.56 (−83.62, 128.74) | 68.46 (−52.98, 189.9) | −28.98 (−155.9, 97.94) |
| PLTP | −1388.99 (−2586.94, −191.04) | −926.63 (−1931.61, 78.34) | −1111.44 (−2324.08, 101.2) | −1068.27 (−2261.36, 124.82) |

It is noted that the values in Table 51B also include a range for 95% confidence numbers. This range of numbers, for each value in the equations (Models), could be substituted into the equations.

Panel 26

Models 1-5 were developed for predicted global cholesterol efflux and CAD risk for Panel 26. Models 1-5 are shown below for Panel 26.

Models 1-5 for Panel 26=($i$)+($c1$)*ApoA2+($c2$)
*ApoC2+($c3$)*ApoC3+($c4$)*ApoD+($c5$)*ApoE+
($c6$)*ApoL1+($c7$)*ApoM+($c8$)*CETP+($c9$)
*CLU+($c10$)*PLTP+($c11$)*POND+($c12$)
*SAA1/2

The values for Models 1-5 are shown below in Table 52.

correlation of the predicted cholesterol efflux with the cholesterol efflux measured in the laboratory was 0.62.

Last, logistic regression was applied to the proteins in this panel in another cohort of samples comprised of 74 healthy controls and 157 CAD patients (83 with event and 74 without event). The models fitted to the healthy control versus CAD patients had an area under the ROC curve (AUC) equals to 0.63 based on 5-fold cross-validation. The models fitted to the healthy controls versus CAD patients with event had an area under the ROC curve (AUC) equals to 0.71 based on 5-fold cross-validation. The models fitted to the healthy controls versus CAD patients without event had an area under the ROC curve (AUC) equals to 0.6 based on 5-fold cross-validation. The values for the three CAD

TABLE 52

| | Coefficients (95% CI) of the five models | | | | |
|---|---|---|---|---|---|
| Covariate | Model 1 on discovery samples | Model 2 on fresh/frozen samples | Model 3 on control vs. CAD samples | Model 4 on control vs. CAD with event samples | Model 5 on control vs. CAD without event samples |
| Intercept | 8.09 (4.41, 11.76) | 3.27 (−0.59, 7.13) | 3.56 (1.42, 5.71) | 4.89 (2.01, 7.76) | 1.84 (−0.65, 4.34) |
| ApoA2 | 0.29 (−0.25, 0.84) | 1.73 (−0.4, 3.86) | 0.23 (−0.37, 0.83) | 0.24 (−0.53, 1.01) | 0.19 (−0.5, 0.88) |
| ApoC2 | 5.74 (−3.88, 15.36) | 25.33 (−1.31, 51.97) | 1.32 (−8.77, 11.42) | −6.44 (−19.32, 6.45) | 5.8 (−5.47, 17.07) |
| ApoC3 | 116.82 (53.7, 179.94) | 68.43 (−7.49, 144.35) | 14.19 (−16.72, 45.1) | 26.18 (−14.48, 66.83) | 4.55 (−29.64, 38.75) |
| ApoD | 4.88 (−3.17, 12.93) | −4.21 (−26.37, 17.95) | −10.09 (−19.16, −1.02) | −11.89 (−24.01, 0.22) | −8.03 (−18.3, 2.23) |
| ApoE | −653.75 (−1373.22, 65.73) | 2141.55 (−114.11, 4397.21) | −1091.63 (−2206.18, 22.93) | −848.51 (−2274.98, 577.96) | −1211 (−2514.72, 92.72) |
| ApoL1 | −129.86 (−280.53, 20.8) | 27.11 (−398.91, 453.13) | 32.55 (−102.35, 167.45) | −3.7 (−177.76, 170.36) | 97.37 (−55.1, 249.84) |
| ApoM | −504.26 (−3465.07, 2456.54) | −913.66 (−4605.33, 2778) | −1398.89 (−2688.13, −109.65) | −2174.9 (−3968.34, −381.46) | −1059.99 (−2508.99, 389) |
| CETP | 205.39 (−1300.46, 1711.24) | −1127.5 (−4594.65, 2339.66) | 68.74 (−289.36, 426.84) | −2880.68 (−6681.2, 919.84) | 107.43 (−292.2, 507.07) |
| CLU | −5.36 (−24.5, 13.78) | 66.38 (35.47, 97.29) | 3.77 (−24.36, 31.9) | 15.24 (−20.62, 51.1) | 0.11 (−31.87, 32.09) |
| PLTP | −8940.64 (−18311.97, 430.68) | 6025.55 (−9504.23, 21555.34) | −6916.83 (−16363.65, 2530) | −6683.39 (−18720.06, 5353.28) | −6611.91 (−17796.33, 4572.51) |
| PON1 | −20.38 (−80.41, 39.64) | −31.38 (−195.94, 133.17) | −60.81 (−170.92, 49.31) | −68.58 (−204.76, 67.61) | −42.07 (−168.23, 84.08) |
| SAA1/2 | −115.03 (−283, 52.95) | −12.67 (−590.58, 565.24) | 9.33 (−31.75, 50.42) | 8.05 (−59.22, 75.33) | 14.43 (−27.48, 56.35) |

Next, the model was tested in 35 replication samples. The correlation of the predicted cholesterol efflux with the cholesterol efflux measured in the laboratory was 0.78. Then, elastic net model was applied to the proteins in this panel in another cohort of samples comprised of 76 fresh and frozen samples (40 fresh samples and 36 frozen samples). The model (Model 2) is shown in Table 52 above, and the models are shown in Table 52 above. It is noted that the values in Table 52 also include a range for 95% confidence numbers. This range of numbers, for each value in the equations, could be substituted into the equations.

The predicted cholesterol efflux and CAD risk, calculated based on the five models and three specific patients, are shown below in Table 53A.

TABLE 53A

Example of three samples on the five models

| Sam. ID | Group | ApoA2 | ApoC2 | ApoC3 | ApoD | ApoE | ApoL1 | ApoM | CETP | CLU |
|---|---|---|---|---|---|---|---|---|---|---|
| P1 | Control | 5.65E+00 | 1.05E−01 | 2.44E−02 | 2.18E−01 | 1.43E−03 | 4.77E−03 | 1.10E−03 | 6.09E−04 | 7.31E−02 |
| P2 | CAD without event | 3.70E+00 | 1.64E−01 | 3.68E−02 | 2.40E−01 | 9.11E−04 | 5.14E−03 | 5.98E−04 | 6.00E−04 | 7.72E−02 |
| P3 | CAD with event | 2.65E+00 | 7.43E−02 | 3.78E−02 | 5.99E−02 | 3.61E−04 | 7.38E−03 | 3.12E−04 | 5.57E−04 | 5.18E−02 |

| Sam. ID | PLTP | PON1 | SAA1/2 | Mod. 1 res. | Mod. 2 res. | Mod. 3 res. | Model 4 res. | Mo. 5 result |
|---|---|---|---|---|---|---|---|---|
| P1 | 2.15E−04 | 9.30E−03 | 1.29E−04 | 9.77E+00 | −1.19E+02 | −1.56E+00 | −2.73E+00 | −2.27E+00 |
| P2 | 1.42E−04 | 8.64E−03 | 4.45E−04 | 1.22E+01 | −1.91E+02 | −1.17E−01 | −1.35E+00 | −7.10E−01 |
| P3 | 1.00E−04 | 1.11E−02 | 1.14E−01 | −1.78E+00 | 2.12E+02 | 3.53E+00 | 2.98E+00 | 3.01E+00 |

The results in Table 53A may be used to generate a probability of CAD based on the formula that: Probability=1/(1+exp(−risk score)).

As described above, the absolute molar amounts of each protein was determined using the absolute amount of the internal standard. These molar amounts were then used to determine the coefficients in Table 53B for Models 1, 3, 4, and 5. These coefficients, as they are in molar amounts, may be used in the Models, where the proteins values are determined by any type of detection assay (e.g., ELISA, mass spec., etc.).

TABLE 53B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 9.17 (5.92, 12.43) | 3.47 (1.84, 5.1) | 4.17 (2.15, 6.2) | 1.68 (−0.24, 3.59) |
| ApoA2 | 2.18 (−7.65, 12) | 0.31 (−1.02, 1.64) | 0.46 (−0.78, 1.69) | 0.06 (−3.61, 3.73) |
| ApoC2 | 5.77 (−30.06, 41.59) | 16.16 (−10.05, 42.38) | −13.16 (−47.34, 21.01) | 32.67 (0.04, 65.31) |
| ApoC3 | 157.43 (63.86, 251) | −23.08 (−60.66, 14.51) | −2.38 (−44.71, 39.95) | −34.75 (−88.39, 18.89) |
| ApoD | 4.06 (−8.24, 16.37) | −24.48 (−42.67, −6.28) | −22.57 (−44.42, −0.71) | −23.27 (−47.04, 0.51) |
| ApoE | 13.98 (−6.24, 34.2) | 3.29 (−3.97, 10.54) | 3.59 (−5.94, 13.12) | 3.25 (−5.27, 11.77) |
| ApoL1 | −706.58 (−2186.14, 772.97) | −730.01 (−2218.94, 758.92) | −1531.4 (−3384.8, 321.99) | −58.13 (−1819.62, 1703.35) |
| ApoM | −1138.55 (−3010.01, 732.91) | −208.89 (−498.11, 80.33) | −309.97 (−693, 73.06) | −113.47 (−455.94, 229) |
| CETP | 49.75 (−29.07, 128.57) | 2.87 (−5.75, 11.48) | −26.42 (−64.85, 12.01) | 4.07 (−5.59, 13.73) |
| CLU | −1.31 (−6.22, 3.59) | 3.96 (0.27, 7.65) | 5.45 (1.1, 9.8) | 3.51 (−0.8, 7.82) |
| PLTP | −1281.64 (−2396.06, −167.22) | −1204.69 (−2447.07, 37.69) | −1403.89 (−2866.09, 58.31) | −1485.79 (−3208.74, 237.15) |
| PON1 | −122.01 (−298.81, 54.79) | −98.37 (−258.11, 61.36) | −156.41 (−344.39, 31.57) | −8.03 (−194.43, 178.37) |
| SAA1/2 | −38.23 (−75.59, −0.87) | 3.53 (−9.45, 16.5) | 3.5 (−11.27, 18.27) | 6.13 (−10.01, 22.28) |

It is noted that the values in Table 53B also include a range for 95% confidence numbers. This range of numbers, for each value in the equations (Models), could be substituted into the equations.

Example 2

This example describes testing 5 panels of single and multiple HDL proteins for their ability to predict global ABCA1 cholesterol efflux (rather than global cholesterol efflux) and cardiovascular disease risk using various ABCA1 cholesterol efflux and coronary artery disease risk algorithms. The same assays and samples were measured as in Example 1 above for the five panels discussed above. The five panels are Panels 27-30 and Panel 10 as shown in Table 54 below.

TABLE 54

| Panel No. | Panel Size | Proteins |
|---|---|---|
| 27 | 5 | ApoC3; ApoE; ApoL1; HP; and PLTP |
| 28 | 15 | ApoA1; ApoA2; ApoC1; ApoC2; ApoC3; ApoC4; ApoD; ApoE; ApoL1; ApoM; C3; CLU; HP; SAA1/2; and SAA4 |
| 29 | 10 | ApoA1; ApoC3; ApoD; ApoE; ApoL1; ApoM; HP; PLTP; PON1; and SAA1/2 |

TABLE 54-continued

| Panel No. | Panel Size | Proteins |
|---|---|---|
| 30 | 13 | ApoA1; ApoA2; ApoC3; ApoC4; ApoD; ApoE; ApoL1; ApoM; C3; HP; PLTP; PON1; and SAA1/2 |
| 10 | 1 | ApoC3 |

Panel 27

Models 1-5 were developed for predicted ABCA1 cholesterol efflux and CAD risk for Panel 27. Models 1-5 are shown below for Panel 27.

Models 1-5 for Panel 27=Predicted ABCA1 cholesterol efflux=$(i)+(c1)*\text{ApoC3}+(c2)*\text{ApoE}+(c3)*\text{ApoL1}+(c4)*\text{HP}+(c5)*\text{PLTP}$ The values for Models 1-5 are shown below in Table 55.

TABLE 55

Coefficients (95% CI) of the five models

| Covariate | Model 1 on discovery samples | Model 2 on fresh/ frozen samples | Model 3 on control vs. CAD samples |
|---|---|---|---|
| Intercept | 4.46 (2.6, 6.33) | 2.59 (−0.03, 5.21) | 2.38 (1.25, 3.52) |
| ApoC3 | 82.44 (49.54, 115.35) | 109.76 (26.37, 193.14) | 10.19 (−11.98, 32.37) |
| ApoE | −712.5 (−1598.67, 173.67) | 2474.41 (74.56, 4874.26) | −1435.41 (−2427.3, −443.53) |
| ApoL1 | −129.89 (−282.78, 23) | 74.24 (−435.62, 584.11) | 16.36 (−103.18, 135.91) |
| HP | 9.67 (−1.76, 21.09) | −3.13 (−19.63, 13.36) | 2.26 (−3.78, 8.31) |
| PLTP | −9487.05 (−18613.51, −360.59) | 8083.7 (−8408.38, 24575.79) | −9257.8 (−15347.64, −3167.96) |

| Covariate | Model 4 on control vs. CAD with event samples | Model 5 on control vs. CAD without event samples |
|---|---|---|
| Intercept | 2.13 (0.78, 3.48) | 1.13 (−0.11, 2.37) |
| ApoC3 | 7.92 (−20.09, 35.93) | 10.97 (−14.26, 36.19) |
| ApoE | −1638.93 (−2916.35, −361.51) | −1202.09 (−2330.81, −73.37) |
| ApoL1 | −29.9 (−168.4, 108.61) | 77.44 (−58.44, 213.31) |
| HP | 3.78 (−3.08, 10.64) | 0.25 (−6.34, 6.83) |
| PLTP | −9687.38 (−16684.13, −2690.63) | −8454.05 (−15473.26, −1434.84) |

The predicted cholesterol efflux and CAD risk, calculated based on the five models and three specific patients, are shown below in Table 56A.

TABLE 56A

Example of three samples on the five models

| Sample ID | Group | ApoC3 | ApoE | ApoL1 | HP | PLTP | Results Model 1 | Results Model 2 | Results Model 3 | Results Model 4 | Results Model 5 |
|---|---|---|---|---|---|---|---|---|---|---|---|
| P1 | Control | 2.44E−02 | 1.43E−03 | 4.77E−03 | 9.88E−02 | 2.15E−04 | 3.76E+00 | 1.06E+01 | −1.11E+00 | −1.87E+00 | −1.74E+00 |
| P2 | CAD without event | 3.68E−02 | 9.11E−04 | 5.14E−03 | 7.74E−02 | 1.42E−04 | 5.58E+00 | 1.02E+01 | 4.00E−01 | −3.01E−01 | −3.41E−01 |
| P3 | CAD with event | 3.78E−02 | 3.61E−04 | 7.38E−03 | 1.18E−01 | 1.00E−04 | 6.55E+00 | 8.63E+00 | 1.71E+00 | 1.09E+00 | 8.64E−01 |

The results in Table 56A may be used to generate a probability of CAD based on the formula that: Probability=1/(1+exp(−risk score)).

As described above in Example 1, the absolute molar amounts of each protein was determined using the absolute amount of the internal standard. These molar amounts were then used to determine the coefficients in Table 56B for Models 1, 3, 4, and 5. These coefficients, as they are in molar amounts, may be used in the Models, where the proteins values are determined by any type of detection assay (e.g., ELISA, mass spec., etc.).

It is noted that the values in Table 56B also include a range for 95% confidence numbers. This range of numbers, for each value in the equations (Models), could be substituted into the equations.

Panel 28

Models 1-5 were developed for predicted ABCA1 cholesterol efflux and CAD risk for Panel 28. Models 1-5 are shown below for Panel 28.

Models 1-5 for Panel 28–Predicted ABCA1 cholesterol efflux=$(i)+(c1)*ApoA1+(c2)*ApoA2+(c3)*ApoC1+(c4)*ApoC2+(c5)*ApoC3+(c6)*ApoC4+(c7)*ApoD+(c8)*ApoE+(c9)*ApoL1+$

TABLE 56B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 4.1 (2.35, 5.84) | 2.79 (1.49, 4.09) | 2.72 (1.16, 4.28) | 1.54 (0.08, 3) |
| ApoC3 | 69.35 (31, 107.7) | −10.74 (−37.26, 15.78) | −11.53 (−41.53, 18.46) | −8.94 (−38.71, 20.83) |
| ApoE | 20.71 (1.25, 40.17) | 4.85 (−1.75, 11.44) | 5.19 (−2.66, 13.03) | 4.63 (−2.69, 11.94) |
| ApoL1 | −1084.86 (−2711.25, 541.53) | −376.77 (−1747.48, 993.95) | −1053.88 (−2715.49, 607.73) | 509.85 (−1049.38, 2069.08) |
| HP | 96 (−41.83, 233.83) | 37.52 (−33.74, 108.79) | 40.28 (−42.44, 122.99) | 24.54 (−51.99, 101.08) |
| PLTP | −1055.79 (−2029.23, −82.35) | −1708.84 (−2632.63, −785.05) | −1960.99 (−3067.8, −854.18) | −1598.4 (−2715.91, −480.9) |

$(c10)*\text{ApoM}+(c11)*\text{C3}+(c12)*\text{CLU}+(c13)*\text{HP}+(c14)*\text{SAA1/2}+(c15)*\text{SAA4}$ The values for Models 1-5 are shown below in Table 57.

TABLE 57

| | | | |
|---|---|---|---|
| Covariate | Model 1 on discovery samples | Model 2 on fresh/frozen samples | Model 3 on control vs. CAD samples |
| Intercept | 5.86 (2.01, 9.71) | −0.44 (−3.44, 2.55) | 5.74 (3.31, 8.18) |
| ApoA1 | −7.17 (−12.77, −1.57) | −2.78 (−8.73, 3.16) | −6.4 (−12.72, −0.09) |
| ApoA2 | 0.11 (−0.4, 0.62) | 2.11 (−0.32, 4.55) | −0.47 (−0.94, 0.01) |
| ApoC1 | −5.48 (−15.96, 5.01) | 6.4 (−18.98, 31.78) | −35.45 (−56.07, −14.83) |
| ApoC2 | 7.54 (0.21, 14.87) | 5.45 (−26.85, 37.74) | 12.22 (−5.12, 29.56) |
| ApoC3 | 75.2 (24.52, 125.87) | 36.47 (−48.46, 121.4) | 26.63 (−15.14, 68.4) |
| ApoC4 | 203.67 (−673.42, 1080.75) | 57.84 (−1613.67, 1729.35) | 725.56 (−355.11, 1806.23) |
| ApoD | 5.64 (−2.92, 14.21) | −8.34 (−27.18, 10.5) | −6.39 (−17.02, 4.24) |
| ApoE | −784.47 (−1483.78, −85.17) | 1846.85 (−341.32, 4035.02) | −456.35 (−1582.01, 669.32) |
| ApoL1 | −167.21 (−325.04, −9.38) | −252.35 (−717.53, 212.82) | −37.16 (−180.61, 106.3) |
| ApoM | −842.92 (−4793.12, 3107.29) | −854.36 (−5217.75, 3509.02) | −1160.1 (−2806.65, 486.45) |
| C3 | 6.59 (−14.35, 27.53) | 30.74 (−9.65, 71.13) | 4.97 (−12.74, 22.69) |
| CLU | −14.85 (−41.29, 11.6) | 50.55 (18.45, 82.65) | 25.57 (−8.9, 60.03) |
| HP | 4.5 (−7.95, 16.95) | −2.71 (−18.63, 13.21) | 1.47 (−6.08, 9.01) |
| SAA1/2 | −90.67 (−318.09, 136.75) | −29.11 (−319.51, 261.29) | −19.11 (−56.7, 18.48) |
| SAA4 | −33.16 (−272.31, 205.99) | −494.96 (−891.7, −98.21) | 273.36 (23.15, 523.58) |

| Covariate | Model 4 on control vs. CAD with event samples | Model 5 on control vs. CAD without event samples |
|---|---|---|
| Intercept | 7.3 (3.72, 10.89) | 4.3 (1.56, 7.04) |
| ApoA1 | −11.1 (−19.52, −2.67) | −2.77 (−10.47, 4.93) |
| ApoA2 | −0.41 (−0.99, 0.17) | −0.49 (−1.1, 0.11) |
| ApoC1 | −42.64 (−70.86, −14.41) | −39.61 (−64.43, −14.79) |
| ApoC2 | 10.41 (−11.81, 32.62) | 15.3 (−4.83, 35.42) |
| ApoC3 | 59.48 (2.43, 116.53) | 8.83 (−39.12, 56.78) |
| ApoC4 | −58.71 (−1570.14, 1452.73) | 1388.16 (95.76, 2680.57) |
| ApoD | −9.34 (−23.44, 4.77) | −5.93 (−17.57, 5.71) |
| ApoE | −158.03 (−1627.23, 1311.17) | −476.7 (−1780.64, 827.25) |
| ApoL1 | −82.01 (−266.32, 102.3) | 18.78 (−149.71, 187.28) |
| ApoM | −1986.4 (−4313.84, 341.04) | −1077.11 (−3023.31, 869.08) |
| C3 | 9.22 (−14.47, 32.91) | 0.51 (−20.14, 21.15) |
| CLU | 25.45 (−17.36, 68.26) | 22.9 (−16.73, 62.52) |
| HP | 5.76 (−3.32, 14.84) | −0.08 (−9.11, 8.95) |
| SAA1/2 | −9.24 (−72.55, 54.08) | −28.88 (−66.54, 8.77) |
| SAA4 | 312.66 (−23.78, 649.09) | 267.35 (−7.73, 542.43) |

The predicted cholesterol efflux and CAD risk, calculated based on the five models and three specific patients, are shown below in Table 58A.

TABLE 58A (broken into 2 parts)
Example of three samples on the five models

| Sample ID | Group | ApoA1 | ApoA2 | ApoC1 | ApoC2 | ApoC3 | ApoC4 | ApoD |
|---|---|---|---|---|---|---|---|---|
| P1 | Control | 3.50E−01 | 5.65E+00 | 1.54E−01 | 1.05E−01 | 2.44E−02 | 7.76E−04 | 2.18E−01 |
| P2 | CAD without event | 5.04E−01 | 3.70E+00 | 1.78E−01 | 1.64E−01 | 3.68E−02 | 1.10E−03 | 2.40E−01 |
| P3 | CAD with event | 3.50E−01 | 2.65E+00 | 9.49E−02 | 7.43E−02 | 3.78E−02 | 6.25E−04 | 5.99E−02 |

| Sample ID | ApoE | ApoL1 | ApoM | C3 | CLU | HP | SAA1/2 | SAA4 |
|---|---|---|---|---|---|---|---|---|
| P1 | 1.43E−03 | 4.77E−03 | 1.10E−03 | 6.57E−02 | 7.31E−02 | 9.88E−02 | 1.29E−04 | 5.62E−03 |
| P2 | 9.11E−04 | 5.14E−03 | 5.98E−04 | 3.51E−02 | 7.72E−02 | 7.74E−02 | 4.45E−04 | 4.92E−03 |
| P3 | 3.61E−04 | 7.38E−03 | 3.12E−04 | 3.61E−02 | 5.18E−02 | 1.18E−01 | 1.14E−01 | 6.19E−03 |

TABLE 58A-continued (broken into 2 parts)
Example of three samples on the five models

| Sample ID | Predicted ABCA1 cholesterol efflux on Model 1 | Predicted ABCA1 cholesterol efflux on Model 2 | CAD risk score on Model 3 | CAD with event risk score on Model 4 | CAD without event risk score on Model 5 |
|---|---|---|---|---|---|
| P1 | 3.88E+00 | 1.04E+04 | −1.72E+00 | −3.02E+00 | −2.54E+00 |
| P2 | 4.40E+00 | 6.76E+03 | −9.78E−01 | −3.30E+00 | −9.47E−01 |
| P3 | −5.37E+00 | 4.85E+03 | 1.27E+00 | 2.63E+00 | −5.78E−01 |

The results in Table 58A may be used to generate a probability of CAD based on the formula that: Probability=1/(1+exp(−risk score)).

As described above in Example 1, the absolute molar amounts of each protein was determined using the absolute amount of the internal standard. These molar amounts were then used to determine the coefficients in Table 58B for Models 1, 3, 4, and 5. These coefficients, as they are in molar amounts, may be used in the Models, where the proteins values are determined by any type of detection assay (e.g., ELISA, mass spec., etc.).

TABLE 58B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 6.06 (2.8, 9.33) | 4.1 (2.17, 6.03) | 5.67 (3.03, 8.31) | 2.33 (0.12, 4.53) |
| ApoA1 | −6.49 (−12.62, −0.35) | −7.12 (−11.51, −2.72) | −10.58 (−16.61, −4.54) | −5.17 (−10.62, 0.28) |
| ApoA2 | 0.37 (−7.88, 8.62) | 0.22 (−1.27, 1.72) | 0.44 (−1.02, 1.89) | −0.24 (−6.37, 5.89) |
| ApoC1 | −2.09 (−30.29, 26.12) | −78.31 (−120.96, −35.66) | −93.84 (−150.69, −37) | −79.38 (−130.72, −28.04) |
| ApoC2 | 8.17 (−30.64, 46.97) | 37.74 (0.18, 75.3) | 30.37 (−15.93, 76.67) | 48.74 (0.09, 97.39) |
| ApoC3 | 109.07 (17.43, 200.71) | 3.46 (−42.71, 49.63) | 39.77 (−13.01, 92.56) | −25.01 (−93.67, 43.65) |
| ApoC4 | 68.8 (−745.73, 883.33) | 922.24 (26.31, 1818.16) | −36.48 (−1270.51, 1197.54) | 1350.96 (350.4, 2351.53) |
| ApoD | 7.15 (−6.5, 20.8) | −16.81 (−36.5, 2.89) | −23.62 (−48.28, 1.05) | −10.71 (−34.74, 13.32) |
| ApoE | 18.33 (−4.98, 41.64) | 3.72 (−5.7, 13.13) | 6.8 (−9.11, 22.7) | 3.46 (−7.97, 14.89) |
| ApoL1 | −1133.38 (−2913.39, 646.62) | −1087.82 (−2763.5, 587.86) | −2090.17 (−4307.67, 127.34) | −47.58 (−2023.63, 1928.46) |
| ApoM | −1139.51 (−3175.59, 896.57) | −232.95 (−607.34, 141.45) | −332.23 (−841.77, 177.3) | −177.12 (−633.25, 279.01) |
| C3 | 121.04 (−97.64, 339.71) | 31.77 (−103.16, 166.7) | 42.4 (−115.96, 200.76) | −29.13 (−194.49, 136.24) |
| CLU | −3.99 (−9.57, 1.6) | 4.81 (0.68, 8.95) | 6.64 (1.48, 11.8) | 4.01 (−0.72, 8.74) |
| HP | 9.15 (−154.79, 173.1) | 38.41 (−52, 128.83) | 34.72 (−72.79, 142.23) | 48.47 (−54.46, 151.41) |
| SAA1/2 | −38.82 (−88.54, 10.91) | −2.05 (−10.18, 6.08) | −0.17 (−15.29, 14.96) | −2.08 (−9.71, 5.55) |
| SAA4 | 13.43 (−55.76, 82.62) | 36.17 (−29.84, 102.18) | 57.89 (−33.79, 149.56) | 26.76 (−48.76, 102.28) |

It is noted that the values in Table 58B also include a range for 95% confidence numbers. This range of numbers, for each value in the equations (Models), could be substituted into the equations.

Panel 29

Models 1-5 were developed for predicted ABCA1 cholesterol efflux and CAD risk for Panel 29. Models 1-5 are shown below for Panel 29.

Models 1-5 for Panel 29—Predicted ABCA1 cholesterol efflux=$(i)+(c1)*$ApoA1+$(c2)*$ApoC3+$(c3)*$ApoD+$(c4)*$ApoE+$(c5)*$ApoL1+$(c6)*$ApoM+$(c7)*$HP+$(c8)*$PLTP+$(c9)*$Pohl+$(c10)*$SAA1/2

The values for Models 1-5 are shown below in Table 59.

TABLE 59

Coefficients (95% CI) of the five models

| Covariate | Model 1 on discovery samples | Model 2 on fresh/ frozen samples | Model 3 on control vs. CAD samples |
|---|---|---|---|
| Intercept | 6.17 (2.81, 9.53) | 4.63 (1.18, 8.08) | 4.81 (3.08, 6.54) |
| ApoA1 | −3.06 (−7.65, 1.54) | 1.46 (−4.43, 7.35) | −7.81 (−12.6, −3.02) |
| ApoC3 | 84.33 (25.69, 142.96) | 102.8 (36.89, 168.72) | 25.5 (−0.25, 51.26) |
| ApoD | 2.82 (−3.57, 9.22) | −8.75 (−30.21, 12.72) | −5.52 (−14.71, 3.67) |
| ApoE | −310.38 (−925.01, 304.25) | 2124.57 (147.11, 4102.02) | −598.96 (−1624.58, 426.67) |
| ApoL1 | −89.36 (−226.09, 47.38) | 33.64 (−416.89, 484.16) | 27.28 (−109.55, 164.11) |
| ApoM | −1542.82 (−4386.69, 1301.05) | −2765.41 (−7092.31, 1561.49) | −1266.65 (−2457.1, −76.21) |
| HP | 1.41 (−6.98, 9.81) | −3.55 (−18.27, 11.17) | 3.84 (−3.1, 10.78) |

TABLE 59-continued

| | Coefficients (95% CI) of the five models | | |
|---|---|---|---|
| PLTP | −6147.77 (−14076.44, 1780.9) | 10534.9 (−5344.77, 26414.57) | −4294.98 (−11694.2, 3104.25) |
| PON1 | −23.81 (−87.72, 40.1) | −57.36 (−238.81, 124.1) | −20.9 (−122.19, 80.39) |
| SAA1/2 | −84.83 (−234.79, 65.13) | −50.01 (−435.83, 335.82) | 8.17 (−31.98, 48.33) |

| Covariate | Model 4 on control vs. CAD with event samples | Model 5 on control vs. CAD without event samples |
|---|---|---|
| Intercept | 6.23 (3.77, 8.7) | 2.99 (1.1, 4.89) |
| ApoA1 | −11.74 (−18.17, −5.31) | −5.95 (−11.56, −0.35) |
| ApoC3 | 34.31 (−3.12, 71.74) | 23.18 (−5.11, 51.47) |
| ApoD | −10.64 (−22.85, 1.56) | −3.68 (−14.16, 6.8) |
| ApoE | −658.42 (−1970.4, 653.56) | −571.45 (−1724.47, 581.57) |
| ApoL1 | −4.71 (−177.2, 167.78) | 85.06 (−67.28, 237.4) |
| ApoM | −1960.27 (−3633.11, −287.43) | −898.66 (−2198.1, 400.79) |
| HP | 7.11 (−1.33, 15.55) | 0.73 (−6.87, 8.33) |
| PLTP | −4434.05 (−13258.16, 4390.07) | −4731.19 (−13687.03, 4224.65) |
| PON1 | −26.47 (−152.46, 99.53) | −19.46 (−138.96, 100.04) |
| SAA1/2 | 5.55 (−53.25, 64.34) | 16.6 (−30.8, 64) |

The predicted cholesterol efflux and CAD risk, calculated based on the five models and three specific patients, are shown below in Table 60A.

TABLE 60A (broken into 2 parts)
Example of three samples on the five models

| Sample ID | Group | ApoA1 | ApoC3 | ApoD | ApoE | ApoL1 | ApoM | HP | PLTP | PON1 | SAA1/2 |
|---|---|---|---|---|---|---|---|---|---|---|---|
| P1 | Control | 3.50E−01 | 2.44E−02 | 2.18E−01 | 1.43E−03 | 4.77E−03 | 1.10E−03 | 9.88E−02 | 2.15E−04 | 9.30E−03 | 1.29E−04 |
| P2 | CAD without event | 5.04E−01 | 3.68E−02 | 2.40E−01 | 9.11E−04 | 5.14E−03 | 5.98E−04 | 7.74E−02 | 1.42E−04 | 8.64E−03 | 4.45E−04 |
| P3 | CAD with event | 3.50E−01 | 3.78E−02 | 5.99E−02 | 3.61E−04 | 7.38E−03 | 3.12E−04 | 1.18E−01 | 1.00E−04 | 1.11E−02 | 1.14E−01 |

| Sample ID | Predicted ABCA1 cholesterol efflux on Model 1 | Predicted ABCA1 cholesterol efflux on Model 2 | CAD risk score on Model 3 | CAD with event risk score on Model 4 | CAD without event risk score on Model 5 |
|---|---|---|---|---|---|
| P1 | 3.79E+00 | 2.29E+03 | −1.36E+00 | −2.97E+00 | −1.85E+00 |
| P2 | 5.74E+00 | 2.51E+03 | −1.16E+00 | −3.08E+00 | −1.43E+00 |
| P3 | −3.21E+00 | 8.67E+02 | 3.03E+00 | 2.63E+00 | 3.00E+00 |

The results in Table 60A may be used to generate a probability of CAD based on the formula that: Probability=1/(1+exp(−risk score)).

As described above in Example 1, the absolute molar amounts of each protein was determined using the absolute amount of the internal standard. These molar amounts were then used to determine the coefficients in Table 60B for Models 1, 3, 4, and 5. These coefficients, as they are in molar amounts, may be used in the Models, where the proteins values are determined by any type of detection assay (e.g., ELISA, mass spec., etc.).

TABLE 60B

| | Coefficients (95% CI) of the four models (based on molar values) | | | |
|---|---|---|---|---|
| Covariate | Model 1 on discovery samples | Model 3 on control vs. CAD samples | Model 4 on control vs. CAD with event samples | Model 5 on control vs. CAD without event samples |
| Intercept | 6.29 (3.15, 9.42) | 4.64 (2.91, 6.37) | 5.55 (3.32, 7.78) | 2.8 (0.88, 4.73) |
| ApoA1 | −3.69 (−9.32, 1.94) | −7.72 (−11.58, −3.85) | −11.02 (−16.37, −5.67) | −6.51 (−10.96, −2.06) |
| ApoC3 | 102.55 (44.04, 161.06) | 10.39 (−20.37, 41.16) | 19.03 (−16.16, 54.23) | 11.32 (−22.04, 44.68) |
| ApoD | 5.96 (−5.64, 17.57) | −11.93 (−30.27, 6.4) | −18.09 (−41.17, 4.98) | −5.58 (−29.09, 17.92) |
| ApoE | 16.98 (−3.82, 37.78) | 7.36 (−0.38, 15.11) | 9.52 (−4.65, 23.7) | 6.34 (−1.28, 13.95) |
| ApoL1 | −672.23 (−2017.45, 672.98) | −315.92 (−1864.41, 1232.57) | −1092.07 (−3019.76, 835.63) | 584.55 (−1203.88, 2372.98) |
| ApoM | −1155.4 (−2753.68, 442.88) | −124.05 (−421.26, 173.15) | −339.96 (−756.74, 76.82) | −4.8 (−332.51, 322.91) |
| HP | 31.77 (−116.62, 180.16) | 43.48 (−38.65, 125.61) | 52.77 (−42.73, 148.28) | 18.72 (−65.65, 103.08) |
| PLTP | −540.84 (−1413.1, 331.42) | −531.44 (−1734.4, 671.52) | −304.54 (−1749.5, 1140.42) | −806.58 (−2321.26, 708.09) |

TABLE 60B-continued

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| PON1 | −99.52 (−270.52, 71.47) | −8.88 (−164.66, 146.89) | 4.13 (−188.04, 196.3) | 9.24 (−168.96, 187.44) |
| SAA1/2 | −30.81 (−63.99, 2.37) | 3.73 (−8.18, 15.64) | 4.73 (−9.75, 19.21) | 4.84 (−10.04, 19.72) |

It is noted that the values in Table 60B also include a range for 95% confidence numbers. This range of numbers, for each value in the equations (Models), could be substituted into the equations.

Panel 30

Models 1-5 were developed for predicted ABCA1 cholesterol efflux and CAD risk for Panel 30. Models 1-5 are shown below for Panel 30.

Models 1-5 for Panel 30—Predicted ABCA1 cholesterol efflux=$(i)+(c1)*ApoA1+(c2)*ApoA2+(c3)*ApoC3+(c4)*ApoC4+(c5)*ApoD+(c6)*ApoE+(c7)*ApoL1+(c8)*ApoM+(c9)*C3+(c10)*HP+(c11)*PLTP+(c12)*POND+(c13)*SAAJ/2$ The values for Models 1-5 are shown below in Table 61.

TABLE 61

Coefficients (95% CI) of the five models

| Covariate | Model 1 on discovery samples | Model 2 on fresh/ frozen samples | Model 3 on control vs. CAD samples |
|---|---|---|---|
| Intercept | 6.4 (2.92, 9.88) | 1.86 (−1.39, 5.1) | 4.73 (2.53, 6.94) |
| ApoA1 | −3.36 (−8.03, 1.32) | 1.03 (−4.17, 6.23) | −9.36 (−15.02, −3.69) |
| ApoA2 | 0.01 (−0.34, 0.35) | 1.5 (−0.65, 3.65) | −0.07 (−0.7, 0.56) |
| ApoC3 | 87.41 (29.16, 145.65) | 62.84 (−8.53, 134.21) | 28.46 (−4.39, 61.32) |
| ApoC4 | 50.35 (−489.55, 590.25) | 252.56 (−1346.44, 1851.55) | 371.95 (−485.32, 1229.23) |
| ApoD | 3.29 (−3.54, 10.12) | −5.75 (−24.75, 13.26) | −5.23 (−14.85, 4.4) |
| ApoE | −357.71 (−987.55, 272.13) | 2023.12 (16.3, 4029.95) | −889.22 (−2003.45, 225.01) |
| ApoL1 | −99.66 (−239.5, 40.18) | −131.32 (−557.95, 295.31) | 9.67 (−129.06, 148.4) |
| ApoM | −1735.83 (−4727.18, 1255.52) | −2995.64 (−7021.95, 1030.67) | −861.44 (−2286.23, 563.34) |
| C3 | 0.01 (−11.36, 11.38) | 33.23 (−4.65, 71.1) | 10.61 (−4.64, 25.85) |
| HP | 2.24 (−6.71, 11.19) | −7.11 (−21.77, 7.55) | 1.74 (−5.53, 9.01) |
| PLTP | −6967.3 (−15065.62, 1131.03) | 7721.59 (−7019.72, 22462.89) | −4684.96 (−14405.91, 5035.98) |
| PON1 | −28.65 (−95.04, 37.75) | −84.67 (−259.2, 89.85) | −19.93 (−131.12, 91.25) |
| SAA1/2 | −97.91 (−254.37, 58.55) | −94.25 (−399.06, 210.55) | 2.26 (−34.37, 38.89) |

| Covariate | Model 4 on control vs. CAD with event samples | Model 5 on control vs. CAD without event samples |
|---|---|---|
| Intercept | 5.38 (2.51, 8.25) | 2.92 (0.32, 5.52) |
| ApoA1 | −14.4 (−21.86, −6.94) | −6.3 (−13.09, 0.49) |
| ApoA2 | 0.1 (−0.72, 0.91) | −0.01 (−0.74, 0.73) |
| ApoC3 | 57.31 (11.25, 103.37) | 13.44 (−22.92, 49.8) |
| ApoC4 | −642.91 (−1849.4, 563.57) | 1028.7 (48.1, 2009.3) |
| ApoD | −8.13 (−20.75, 4.48) | −4.48 (−15.5, 6.54) |
| ApoE | −833.88 (−2277.9, 610.13) | −962.73 (−2258.06, 332.59) |
| ApoL1 | −0.49 (−176.96, 175.99) | 69.92 (−89.59, 229.42) |
| ApoM | −1617.98 (−3505.67, 269.72) | −666.5 (−2343.43, 1010.43) |
| C3 | 15.91 (−3.34, 35.17) | 6.19 (−11.16, 23.54) |
| HP | 5.36 (−3.46, 14.19) | −1.37 (−9.57, 6.83) |
| PLTP | −6462.29 (−18930.96, 6006.38) | −7046.24 (−18694.36, 4601.87) |
| PON1 | −17.33 (−160.17, 125.51) | −23.28 (−152.16, 105.59) |
| SAA1/2 | 15.71 (−60.75, 92.17) | −0.5 (−35.53, 34.52) |

The predicted cholesterol efflux and CAD risk, calculated based on the five models and three specific patients, are shown below in Table 62A.

TABLE 62A (broken into 2 parts)
Example of three samples on the five models

| Sample ID | Group | ApoA1 | ApoA2 | ApoC3 | ApoC4 | ApoD | ApoE |
|---|---|---|---|---|---|---|---|
| P1 | Control | 3.50E−01 | 5.65E+00 | 2.44E−02 | 7.76E−04 | 2.18E−01 | 1.43E−03 |
| P2 | CAD without event | 5.04E−01 | 3.70E+00 | 3.68E−02 | 1.10E−03 | 2.40E−01 | 9.11E−04 |
| P3 | CAD with event | 3.50E−01 | 2.65E+00 | 3.78E−02 | 6.25E−04 | 5.99E−02 | 3.61E−04 |

| Sample ID | ApoL1 | ApoM | C3 | HP | PLTP | PON1 | SAA1/2 |
|---|---|---|---|---|---|---|---|
| P1 | 4.77E−03 | 1.10E−03 | 6.57E−02 | 9.88E−04 | 2.15E−04 | 9.30E−03 | 1.29E−04 |
| P2 | 5.14E−03 | 5.98E−04 | 3.51E−02 | 7.74E−02 | 1.42E−04 | 8.64E−03 | 4.45E−04 |
| P3 | 7.38E−03 | 3.12E−04 | 3.61E−02 | 1.18E−01 | 1.00E−04 | 1.11E−02 | 1.14E−01 |

| Sample ID | Predicted ABCA1 cholesterol efflux on Model 1 | Predicted ABCA1 cholesterol efflux on Model 2 | CAD risk score on Model 3 | CAD with event risk score on Model 4 | CAD without event risk score on Model 5 |
|---|---|---|---|---|---|
| P1 | 3.70E+00 | 9.54E+02 | −1.57E+00 | −2.92E+00 | −2.40E+00 |
| P2 | 5.81E+00 | 7.61E+02 | −1.63E+00 | −3.88E+00 | −1.73E+00 |
| P3 | −4.58E+00 | 3.91E+02 | 1.91E+00 | 3.23E+00 | 5.85E−01 |

The results in Table 62A may be used to generate a probability of CAD based on the formula that: Probability=1/(1+exp(−risk score)).

As described above in Example 1, the absolute molar amounts of each protein was determined using the absolute amount of the internal standard. These molar amounts were then used to determine the coefficients in Table 62B for Models 1, 3, 4, and 5. These coefficients, as they are in molar amounts, may be used in the Models, where the proteins values are determined by any type of detection assay (e.g., ELISA, mass spec., etc.).

TABLE 62B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| Intercept | 6.38 (3.18, 9.58) | 4.44 (2.61, 6.26) | 5.16 (2.84, 7.48) | 2.88 (0.82, 4.95) |
| ApoA1 | −4.04 (−10.19, 2.12) | −8.78 (−12.93, −4.62) | −11.32 (−16.84, −5.81) | −7.8 (−12.84, −2.76) |
| ApoA2 | 0.72 (−6.43, 7.86) | 0.13 (−0.95, 1.2) | 0.34 (−0.71, 1.38) | −0.21 (−3.76, 3.34) |
| ApoC3 | 100.94 (29.19, 172.68) | 1.76 (−33.77, 37.29) | 23.21 (−17.68, 64.09) | −12.99 (−64.83, 38.84) |
| ApoC4 | 175.84 (−461.33, 813.02) | 779.48 (60.48, 1498.48) | −91.06 (−1022.14, 840.02) | 1425.93 (548.44, 2303.42) |
| ApoD | 5.58 (−6.57, 17.74) | −10.5 (−29.16, 8.17) | −19.57 (−42.95, 3.82) | 3.16 (−22.22, 28.54) |
| ApoE | 17.19 (−4.35, 38.73) | 7.02 (−1.16, 15.19) | 9.78 (−4.4, 23.97) | 5.5 (−3.08, 14.07) |
| ApoL1 | −1057.3 (−2530.14, 415.55) | −571.41 (−2210.3, 1067.47) | −1453.3 (−3499.12, 592.51) | 765.63 (−1215.81, 2747.08) |
| ApoM | −1145.31 (−2811.84, 521.22) | −156.13 (−464.34, 152.09) | −280.28 (−709.47, 148.92) | −59.58 (−411.76, 292.61) |
| C3 | 104.28 (−61.84, 270.41) | 51.36 (−76.21, 178.93) | 96.15 (−46.18, 238.48) | −48.1 (−208.93, 112.74) |
| HP | 0 (−148.08, 148.08) | 37.02 (−48.06, 122.09) | 37.19 (−59.56, 133.93) | 28.8 (−65.65, 123.25) |
| PLTP | −805.68 (−1790.49, 179.14) | −626.67 (−1859.7, 606.36) | −227.19 (−1681.42, 1227.03) | −1537.64 (−3238.33, 163.06) |
| PON1 | −135.52 (−325.95, 54.91) | −17.3 (−176.5, 141.89) | 9.72 (−184.8, 204.24) | 6.95 (−184.03, 197.92) |
| SAA1/2 | −33.83 (−76, 8.33) | 1.67 (−7.85, 11.18) | 4.77 (−10.33, 19.88) | 0.11 (−7.63, 7.86) |

It is noted that the values in Table 62B also include a range for 95% confidence numbers. This range of numbers, for each value in the equations (Models), could be substituted into the equations.

Panel 10

Models 1-5 were developed for predicted ABCA1 cholesterol efflux and CAD risk for Panel 10. Models 1-5 are shown below for Panel 10.

Models 1-5 for Panel 10–Predicted ABCA1 cholesterol efflux=$(i)+(c1)*$ApoC3

The values for Models 1-5 are shown below in Table 63.

TABLE 63

Coefficients (95% CI) of the five models

| Covariate | Model 1 on discovery samples | Model 2 on fresh/ frozen samples | Model 3 on control vs. CAD samples | Model 4 on control vs. CAD with event samples | Model 5 on control vs. CAD without event samples |
|---|---|---|---|---|---|
| ApoC3 | 59.01 (58.6, 59.42) | 124.51 (124.07, 124.95) | −8.71 (−26.24, 8.82) | −15.63 (−38.04, 6.78) | −3.87 (−24.05, 16.31) |

The predicted cholesterol efflux and CAD risk, calculated based on the five models and three specific patients, are shown below in Table 64A.

TABLE 64A

Example of three samples on the five models

| Sample ID | Group | ApoC3 | Predicted ABCA1 cholesterol efflux on Model 1 | Predicted ABCA1 cholesterol efflux on Model 2 | CAD risk score on Model 3 | CAD with event risk score on Model 4 | CAD without event risk score on Model 5 |
|---|---|---|---|---|---|---|---|
| P1 | Control | 2.44E−02 | 4.63E+00 | 7.71E+00 | 8.28E−01 | 2.42E−01 | 3.60E−02 |
| P2 | CAD without event | 3.68E−02 | 5.36E+00 | 9.24E+00 | 7.21E−01 | 4.99E−02 | −1.17E−02 |
| P1 | CAD with event | 3.78E−02 | 5.42E+00 | 9.37E+00 | 7.12E−01 | 3.39E−02 | −1.57E−02 |

The results in Table 64A may be used to generate a probability of CAD based on the formula that: Probability=$1/(1+\exp(-\text{risk score}))$.

As described above in Example 1, the absolute molar amounts of each protein was determined using the absolute amount of the internal standard. These molar amounts were then used to determine the coefficients in Table 64B for Models 1, 3, 4, and 5. These coefficients, as they are in molar amounts, may be used in the Models, where the proteins values are determined by any type of detection assay (e.g., ELISA, mass spec., etc.).

TABLE 64B

Coefficients (95% CI) of the four models (based on molar values)

| Covariate | Model 1 on discovery samples | Model 3 on control vs. CAD samples | Model 4 on control vs. CAD with event samples | Model 5 on control vs. CAD without event samples |
|---|---|---|---|---|
| ApoC3 | 58.17 (57.75, 58.59) | −20.86 (−45.3, 3.59) | −25.95 (−56.69, 4.8) | −16.19 (−44.79, 12.41) |

It is noted that the values in Table 64B also include a range for 95% confidence numbers. This range of numbers, for each value in the equations (Models), could be substituted into the equations.

Example 3

Apolipoprotein A-I Associated Proteome is Associated with Cholesterol Efflux Capacity and Coronary Artery Disease This Example explored the ApoA-I-associated serum proteome and its relationship with HDL function in the context of cholesterol efflux. In addition, this study sought to build a method for predicting cholesterol efflux capacity (CEC). Serum protein fractions associating with His-tagged recombinant ApoA-I were submitted to data-dependent proteomic analysis, upon which a targeted quantitative proteomic method was developed for 21 proteins associated with reverse cholesterol transport and/or coronary artery disease (CAD). This targeted method was compared with cell-based CEC measurements (N=105) to derive a predictive proteomic algorithm which was evaluated in a case/control study of healthy (N=74) and CAD specimens with (N=83) and without (N=74) major adverse cardiovascular events. Significant overlap was observed across the ApoA-I-associated serum proteome and proteins observed in HDL. A predictive proteomic algorithm composed of ApoA-II, ApoC-I, ApoC-II, ApoC-III, ApoD and serum amyloid A (Panel 19) correlated strongly (R=0.77) with cell-based CEC assay results. Proteome-predicted CEC measurements in case/control cohorts show significant inverse association between CEC and CAD diagnosis (P=0.0032), with significantly lower CEC observed between control and CAD specimens without MACE (P=0.04) with further reduced CEC observed in CAD specimens with MACE.

Materials and Methods:

All study methods were approved by local Institutional Review Boards, as appropriate. Unless otherwise specified, all reagents were purchased from Sigma-Aldrich (St. Louis, Mo.) or ThermoFisher at the highest available quality. Specimens used in this study were obtained from Golden West biologicals which supplied pooled serum samples. Lipoprotein free serum prepared via immunoaffinity depletion was purchased from GenwayBio (San Diego, Calif.) Additionally, remnant samples from Cleveland HeartLab were used. Clinical specimens representing cases of Coronary Artery Disease and controls were obtained from the Fairbanks Institute for Healthy Communities.

Enrichment of ApoA-I Associated Serum Fraction

24 µL of 0.5 mg/mL Recombinantly expressed and purified $^{15}$N-labeled His$_6$-tagged Apolipoprotein A-I ($^{15}$N-His$_6$ApoA-I) (Genscript, Piscataway, N.J.) in 1×PBS, Ph 7.4 was added to 12 µL of human serum. The $^{15}$N-His$_6$ApoA-I/serum mixtures were incubated at 37° C. for 30 minutes. After incubation, samples were diluted to a total volume of 200 µL in 5 mm imidazole, 20 mM sodium phosphate, 150 mM sodium chloride, pH 8.0, then purified using a Tecan Freedom Evo automated liquid handler (Tecan, Mannedorf, Switzerland) equipped with PhyTips (Phynexus, San Jose, Calif.), packed with 5 µL of Ni-NTA HisBind Superflow stationary phase, according to the manufacturer's protocol. Briefly, the diluted sample was slowly bound to the Phytip columns at 250 µL/min using repeated pipetting cycles, followed by subsequent washing with 300 µL of 20 mM imidazole, 20 mM sodium phosphate, 150 mM sodium chloride, pH 8.0. Bound His$_6$-ApoA-I and associated species were then eluted with 300 mM imidazole, 50 mM Tris-HCl, pH 9.0, 25% Methanol. After elution, samples were either immediately used for subsequent analysis or stored at −80° C. until needed.

Data-Dependent Proteomic Analysis by nano-LC-MS

Dithiothreitol was added to enriched ApoA-I associated serum fraction at a final concentration of 5 mM in addition to 500 ng of Endoproteinase LysC (Wako Chemicals USA, Richmond, Va.). Samples were digested on an Eppendorf PCR thermocycler for 4 hours at 37° C., then held at 4° C. to halt endoproteinase activity. Resulting peptide mixtures were separated using a Waters nanoACQUITY Ultra High-Pressure LC system (Waters, Inc., Milford, Mass.). A 10 µL volume containing 500 ng of total peptide material was injected, trapped, and washed with mobile phase A (0.1% formic acid, 2% acetonitrile in water) at 10 µL/min for 4 minutes on a reversed-phase Symmetry C18 trapping column (180 µm i.d.×20 mm, 5 µm particle) (Waters, Inc). Peptides were then eluted at 300 nL/min on a nanoACQUITY column (75 µm i.d.×250 mm) packed with 1.7 µm BEH130 C18 stationary phase using a gradient from 2% to 50% mobile phase B (0.1% formic acid, 2% water in Acetonitrile) over 210 minutes before increasing to 100% mobile phase B for 15 minutes followed by re-equilibration at 2% mobile phase B for 15 minutes. Peptides were detected on a LTQ-Orbitrap Velos mass spectrometer (Thermo Fisher Scientific, Waltham, Mass.) using a precursor ion scan from m/z 350-1800 in the orbitrap with 120,000 resolving power followed by 25 data-dependent MS/MS events in the ion trap using collision-induced dissociation. Precursors were isolated at a 2.5 m/z isolation width, and fragmented with a normalized collision energy of 35% for 20 ms. Monoisotopic precursor selection was enabled, and precursors with 1+ and unassigned charge states were rejected from selection for MS/MS. Dynamic exclusion of precursors in a plus or minus 10 ppm mass exclusion window was utilized for 60 seconds. Automatic gain control limits were set to 1×10$^4$ and 1×10$^6$ in the ion trap and orbitrap, respectively. Mass spectrometer data files in RAW format were processed for protein identification in Max-Quant (version 1.4.1.2)[14] using the integrated Andromeda search algorithm[15]. Searches were performed against the UniProt Human Database (downloaded Oct. 14, 2013 from the European Bioinformatics Institute and consisting of 88,304 entries), in addition to a common contaminant database. Searches were carried out with a ±7 ppm precursor mass tolerance and 0.6 Da fragment mass tolerance. LysC was set as the cleaving enzyme and peptides containing at least 6 amino acids and up to 2 missed cleavages were allowed for the analysis. Methionine oxidation was allowed as a variable modification. Protein and peptide false discovery rates were set at 1%. Protein identifications were further refined to having at least 2 identified peptides.

Targeted Proteomic Analysis

Reducing agent (5 µL of 100 mM dithiothreitol) and protease (10 µL of 50 ng/µL Endoproteinase LysC (Wako)), were added to 85 µL of enriched ApoA-I associated serum fraction and incubated at 37° C. for 4 hours, at which time the temperature was reduced to 4° C. 5 µL of a defined mixture of $^{13}$C$_6$, $^{15}$N$_2$-lysine-labeled internal standard peptides was added to 75 µL of protein-digest and 25 µL subsequently injected for analysis by liquid chromatography—multiple reaction monitoring mass spectrometry (LC-MRM). Injected sample was loaded and washed on column for 1.25 minutes, and then eluted with a linear gradient of mobile phase B at 500 µL/min. Peptides were detected using an Agilent 6490 triple quadrupole mass spectrometer operating in dynamic MRM mode, allowing for the targeted detection of peptide targets within a scheduled retention time window. Transitions were selected, optimized and determined to be unique to the peptide targeted within the sample. Two transitions were monitored per peptide, and up to two peptides per protein. A detailed list of peptide targets and their transitions is available in Table 1 further above, and for Panel 19, in Table 67 below:

TABLE 67

Biomarker Panel for CEC Prediction

| Variable | Coefficients (95% CI) |
|---|---|
| Intercept | 5.6 (5.18, 6.03) |
| ApoA-II | 3.38 (2.95, 3.81) |
| ApoC-I | 19.01 (18.58, 19.44) |
| ApoC-II | 26.61 (26.18, 27.04) |
| ApoC-III | 55.92 (55.49, 56.35) |
| ApoD | 3.99 (3.56, 4.42) |
| SAA | −23.05 (−23.48, −22.62) |

Peptide signal intensities were obtained via integration the chromatographic peak for the quantifier transition using MassHunter Quantitative Analysis software (Agilent). All peaks were manually reviewed using qualifier ion ratios and internal standard peaks.

Isolation of HDL by Ultracentrifugation

HDL (1.063 g/mL<ρ<1.21 g/mL) from pooled serum was isolated using the method of Brewer with minor modifications[16].

Cell-Based Assessment of Cholesterol Efflux Capacity

Human serum samples were LDL-depleted and cell based assays to measure the efflux of $^3$H-labeled cholesterol from J774 macrophages was performed externally by Vascular Strategies, Inc., (Plymouth Meeting, Pa.) using the method described by de la Llera-Moya[17]. All measurements were reported as normalized efflux values.

Specimens for CEC Algorithm Development

Serum samples for efflux correlation model development were taken from de-identified remnant specimens at CHL collected in two batches, 6 weeks apart, for provision of training and tests sets respectively. Quantitative analyses of LDL-c, HDL-c, ApoA, ApoB, Triglycerides, and high sensitivity C-reactive protein (hsCRP) were used to guide selection of candidate samples for each set, ultimately yielding a well-matched set of specimens (Table 65).

TABLE 65

Description of Efflux Correlation Sample Cohorts

|  | Training Set | Validation Set | P-value |
|---|---|---|---|
| Number of Samples | 70 | 35 |  |
| hsCRP (mg/L) | 2.9 (3.2) | 3.4 (3.1) | 0.43 |
| ApoA1 (mg/dL) | 159 (36) | 159 (39) | 0.99 |
| ApoB (mg/dL) | 91 (22) | 107 (31) | 0.01 |
| ApoB/ApoA1 ratio | 0.61 (0.23) | 0.72 (0.29) | 0.06 |
| Total Cholesterol (mg/dL) | 192 (33) | 200 (48) | 0.39 |
| LDL-C (mg/dL) | 109 (31) | 115 (41) | 0.41 |
| HDL-C (mg/dL) | 59 (21) | 55 (22) | 0.42 |
| non-HDL-C (mg/dL) | 133 (35) | 150 (56) | 0.11 |
| Triglycerides (mg/dL) | 123 (70) | 148 (60) | 0.06 |

Quantitative ApoA-I associated proteome analyses and CEC measurements were collected for 105 specimens along with highly-characterized serum pools as quality control material.

Specimens for Clinical Validation

Specimens were selected from the Fairbanks Institute for Healthy Communities biobank which consists of serum samples from 1500 men and women aged 22 to 87; 750 with documented diagnosis of CAD via coronary angiography (≥50% occlusion) and 750 control subjects with no positive findings for CAD, positive stress test, diabetes, hypertension, or abnormal lipids (LDL-C≥130 mg/dL, HDL-C≤40 mg/dL, total cholesterol ≥240 mg/dL or triglycerides ≥200 mg/dL). Fasting blood samples were collected according to the study SOP and subsequently stored at −80° C. Subjects with diagnosed CAD were evaluated to establish two groups, cases, and cases with events. All CAD patients were filtered for ICD-9 code codes for major adverse cardiovascular events (MACE); myocardial infarction (410), coronary bypass graft or angioplasty (36.1, 45.82), or stroke (434.91). For confirmation of myocardial infarct from ICD9 screening, records were reviewed to select patients with two of three of the following—history of ischemic pain, abnormal ECG, abnormal troponin. In total, 74 CAD subjects without events and 83 CAD subjects with MACE events were selected (Table 66).

A set of 74 matched controls were also selected.

Targeted Algorithm Development

Prior to computational analysis, the peak area abundance of each targeted peptide was normalized to the intensity of $^{15}$N-His$_6$ApoA-I used during the enrichment process. For proteins with two or more peptides measured by LC-MS/MS, the relative amount of protein was established using the peptide with highest intensity in the majority of samples analyzed. Protein-level data was used in the statistical analysis. An analytical pipeline encompassing a series of sequential steps for feature selection was applied to normalized protein-level data to discover proteins associated with CEC[18]. For univariate analysis, a robust linear regression was applied to each protein to predict CEC on 70 training samples and proteins with p-value <0.1 was selected. Further filtering was applied using elastic net model. For multivariate analysis, a biomarker panel was built on the filtered proteins using a partial least-squares regression. To assess the performance of biomarker panels, spearman correlation and median absolute difference (cost) between predicted CEC and measured CEC were calculated. Initially the biomarker panel was developed using uncalibrated LC-MS peak intensities. The proteomic method was later improved to provide calibrated absolute molar quantities and panel coefficients were refined on the calibrated MRM data using partial least-squares regression. Finally, the panel was tested with 35 validation samples. To assess if the predictive CEC biomarker panel could differentiate between subjects with and without CAD, we tested the biomarker proteins in the 74 healthy controls and 157 CAD patients. Statistical analysis of the data was performed using R version 3.2.3 (R Core Team (2013). R: A language and environment for statistical computing, R Foundation for Statistical Computing, Vienna, Austria). Comparison of cumulative patient cohort distributions was performed using the Kolmogorov-Smirnov (K-S) test.

Results:

Rapid ApoA-I Affinity Pool Preparation

A strategy for rapid affinity enrichment was devised to facilitate the precise, high-throughput analysis of lipid free ApoA-I associated proteins using mass spectrometry-based

TABLE 66

Description Fairbanks Study Cohorts

Figure 2:
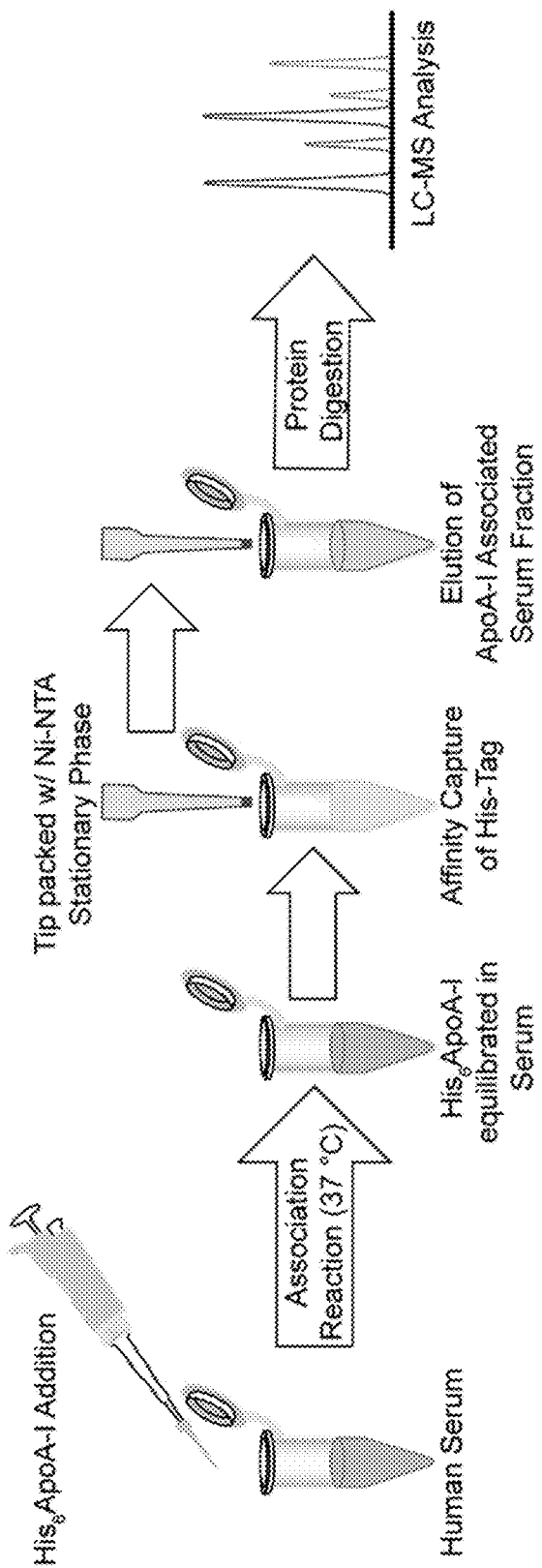
FIG. 2: Isolation of ApoA-I-Associated Serum Fraction—Overview schematic of the isolation of ApoA-I associating proteins by incubating serum with $His_6$ApoA-I and targeting the His-tag using immobilized metal affinity chromatography (IMAC).

|  | Control | | CAD | | p-value | CAD w/Event | | p-value |
|---|---|---|---|---|---|---|---|---|
| Gender | Male | Female | Male | Female |  | Male | Female |  |
|  | n = 35 (47%) | n = 39 (53%) | n = 47 (64%) | n = 27 (36%) |  | n = 50 (60%) | n = 33 (40%) |  |
| Age | 55 (8) |  | 58 (8) |  | 0.093 | 59 (11) |  | 0.019 |
| BMI | 26.9 (4.8) |  | 30.5 (6.7) |  | <0.001 | 31.3 (7.1) |  | <0.001 |
| White Ethnicity | 69 (93%) |  | 71 (96%) |  |  | 75 (90%) |  |  |
| hsCRP (mg/L) | 3.0 (3.7) |  | 4.8 (8.6) |  | 0.167 | 5.0 (4.6) |  | 0.106 |
| ApoA1 (mg/dL) | 194 (35) |  | 170 (34) |  | <0.001 | 159 (28) |  | <0.001 |
| ApoB (mg/dL) | 112 (25) |  | 100 (26) |  | 0.004 | 109 (34) |  | 0.545 |
| ApoB/ApoA1 ratio | 0.60 (0.17) |  | 0.60 (0.18) |  | 0.774 | 0.71 (0.26) |  | 0.002 |
| Total Cholesterol (mg/dL) | 227 (39) |  | 190 (39) |  | <0.001 | 195 (49) |  | <0.001 |
| LDL-C (mg/dL) | 127 (32) |  | 98 (31) |  | <0.001 | 104 (40) |  | <0.001 |
| HDL-C (mg/dL) | 69 (19) |  | 55 (19) |  | <0.001 | 48 (13) |  | <0.001 |
| non-HDL-C (mg/dL) | 158 (41) |  | 135 (37) |  | <0.001 | 147 (49) |  | 0.140 |
| Triglycerides (mg/dL) | 152 (88) |  | 187 (124) |  | 0.051 | 223 (112) |  | <0.001 |
| Events |  |  |  |  |  |  |  |  |
| Revascularization | — |  | — |  |  | 29 (35%) |  |  |
| Myocardial Infarction | — |  | — |  |  | 38 (46%) |  |  |
| Stroke | — |  | — |  |  | 16 (19%) |  |  | proteomics. This strategy used His-tagged ApoA-I and immobilized metal-affinity chromatography (FIG. 2). Recombinant, lipid-free ApoA-I with an N-terminal polyhistidine tag (His$_6$ApoA-I) was added to human serum and incubated at 37° C. The sample was then passed over a nickel-NTA stationary phase to bind the His$_6$ApoA-I and associated proteins. After washing the stationary phase with low concentrations of imidazole to reduce non-specifically bound proteins, the complexed proteins and excess His$_6$ApoA-I are eluted in the desired recovery buffer containing high-concentration imidazole. The eluted sample was then subjected to a standard enzymatic digestion workflow for eventual liquid chromatography mass spectrometry (LC-MS/MS) analysis. We used $^{15}$N-labelled His$_6$ApoA-I ($^{15}$N-His$_6$ApoA-I) to allow the specific measurement of exogenous ApoA-I to be distinguished from the endogenous protein belonging to the specimen being analyzed.

Data-Dependent Proteomic Analysis of the Lipid Free ApoA-I Affinity Pool

Early data-dependent experiments revealed that most proteins identified in the lipid-free ApoA-I affinity fraction are known to be HDL-associated. We sought to further clarify this observation with a qualitative proteome comparison of HDL isolated using traditional ultracentrifugation and the ApoA-I associated serum fraction using a commercially available serum pool of 400 male donors. Three process replicates were performed for each enrichment technique. Overall, 91 proteins were identified in HDL purified by ultracentrifugation and 162 proteins were identified the lipid free ApoA-I affinity pool, with 78 proteins shared between both preparation methods (see FIG. 3).

Figure 3:
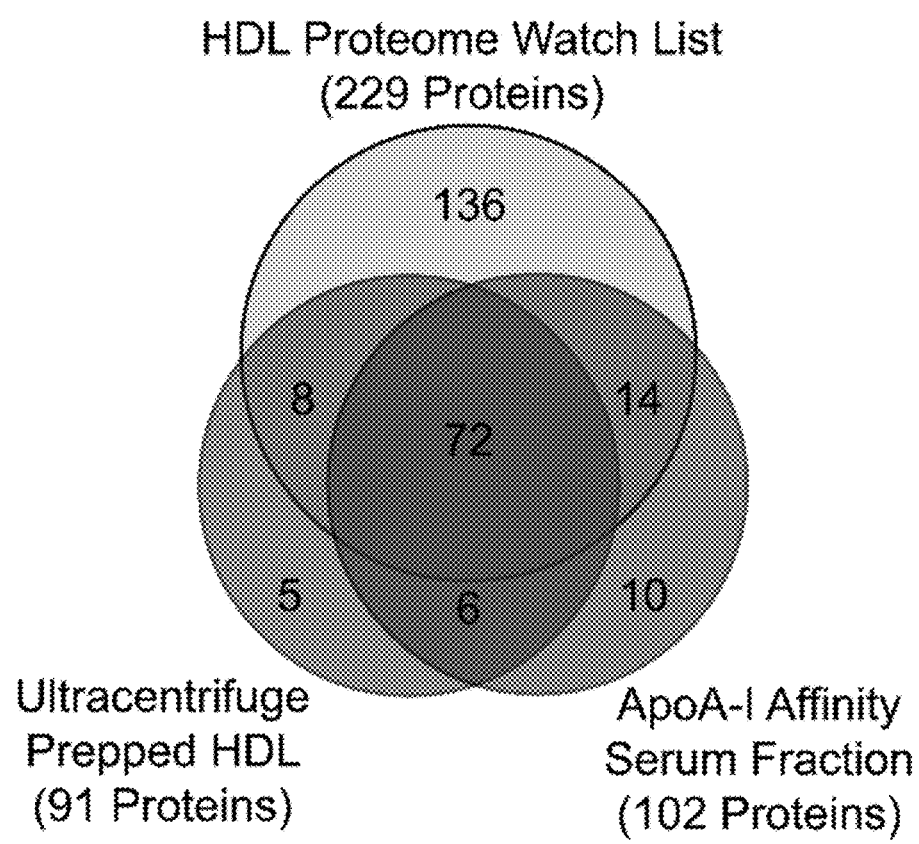
FIG. 3: Overlap of ApoA-I Associated and HDL Proteomes—Venn diagram illustrating the overlap of proteins identified by ApoA-I Affinity purification with HDL prepared by gradient ultracentrifugation in the context of the HDL Proteome Watch list.

We compared the proteins identified in our experiment to the HDL Proteome Watch list which summarizes the results of 17 published HDL proteome studies. The list contains 229 proteins, with 95 proteins being identified in 3 or more studies or verified by other molecular biology techniques. Of all 229 proteins in the Proteome Watch list, 80 were identified in HDL prepared by ultracentrifugation, and 86 were identified in our affinity purified pool with 72 (excluding common contaminants such as keratin) shared between both preparation methods (77% overlap) (FIG. 3)

Targeted Quantitation by Multiple-Reaction Monitoring Mass Spectrometry

Figure 6:
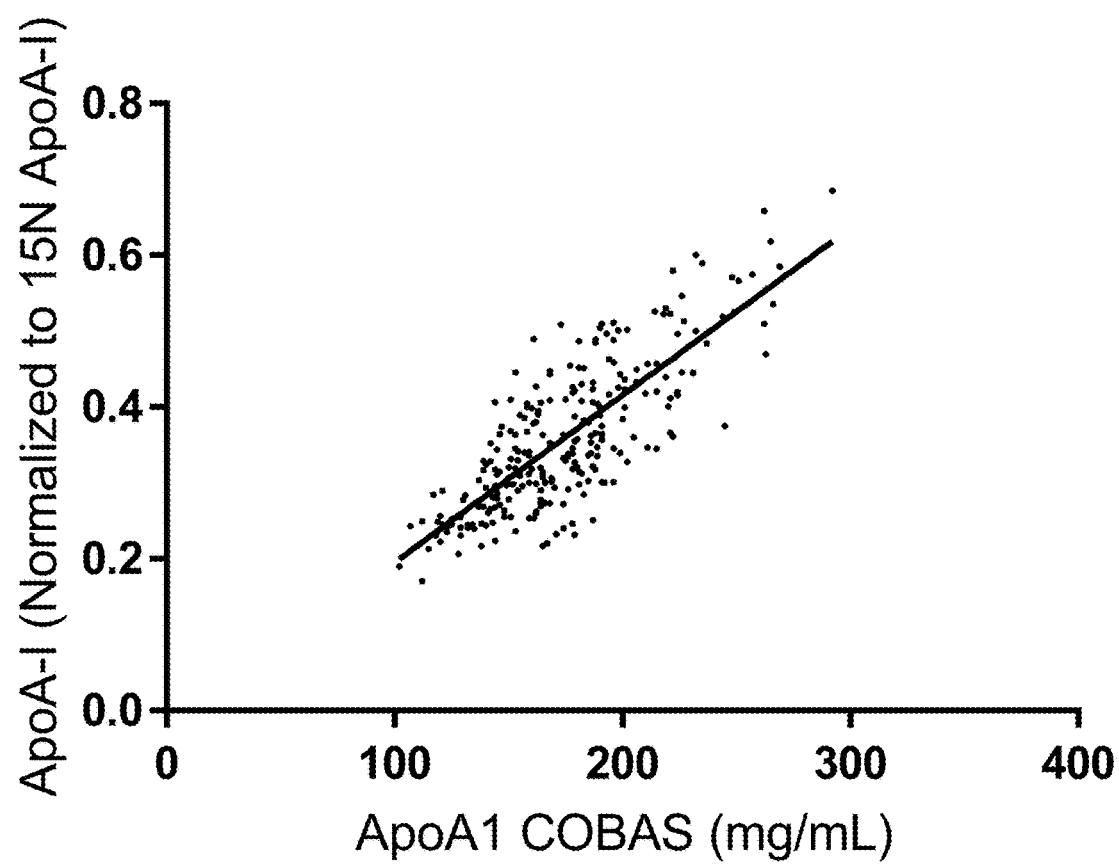
FIG. 6: Correlation of endogenous ApoA-I observed in Targeted MRM measurement of ApoA-I associated proteins with serum ApoA-I levels measured by immunoturbidometric analysis in a reference clinical laboratory.

To explore the relationship between ApoA-I affinity pools and cholesterol efflux capacity (CEC) we sought to use a precise quantitative method based on liquid chromatography-multiple reaction monitoring (LC-MRM). Based on a literature search and our data-dependent LC-MS results, 21 proteins with known associations with lipid transport, reverse cholesterol transport and/or cardiovascular disease were selected for development (lipid metabolism (Apolipoproteins A-I, A-II, A-IV, C-I, C-II, C-IV, D, E, F, J, L-I, M), enzymes (Phospholipid Transfer Protein—PLTP, Cholesteryl ester transfer protein—CETP, lecithin cholesterol acyl transferase—LCAT, paraoxonase 1—PON1), and acute phase response proteins (Complement C3, Haptoglobin, Serum Amyloid A 1 and 2-SAA1/2, and SAA4)). Two peptides from each protein (where possible) were identified for assay development and the entire workflow was optimized. Digest conditions were obtained which yielded stable peptide abundances for all proteins within 4 hours. Recoveries of native ApoA-I from neat serum were estimated to be approximately 55% and strongly correlated to ApoA-I levels in serum as determined by immunoassay (Pearson r=0.84, Supplemental FIG. 6). In comparison, mean recovery of lipid free $^{15}$N-His$_6$ApoA-I from PBS buffer was 85% and 72% from stripped serum.

Development and Validation of a Multivariate Algorithm for CEC Prediction

Using the lipid-free ApoA-I affinity enrichment technique, we analyzed a set of serum samples to explore whether a relationship existed between affinity-enriched proteins and CEC. A set of 70 training and 35 independent test samples (Table 65) were randomly selected without respect to any disease diagnosis but were carefully matched on lipoprotein measurements. Normalized CEC and normalized mass spectrometry data for the compliment of 21 proteins were determined for each specimen. A multi-step informatics pipeline including univariate and multivariate statistical methods was deployed for the development of a biomarker panel correlating relative protein abundance to cell-based CEC[18]. After univariate analysis, 9 proteins (Apolipoproteins A-I, A-II, C-I, C-II, C-IV, D, CETP, and SAA) with p-value <0.1 were identified by robust linear regression. Subsequent elastic net regression selected 6 proteins (ApoA-II, ApoC-I, ApoC-II, ApoC-III, ApoD, and SAA) on which partial linear regression was applied to establish the final predictive model.

Figure 4:
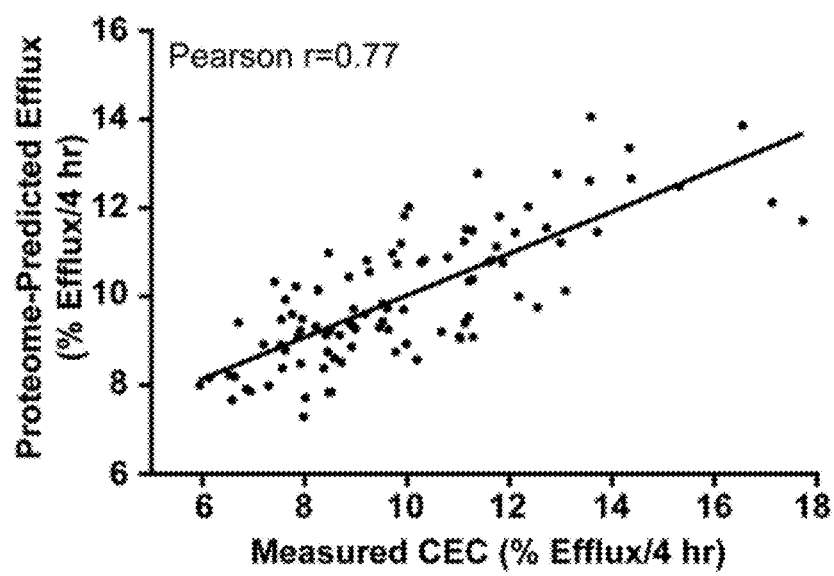
FIG. 4: Associations with Cell-Based Cholesterol Efflux Assay—Correlation of measured cholesterol efflux capacity (CEC) from cAMP-stimulated J774 macrophages with (A) Predicted CEC using a 6-protein panel based on the targeted analysis of ApoA-I associated serum proteins, and serum concentrations of (B) ApoA-I, (C) HDL, and (D) hsCRP.
Figure 4:
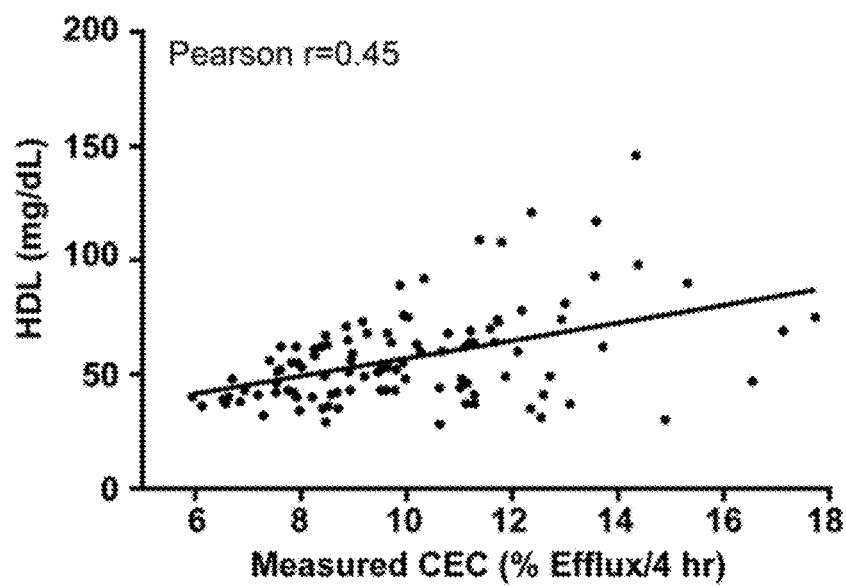
Figure 4:
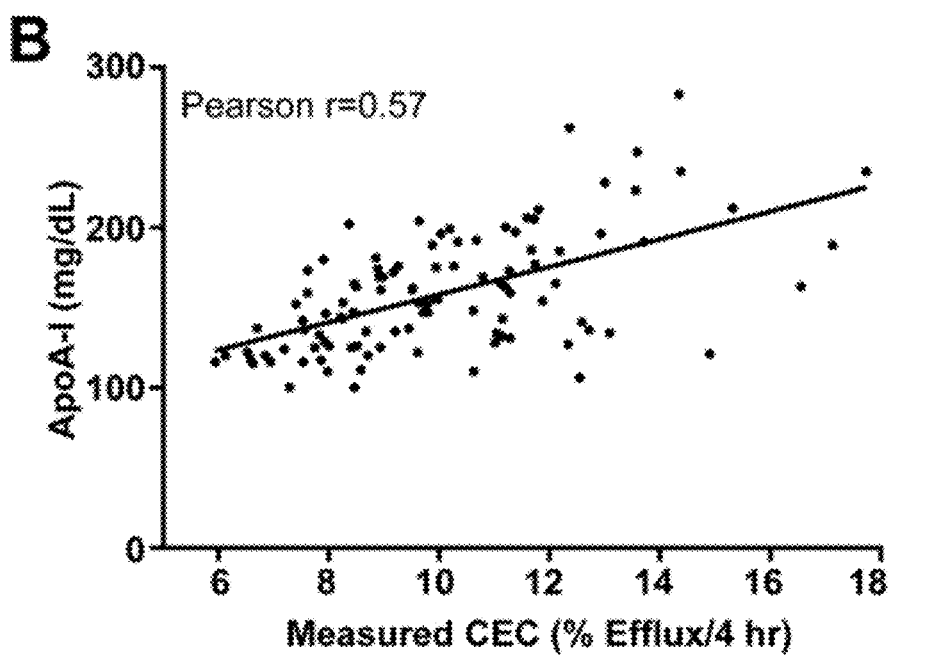
Figure 4:
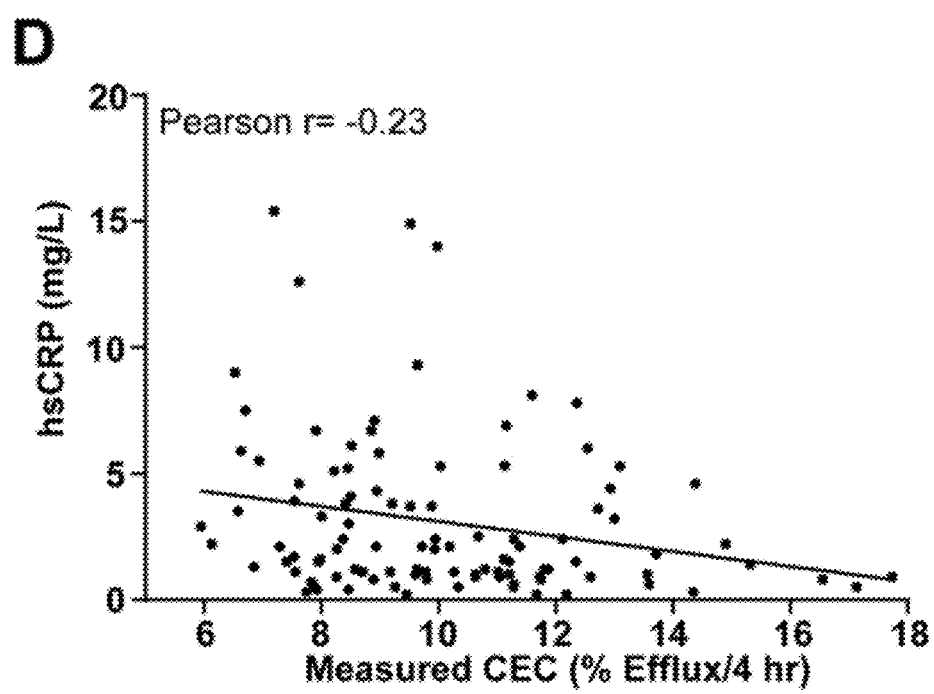

The predictive panel performed well given the measured imprecision in the CEC measurements (training set spearman r=0.63, p<0.001; validation set Spearman r=0.70, P<0.001). The performance of the proteome-predicted CEC algorithm within the entire development sample set is shown in FIG. 4A (Pearson r=0.77). The associations between CEC determined by cell-based assay and proteomic estimation and other clinical measurements (Total Cholesterol, HDL-c, LDL-c, non-HDL-c, Triglycerides, ApoA-I, ApoB, and hsCRP) were examined. The most significant associations with cell based CEC were with ApoA-I (Pearson r=0.57, FIG. 4B) and HDL-c (Pearson r=0.45, FIG. 4C), in agreement with previous reports[11,12]. We also observed a significant negative correlation between CEC and hsCRP (Pearson r=−0.23, FIG. 4D). Predicted CEC behaved similarly with respect to Total Cholesterol but relationships to ApoA-I and HDL-c were not calculated due to the inclusion of ApoA-I in the proteome panel.

Predicted CEC is Inversely Associated with CAD

Assuming predicted CEC should have similar inverse association with cardiovascular disease as reported for cell-based CEC measurements, we used our multivariate panel to predict CEC for 157 CAD patients (74 without major adverse cardiovascular events (MACE), 83 with MACE) and 74 age and sex-matched apparently healthy controls (Table 66).

Figure 5:
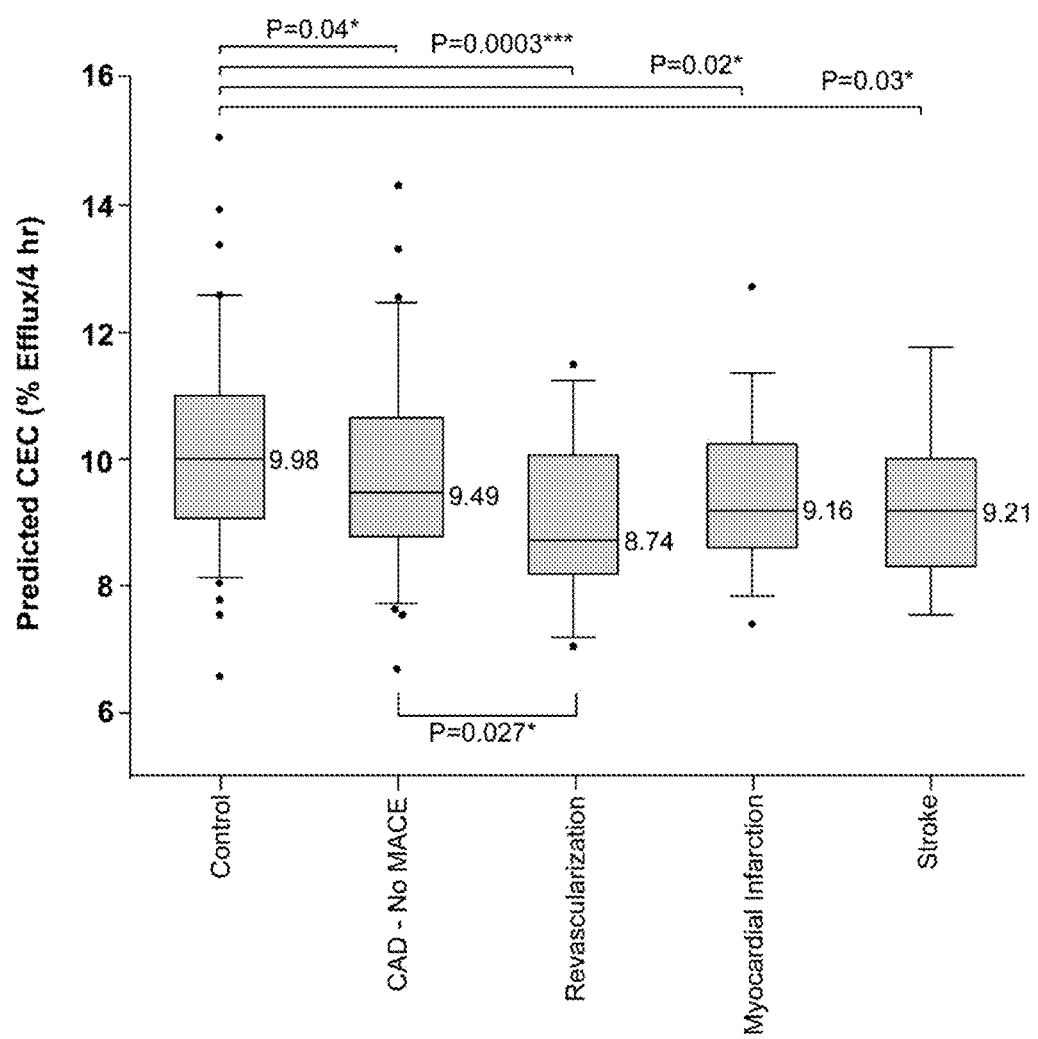
FIG. 5: Inverse Association of Predicted CEC and CAD—Distributions of CEC predicted by targeted HDL proteome analysis. Comparisons of total control and CAD patient population (with and without MACE).
Figure 7:
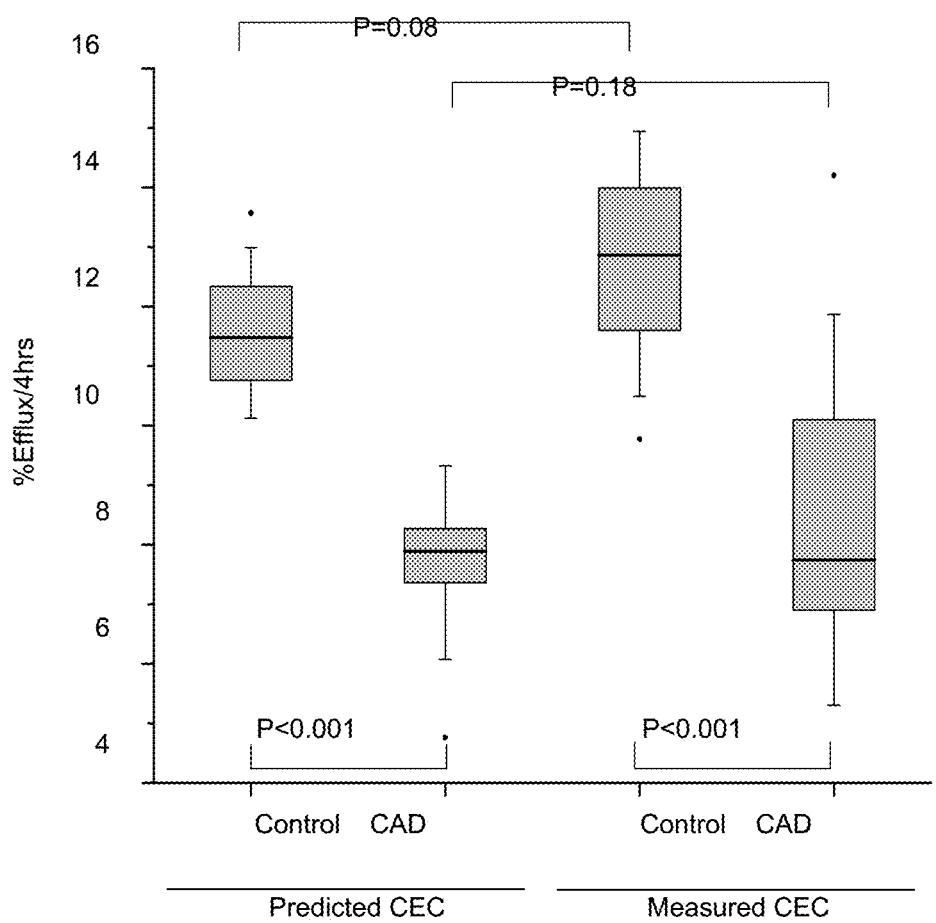
FIG. 7: Comparison of predicted CEC from targeted HDL Proteome analysis of 30 samples (n=15 Control, n=15 CAD) with the measured cellular cholesterol efflux by cell-based assay of the same sample set in cAMP-stimulated J774 macrophages.

The distribution of predicted CEC across these cohorts is illustrated in FIG. 5A. We found lower median predicted CEC for patients with CAD (9.54% efflux/4 hr; control 9.98% efflux/4 hr; p=0.0032). When CAD cases are split into those without MACE and specific adverse events, we observe significantly lower predicted CEC in CAD patients without MACE relative to controls (P=0.04). CAD patients that underwent revascularization (n=29) displayed lower predicted CEC than CAD patients without MACE (P=0.027, P=0.0003 relative to Control). CAD patients that experienced a myocardial infarction (n=38) or stroke (n=16), while displaying lower median predicted CEC, were not significantly different from CAD patients with no MACE. A repeat comparison of age and gender matched control and CAD samples was performed 6 weeks later and demonstrated confirmed the trends observed in the initial analysis. We also performed a comparison of the performance of predicted CEC and cell-based CEC measurements in a small selection of the samples with clinical outcomes. Cell based CEC measurements were obtained after 15 highest and lowest predicted CEC values in the control and CAD cohorts were respectively identified. As shown in Supplemental FIG. 7, the CAD specimen subset had significantly lower CEC as determined by both proteome-predicted and cell-based CEC measurements (P-values <0.001). Additionally, no significant difference was evident when comparing the same outcome subsets across predicted and cell-based measurements (P=0.39 for Control, P=0.08 for CAD).

Determination of CEC via cell-based assay has been undisputedly powerful for the interrogation of cholesterol metabolism and a growing number of studies have shown serum based CEC measurement to be an independent predictor of cardiovascular risk. Unfortunately, labor intensity, workflow complexity, and relative imprecision of the method compromise the translation of this technique to the clinical laboratory where scale, throughput, precision, calibration, and, ultimately, analytical validation are necessary achievements.

Proteome-Predicted CEC Performance

Performance of proteome-predicted CEC in the test set (r=0.71) is encouraging and suggests a key role for proteins other than ApoA-I in modulation of cholesterol efflux. Recent clinical studies of CEC deploying a modified cell based assay using fluorescently labeled cholesterol found significant predictive value where the agreement to normalized efflux using the predicate radioisotope assay was modest (R=0.54)[12]. Other correlates to efflux have been identified. As expected, a positive univariate association to ApoA-I has been reported in many studies ranging from r=0.22 to 0.64 (r=0.57 in this study)[11,19]. In high HDL-C (>68 mg/dL) specimens the sphingomyelin/phosphorylethanolamine ratio was demonstrated to be significantly associated with efflux (r=0.64) but not associated at normal HDL-C levels. Efflux is also known to be dependent on HDL subclass further suggesting a complex set of structural and functional interactions[20]. The diversity of these remains to be fully elucidated but provides opportunity for integration of additional biochemical and biophysical data into models which could improve CEC prediction.

Mechanistic Insights of CEC-Predictive Panel Proteins

The proteomic predictor of CEC derived in our study is composed of proteins (Apolipoproteins A-II, C-I, C-II, D, and SAA; Panel 19) that are mechanistically associated with cholesterol transport. For proteins with positive association to efflux, ApoA-I and ApoA-II function as a primary acceptors of cellular cholesterol[1,21]. ApoC-I is likewise a minor, but efficient, cholesterol acceptor and also activates Lecithin-cholesterol acyltransferase LCAT which plays a role in HDL maturation[22]. ApoC-II and ApoC-III regulate lipoprotein lipase involved in HDL remodeling, and ApoD plays a role in the formation of pre-$\beta_3$-HDL, a potent cellular cholesterol-accepting form of HDL[22,23]. Serum Amyloid A (SAA) is an acute-phase response protein and has been extensively characterized as having a negative impact on cholesterol efflux capacity through displacement of ApoA-I from HDL[24,25]. We also noted that the functional role that SAA plays in modulating efflux is reflected in the negative association between efflux and hsCRP—another commonly measured systemic inflammation biomarker (but not identified as ApoA-I associating in this study). Intriguingly, the interactions between lipid-free ApoA-I and serum proteins as revealed by proteomic analysis displays a high degree of overlap with the canonical HDL proteome as cataloged in the Proteome Watch list.

REFERENCES FOR THIS EXAMPLE

1. Kontush A, Chapman M J. High-Density Lipoproteins: Structure, Metabolism, Function, and Therapeutics. John Wiley & Sons, Inc; 2012.
2. Drew et al., High-density lipoprotein and apolipoprotein AI increase endothelial NO synthase activity by protein association and multisite phosphorylation. Proc Natl Acad Sci. 2004; 101(18):6999-7004.
3. Ansell et al. Inflammatory/Antiinflammatory Properties of High-Density Lipoprotein Distinguish Patients from Control Subjects Better Than High-Density Lipoprotein Cholesterol Levels and Are Favorably Affected by Simvastatin Treatment. Circulation. 2003; 108(22):2751-2756.
4. Gaidukov L, Tawfik D S. High Affinity, Stability, and Lactonase Activity of Serum Paraoxonase PON1 Anchored on HDL with ApoA-I. Biochemistry. 2005; 44(35):11843-11854.
5. Huang et al. Myeloperoxidase, paraoxonase-1, and HDL form a functional ternary complex. J Clin Invest. 2013; 123(9):3815-3828.
6. Cavigiolio et al., Exchange of apolipoprotein A-I between lipid-associated and lipid-free states: a potential target for oxidative generation of dysfunctional high density lipoproteins. J Biol Chem. 2010; 285(24):18847-18857.
7. Fredolini et al. Immunocapture strategies in translational proteomics. Expert Rev Proteomics. 2016; 13(1):83-98.
8. Gavin et al. Functional organization of the yeast proteome by systematic analysis of protein complexes. Nature. 2002; 415(6868):141-147.
9. Gundry et al., Investigation of an albumin-enriched fraction of human serum and its albuminome. Proteomics—Clin Appl. 2007; 1(1):73-88.
10. Poulsen et al., Serum Amyloid P Component (SAP) Interactome in Human Plasma Containing Physiological Calcium Levels. Biochemistry. 2017; 56(6):896-902.
11. Khera, et al. Cholesterol efflux capacity, high-density lipoprotein function, and atherosclerosis. N Engl J Med. 2011; 364(2):127-135.
12. Rohatgi et al. HDL cholesterol efflux capacity and incident cardiovascular events. N Engl J Med. 2014; 317(25):2383-2393.
13. Mody et al., Beyond Coronary Calcification, Family History, and C-Reactive Protein. J Am Coll Cardiol. 2016; 67(21):2480-2487.
14. Cox J, Mann M. MaxQuant enables high peptide identification rates, individualized p.p.b.-range mass accuracies and proteome-wide protein quantification. Nat Biotechnol. 2008; 26(12):1367-1372.
15. Cox et al., a peptide search engine integrated into the MaxQuant environment. J Proteome Res. 2011; 10(4): 1794-1805.
16. Duverger et al., Biochemical characterization of the three major subclasses of lipoprotein A-I preparatively isolated from human plasma. Biochemistry. 1993; 32(46): 12372-12379.
17. de la Llera-Moya et al., The ability to promote efflux via ABCA1 determines the capacity of serum specimens with similar high-density lipoprotein cholesterol to remove cholesterol from macrophages. Arterioscler Thromb Vasc Biol. 2010; 30(4):796-801.
18. Sin et al., Biomarker Development for Chronic Obstructive Pulmonary Disease. From Discovery to Clinical Implementation. Am J Respir Crit Care Med. 2015; 192(10):1162-1170.
19. Saleheen et al. Association of HDL cholesterol efflux capacity with incident coronary heart disease events: a prospective case-control study. Lancet Diabetes & Endocrinol. 2015; 3(7):507-513.
20. Du et al. HDL particle size is a critical determinant of ABCA1-mediated macrophage cellular cholesterol export. Circ Res. 2015; 116(7):1133-1142.

21. Rotllan et al., Overexpression of Human Apolipoprotein A-II in Transgenic Mice Does Not Impair Macrophage-Specific Reverse Cholesterol Transport In Vivo. Arterioscler Thromb Vasc Biol. 2005; 25(9).
22. von Eckardstein A, Nofer J-R, Assmann G. High Density Lipoproteins and Arteriosclerosis: Role of Cholesterol Efflux and Reverse Cholesterol Transport. Arterioscler Thromb Vasc Biol. 2001; 21(1):13-27.
23. Francone O L, Fielding C J. Initial steps in reverse cholesterol transport: the role of short-lived cholesterol acceptors. Eur Heart J. 1990; 11(suppl E).
24. Vaisar et al. Inflammatory remodeling of the HDL proteome impairs cholesterol efflux capacity. J Lipid Res. 2015; 56(8):1519-1530.
25. Banka et al., Serum amyloid A (SAA): influence on HDL-mediated cellular cholesterol efflux. J Lipid Res. 1995; 36(5):1058-1065.

Example 4

This Example applied Panel 18 (ApoA1, ApoC1, ApoC2, ApoC3, and ApoC4) to the Fairbanks Institute for Healthy Communitities sample and to a subset of the Abcodia Biobank.

Figure 8:
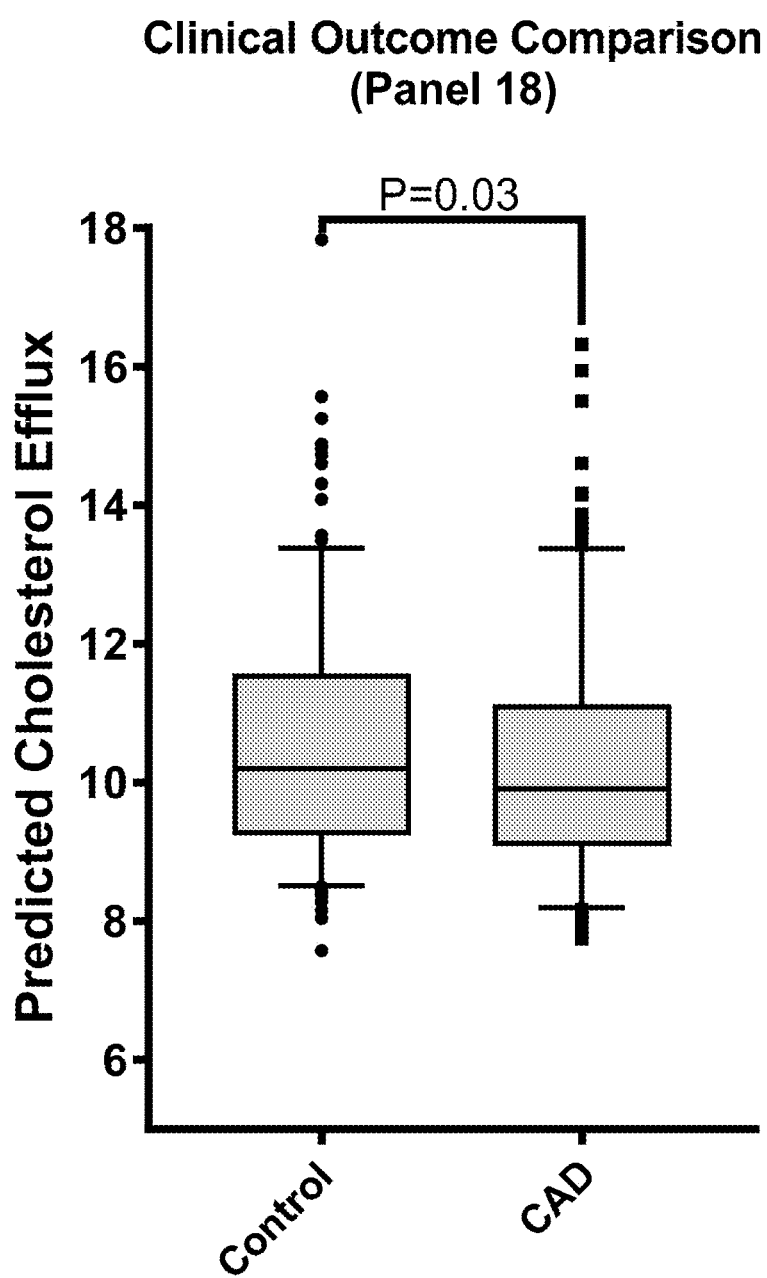
FIG. 8 shows results from Example 4, comparing the predicted cholesterol efflux values across cohorts reveals overall lower cholesterol efflux for the CAD cohort relative to the control cohort.
Figure 9:
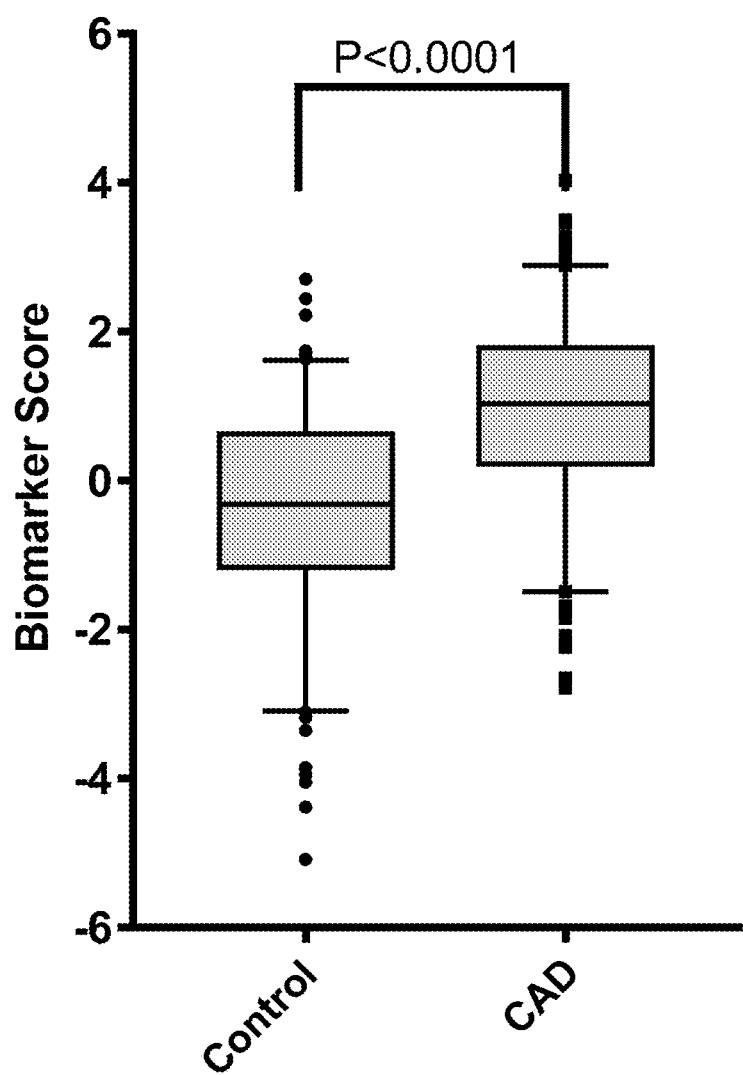
FIG. 9 shows the results from Example 4 of application of the outcome optimized model stratifies patients on a biomarker score scale which correlates to risk of having a diagnosis of CAD.

The Fairbanks Institute for Healthy Communities (Fairbanks Institute) has created an extensively annotated biospecimen repository for hypothesis-driven research. These biological samples are linked with longitudinal clinical and disease-specific health records information drawn from the Indiana Network for Patient Care (INPC), a state-wide electronic clinical data repository. The Fairbanks Institute's CAD collection, which was used, includes serum and plasma, from individuals with a diagnosis of coronary artery disease as well as from matched controls. Using this sample set, cholesterol efflux prediction model based on molar protein quantities measured by mass spectrometry (Table 37B, Model 1) was applied to the sample set comprised of patients that were healthy (control) (n=74) or had been diagnosed with coronary artery disease (CAD) (n=157). Comparing the predicted cholesterol efflux values across these cohorts reveals overall lower cholesterol efflux for the CAD cohort relative to the control cohort (P=0.03 by Mann-Whitney test), as shown in FIG. 8. Performing logistic regression on the protein components of panel 18 to optimize separation of clinical outcomes (Control vs CAD) gives rise to the parameters in Table 37, Model 3. When applied to the Fairbanks clinical set, we observe improved stratification of patient cohorts based on outcomes. Application of the outcome optimized model stratifies patients on a biomarker score scale which correlates to risk of having a diagnosis of CAD, as shown in FIG. 9. Here, the CAD cohort shows significantly elevated biomarker scores relative to the control group (P<0.0001 by Mann-Whitney Test).

We also applied models from Panel 18 to a subset of the Abcodia Biobank which is composed of 200,000 postmenopausal women aged 50-74, 50,000 of which were sampled longitudinally over the course of several years. In this study, control patients were matched by sampling location, age, and date and time of sampling to cases identified by non-fatal myocardial infarction. Both model 1 and model 3 (Table 37B) show persistent and statistically significant separation between these cohorts across a range of 0-8 years prior to the occurrence of the event.

TABLE 68

| Timepoint | GroupSizes | Model 1 (Efflux Prediction) P-Value (Mann-Whitney) | Model 3 (Control vs CAD) P-Value (Mann-Whitney) |
| --- | --- | --- | --- |
| 0-3 yrs preDx | 208 vs 207 | 4.35E−06 | 9.30E−08 |
| 1-2 yrs preDx | 69 vs 68 | 0.0053 | 0.00025 |
| 2-3 yrs preDx | 64 vs 64 | 0.027 | 0.00073 |
| 3-4 yrs preDx | 57 vs 57 | 0.015 | 0.024 |
| 4-5 yrs preDx | 44 vs 44 | 0.22 | 0.048 |
| 5-8 yrs preDx | 35 vs 35 | 0.082 | 0.0017 |

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A system comprising:
   a) a sample from a subject with, or suspected of having, cardiovascular disease, wherein said sample comprises high density lipoprotein (HDL) particles, apolipoprotein A1 (ApoA1), or HDL-cholesterol;
   b) a first component, wherein said first component comprises:
      i) an Apolipoprotein C3 (ApoC3) binding agent, and/or
      ii) an ApoC3 mass spectrometry standard; and
   c) a second component comprising a detectably labeled apolipoprotein A1 (ApoA1) protein or fragment thereof, wherein said detectably labeled ApoA1 protein serves as a calibrator for normalizing levels of one or more HDL-associated proteins in said sample to the level of total HDL particles, ApoA1, or HDL-cholesterol present in said sample, wherein at least one of the one or more HDL-associated proteins is ApoC3.

2. The system of claim 1, wherein said sample is selected from the group consisting of: a serum sample, a plasma sample, and a blood sample.

3. The system of claim 1, further comprising d) a third component comprising: i) an apolipoprotein A1 (ApoA1) binding agent, and/or ii) an ApoA1 mass spectrometry standard.

4. The system of claim 1, further comprising d) a third component comprising: i) an apolipoprotein C1 (ApoC1) binding agent, and/or ii) an ApoC1 mass spectrometry standard.

5. The system of claim 1, further comprising d) a third component comprising: i) an apolipoprotein C2 (ApoC2) binding agent, and/or ii) an ApoC2 mass spectrometry standard.

6. The system of claim 5, wherein the ApoC2 binding agent is an anti-ApoC2 antibody or binding portion thereof, or an anti-ApoC2 nucleic acid or protein aptamer or binding portion thereof; and/or wherein the ApoC2 mass spectrometry standard is an ApoC2 protein or fragment thereof.

7. The system of claim 6, wherein the ApoC2 protein or fragment thereof comprises the amino acid sequence of SEQ ID NOS: 9 or 10.

8. The system of claim 1, wherein the ApoC3 binding agent is an anti-ApoC3 antibody or binding portion thereof, or an anti-ApoC3 nucleic acid or protein aptamer or binding portion thereof.

9. The system of claim 1, wherein the ApoC3 mass spectrometry standard is an ApoC3 protein or fragment thereof.

10. The system of claim 9, wherein the ApoC3 protein or fragment thereof is isotope-labeled.

11. The system of claim 9, wherein the ApoC3 protein or fragment thereof comprises the amino acid sequence of SEQ ID NO: 11.

12. The system of claim 3, wherein the ApoA1 binding agent is an anti-ApoA1 antibody or binding portion thereof, or anti-ApoA1 nucleic acid or protein aptamer or binding portion thereof, and/or wherein the ApoA1 mass spectrometry standard is an ApoA1 protein or fragment thereof.

13. The system of claim 12, wherein the ApoA1 protein or fragment thereof comprises the amino acid sequence of SEQ ID NOS: 1 or 2.

14. The system of claim 4, wherein the ApoC1 binding agent is an anti-ApoC1 antibody or binding portion thereof, or an anti-ApoC1 nucleic acid or protein aptamer or binding portion thereof; and/or wherein the ApoC1 mass spectrometry standard comprises is an ApoC1 protein or fragment thereof.

15. The system of claim 14, wherein the ApoC1 protein or fragment thereof comprises the amino acid sequence of SEQ ID NOS: 7 or 8.

16. The system of claim 1, further comprising d) a third component comprising: i) an apolipoprotein C4 (ApoC4) binding agent, and/or ii) an ApoC4 mass spectrometry standard.

17. The system of claim 16, wherein the ApoC4 binding agent is an anti-ApoC4 antibody or binding portion thereof, or an anti-ApoC4 nucleic acid or protein aptamer or binding portion thereof; and/or wherein the ApoC4 mass spectrometry standard is an ApoC4 protein or fragment thereof.

18. The system of claim 1, further comprising d) a third component comprising: i) an apolipoprotein D (ApoD) binding agent, and/or ii) an ApoD mass spectrometry standard.

19. The system of claim 18, wherein the ApoD binding agent is an anti-ApoD antibody or binding portion thereof, or an anti-ApoD nucleic acid or protein aptamer or binding portion thereof; and/or wherein the ApoD mass spectrometry standard is an ApoD protein or fragment thereof.

20. The system of claim 1, further comprising d) a third component comprising: i) a serum amyloid A 1/2 (SAA1/2) binding agent, and/or ii) an SAA1/2 mass spectrometry standard.

21. The system of claim 20, wherein the SAA1/2 binding agent is an anti-SAA1/2 antibody or binding portion thereof, or an anti-SAA1/2 nucleic acid or protein aptamer or binding portion thereof; and/or wherein the SAA1/2 mass spectrometry standard is an SAA1/2 protein or fragment thereof.

* * * * *

UNITED STATES PATENT AND TRADEMARK OFFICE
CERTIFICATE OF CORRECTION

PATENT NO. : 10,921,331 B2
APPLICATION NO. : 15/656592
DATED : February 16, 2021
INVENTOR(S) : Bystrom et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 211 days.

Signed and Sealed this
Thirtieth Day of August, 2022

Katherine Kelly Vidal
*Director of the United States Patent and Trademark Office*

SEQUENCE LISTING

```
<160> NUMBER OF SEQ ID NOS: 37

<210> SEQ ID NO 1
<211> LENGTH: 11
<212> TYPE: PRT
<213> ORGANISM: Homo sapiens

<400> SEQUENCE: 1

Ala Thr Glu His Leu Ser Thr Leu Ser Glu Lys
1               5                   10

<210> SEQ ID NO 2
<211> LENGTH: 14
<212> TYPE: PRT
<213> ORGANISM: Homo sapiens
```

-continued

```
<400> SEQUENCE: 2

Leu Leu Asp Asn Trp Asp Ser Val Thr Ser Thr Phe Ser Lys
1               5                   10

<210> SEQ ID NO 3
<211> LENGTH: 8
<212> TYPE: PRT
<213> ORGANISM: Homo sapiens

<400> SEQUENCE: 3

Glu Gln Leu Thr Pro Leu Ile Lys
1               5

<210> SEQ ID NO 4
<211> LENGTH: 9
<212> TYPE: PRT
<213> ORGANISM: Homo sapiens

<400> SEQUENCE: 4

Ser Pro Glu Leu Gln Ala Glu Ala Lys
1               5

<210> SEQ ID NO 5
<211> LENGTH: 14
<212> TYPE: PRT
<213> ORGANISM: Homo sapiens

<400> SEQUENCE: 5

Leu Val Pro Phe Ala Thr Glu Leu His Glu Arg Leu Ala Lys
1               5                   10

<210> SEQ ID NO 6
<211> LENGTH: 9
<212> TYPE: PRT
<213> ORGANISM: Homo sapiens

<400> SEQUENCE: 6

Val Asn Ser Phe Phe Ser Thr Phe Lys
1               5

<210> SEQ ID NO 7
<211> LENGTH: 9
<212> TYPE: PRT
<213> ORGANISM: Homo sapiens

<400> SEQUENCE: 7

Ala Arg Glu Leu Ile Ser Arg Ile Lys
1               5

<210> SEQ ID NO 8
<211> LENGTH: 7
<212> TYPE: PRT
<213> ORGANISM: Homo sapiens

<400> SEQUENCE: 8

Gln Ser Glu Leu Ser Ala Lys
1               5

<210> SEQ ID NO 9
<211> LENGTH: 11
<212> TYPE: PRT
<213> ORGANISM: Homo sapiens

<400> SEQUENCE: 9
```

```
Glu Ser Leu Ser Ser Tyr Trp Glu Ser Ala Lys
1               5                   10
```

<210> SEQ ID NO 10
<211> LENGTH: 9
<212> TYPE: PRT
<213> ORGANISM: Homo sapiens

<400> SEQUENCE: 10

```
Thr Tyr Leu Pro Ala Val Asp Glu Lys
1               5
```

<210> SEQ ID NO 11
<211> LENGTH: 7
<212> TYPE: PRT
<213> ORGANISM: Homo sapiens

<400> SEQUENCE: 11

```
Asp Tyr Trp Ser Thr Val Lys
1               5
```

<210> SEQ ID NO 12
<211> LENGTH: 7
<212> TYPE: PRT
<213> ORGANISM: Homo sapiens

<400> SEQUENCE: 12

```
Ala Trp Phe Leu Glu Ser Lys
1               5
```

<210> SEQ ID NO 13
<211> LENGTH: 11
<212> TYPE: PRT
<213> ORGANISM: Homo sapiens

<400> SEQUENCE: 13

```
Asn Ile Leu Thr Ser Asn Asn Ile Asp Val Lys
1               5                   10
```

<210> SEQ ID NO 14
<211> LENGTH: 10
<212> TYPE: PRT
<213> ORGANISM: Homo sapiens

<400> SEQUENCE: 14

```
Tyr Leu Gly Arg Trp Tyr Glu Ile Glu Lys
1               5                   10
```

<210> SEQ ID NO 15
<211> LENGTH: 20
<212> TYPE: PRT
<213> ORGANISM: Homo sapiens

<400> SEQUENCE: 15

```
Leu Glu Glu Gln Ala Gln Gln Ile Arg Leu Gln Ala Glu Ala Phe Gln
1               5                   10                  15

Ala Arg Leu Lys
            20
```

<210> SEQ ID NO 16
<211> LENGTH: 20
<212> TYPE: PRT
<213> ORGANISM: Homo sapiens

<400> SEQUENCE: 16

```
Ser Glu Leu Glu Glu Gln Leu Thr Pro Val Ala Glu Glu Thr Arg Ala
1               5                   10                  15

Arg Leu Ser Lys
            20

<210> SEQ ID NO 17
<211> LENGTH: 11
<212> TYPE: PRT
<213> ORGANISM: Homo sapiens

<400> SEQUENCE: 17

Asp Ala Asn Ile Ser Gln Pro Glu Thr Thr Lys
1               5                   10

<210> SEQ ID NO 18
<211> LENGTH: 9
<212> TYPE: PRT
<213> ORGANISM: Homo sapiens

<400> SEQUENCE: 18

Leu Asn Ile Leu Asn Asn Asn Tyr Lys
1               5

<210> SEQ ID NO 19
<211> LENGTH: 13
<212> TYPE: PRT
<213> ORGANISM: Homo sapiens

<400> SEQUENCE: 19

Trp Trp Thr Gln Ala Gln Ala His Asp Leu Val Ile Lys
1               5                   10

<210> SEQ ID NO 20
<211> LENGTH: 20
<212> TYPE: PRT
<213> ORGANISM: Homo sapiens

<400> SEQUENCE: 20

Glu Phe Pro Glu Val His Leu Gly Gln Trp Tyr Phe Ile Ala Gly Ala
1               5                   10                  15

Ala Pro Thr Lys
            20

<210> SEQ ID NO 21
<211> LENGTH: 13
<212> TYPE: PRT
<213> ORGANISM: Homo sapiens

<400> SEQUENCE: 21

Leu Phe Leu Ser Leu Leu Asp Phe Gln Ile Thr Pro Lys
1               5                   10

<210> SEQ ID NO 22
<211> LENGTH: 12
<212> TYPE: PRT
<213> ORGANISM: Homo sapiens

<400> SEQUENCE: 22

Pro Ala Leu Leu Val Leu Asn His Glu Thr Ala Lys
1               5                   10

<210> SEQ ID NO 23
<211> LENGTH: 10
```

```
<212> TYPE: PRT
<213> ORGANISM: Homo sapiens

<400> SEQUENCE: 23

Glu Ile Gln Asn Ala Val Asn Gly Val Lys
1               5                   10

<210> SEQ ID NO 24
<211> LENGTH: 18
<212> TYPE: PRT
<213> ORGANISM: Homo sapiens

<400> SEQUENCE: 24

Leu Phe Asp Ser Asp Pro Ile Thr Val Thr Val Pro Val Glu Val Ser
1               5                   10                  15

Arg Lys

<210> SEQ ID NO 25
<211> LENGTH: 14
<212> TYPE: PRT
<213> ORGANISM: Homo sapiens

<400> SEQUENCE: 25

Ala Phe Ser Asp Arg Asn Thr Leu Ile Ile Tyr Leu Asp Lys
1               5                   10

<210> SEQ ID NO 26
<211> LENGTH: 9
<212> TYPE: PRT
<213> ORGANISM: Homo sapiens

<400> SEQUENCE: 26

Thr Gly Leu Gln Glu Val Glu Val Lys
1               5

<210> SEQ ID NO 27
<211> LENGTH: 12
<212> TYPE: PRT
<213> ORGANISM: Homo sapiens

<400> SEQUENCE: 27

Asp Ile Ala Pro Thr Leu Thr Leu Tyr Val Gly Lys
1               5                   10

<210> SEQ ID NO 28
<211> LENGTH: 10
<212> TYPE: PRT
<213> ORGANISM: Homo sapiens

<400> SEQUENCE: 28

Val Thr Ser Ile Gln Asp Trp Val Gln Lys
1               5                   10

<210> SEQ ID NO 29
<211> LENGTH: 19
<212> TYPE: PRT
<213> ORGANISM: Homo sapiens

<400> SEQUENCE: 29

Asp Arg Phe Ile Asp Gly Phe Ile Ser Leu Gly Ala Pro Gln Gly Gly
1               5                   10                  15

Ser Ile Lys
```

```
<210> SEQ ID NO 30
<211> LENGTH: 11
<212> TYPE: PRT
<213> ORGANISM: Homo sapiens

<400> SEQUENCE: 30

Thr Tyr Ser Val Glu Tyr Leu Asp Ser Ser Lys
1               5                   10

<210> SEQ ID NO 31
<211> LENGTH: 8
<212> TYPE: PRT
<213> ORGANISM: Homo sapiens

<400> SEQUENCE: 31

Gly Leu Arg Glu Val Ile Glu Lys
1               5

<210> SEQ ID NO 32
<211> LENGTH: 22
<212> TYPE: PRT
<213> ORGANISM: Homo sapiens

<400> SEQUENCE: 32

Gln Glu Gly Leu Arg Phe Leu Glu Gln Glu Leu Glu Thr Ile Thr Ile
1               5                   10                  15

Pro Asp Leu Arg Gly Lys
            20

<210> SEQ ID NO 33
<211> LENGTH: 9
<212> TYPE: PRT
<213> ORGANISM: Homo sapiens

<400> SEQUENCE: 33

Ser Phe Asn Pro Asn Ser Pro Gly Lys
1               5

<210> SEQ ID NO 34
<211> LENGTH: 11
<212> TYPE: PRT
<213> ORGANISM: Homo sapiens

<400> SEQUENCE: 34

Tyr Val Tyr Ile Ala Glu Leu Leu Ala His Lys
1               5                   10

<210> SEQ ID NO 35
<211> LENGTH: 12
<212> TYPE: PRT
<213> ORGANISM: Homo sapiens

<400> SEQUENCE: 35

Tyr Phe His Ala Arg Gly Asn Tyr Asp Ala Ala Lys
1               5                   10

<210> SEQ ID NO 36
<211> LENGTH: 9
<212> TYPE: PRT
<213> ORGANISM: Homo sapiens

<400> SEQUENCE: 36

Ala Glu Glu Trp Gly Arg Ser Gly Lys
1               5
```

```
<210> SEQ ID NO 37
<211> LENGTH: 12
<212> TYPE: PRT
<213> ORGANISM: Homo sapiens

<400> SEQUENCE: 37

Asp Pro Asp Arg Phe Arg Pro Asp Gly Leu Pro Lys
1               5                   10
```